(12) United States Patent
Kaneko et al.

(10) Patent No.: US 6,991,769 B2
(45) Date of Patent: *Jan. 31, 2006

(54) BIOMASS GASIFYCATION FURNACE AND SYSTEM FOR METHANOL SYNTHESIS USING GAS PRODUCED BY GASIFYING BIOMASS

(75) Inventors: Shozo Kaneko, Tokyo (JP); Susumu Sato, Tokyo (JP); Yoshinori Kobayashi, Tokyo (JP); Tatsuo Kabata, Tokyo (JP); Kazuto Kobayashi, Tokyo (JP); Yoshiyuki Takeuchi, Hiroshima (JP); Kimishiro Tokuda, Nagasaki (JP); Akira Hashimoto, Nagasaki (JP); Katsuhiko Shinoda, Nagasaki (JP); Keiji Takeno, Nagasaki (JP); Shinji Matsumoto, Nagasaki (JP); Hideaki Ohta, Nagasaki (JP); Tsugio Yamamoto, Nagasaki (JP); Masayasu Sakai, Nagasaki (JP); Toshiyuki Takegawa, Nagasaki (JP); Yajyuro Seike, Nagasaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 727 days.

This patent is subject to a terminal disclaimer.

(21) Appl. No.: 09/959,506

(22) PCT Filed: Feb. 26, 2001

(86) PCT No.: PCT/JP01/01390

§ 371 (c)(1),
(2), (4) Date: Jan. 28, 2002

(87) PCT Pub. No.: WO01/64819

PCT Pub. Date: Sep. 7, 2001

(65) Prior Publication Data

US 2002/0159929 A1 Oct. 31, 2002

(30) Foreign Application Priority Data

| Feb. 29, 2000 | (JP) | 2000-053228 |
| Feb. 29, 2000 | (JP) | 2000-053229 |
| Mar. 2, 2000 | (JP) | 2000-57209 |
| Mar. 2, 2000 | (JP) | 2000-57210 |
| Mar. 29, 2000 | (JP) | 2000-090598 |
| Jul. 26, 2000 | (JP) | 2000-225051 |
| Jul. 26, 2000 | (JP) | 2000-225052 |
| Sep. 19, 2000 | (JP) | 2000-284308 |

(51) Int. Cl.
*C01J 3/46* (2006.01)

(52) U.S. Cl. .................. 422/187; 422/188; 422/190; 422/191; 422/211

(58) Field of Classification Search ............... 422/191, 422/188, 211, 187, 190; 204/275.1
See application file for complete search history.

(56) References Cited

U.S. PATENT DOCUMENTS 4,497,637 A 2/1985 Purdy et al.

(Continued)

FOREIGN PATENT DOCUMENTS

CA 1059765 8/1979

(Continued)

OTHER PUBLICATIONS

Masayasu Sakai "Biomass ga Hiraku 21 Seiki Energy" Oct. 30, 1998 Morikita Shuppan (Tokyo) pp. 48-57.

*Primary Examiner*—N. Bhat
(74) *Attorney, Agent, or Firm*—Birch, Stewart, Kolasch & Birch, LLP

(57) ABSTRACT

Methanol is synthesized from a gas produced through gasification of biomass serving as a raw material, making use of a biomass feeding means for feeding biomass into a furnace main body and, located above the biomass feeding means, combustion-oxidizing-agent-feeding means for feeding into the furnace main body a combustion-oxidizing agent containing oxygen or a mixture of oxygen and steam.

37 Claims, 50 Drawing Sheets

U.S. PATENT DOCUMENTS

| | | |
|---|---|---|
| 5,900,224 A | 5/1999 | Fujimura et al. |
| 6,645,442 B2 * | 11/2003 | Kaneko et al. ............. 422/187 |
| 2004/0247499 A1 * | 12/2004 | Matsuoka et al. .......... 422/191 |

FOREIGN PATENT DOCUMENTS

| | | |
|---|---|---|
| CA | 1079972 | 6/1980 |
| CA | 1198895 | 1/1986 |
| CA | 2176966 A1 | 3/1994 |
| CA | 2 330 302 A1 | 4/1999 |
| CA | 2 349 608 A1 | 5/2000 |
| CA | 2 372 195 A1 | 11/2000 |
| JP | 49-6001 | 1/1974 |
| JP | 63-120825 A | 5/1988 |
| JP | 10-236801 | 9/1998 |
| JP | 2948344 | 7/1999 |
| JP | 2948345 | 7/1999 |
| JP | 3009536 | 12/1999 |
| JP | 3009541 | 12/1999 |

* cited by examiner

F I G. 12
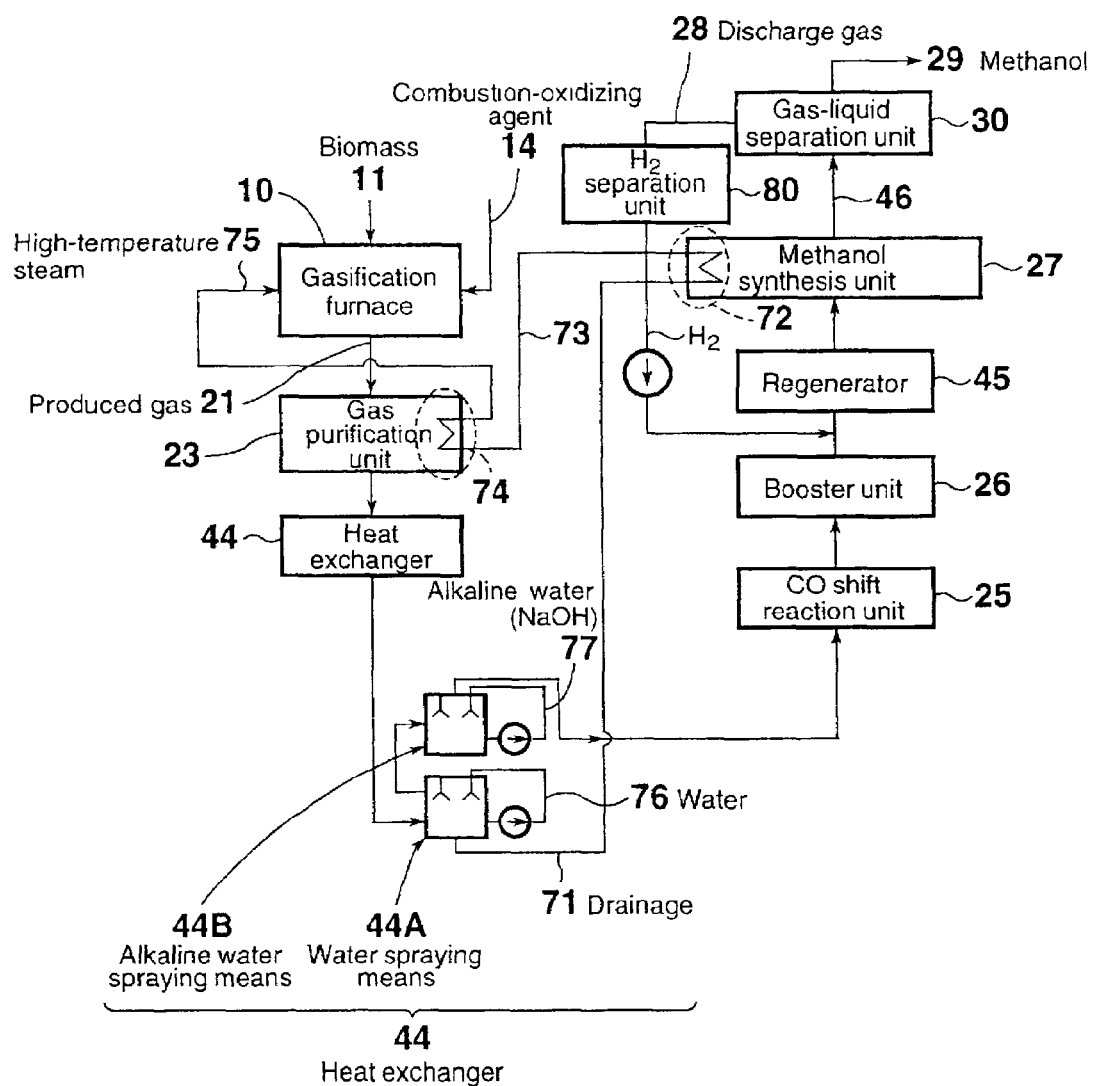

F I G. 30
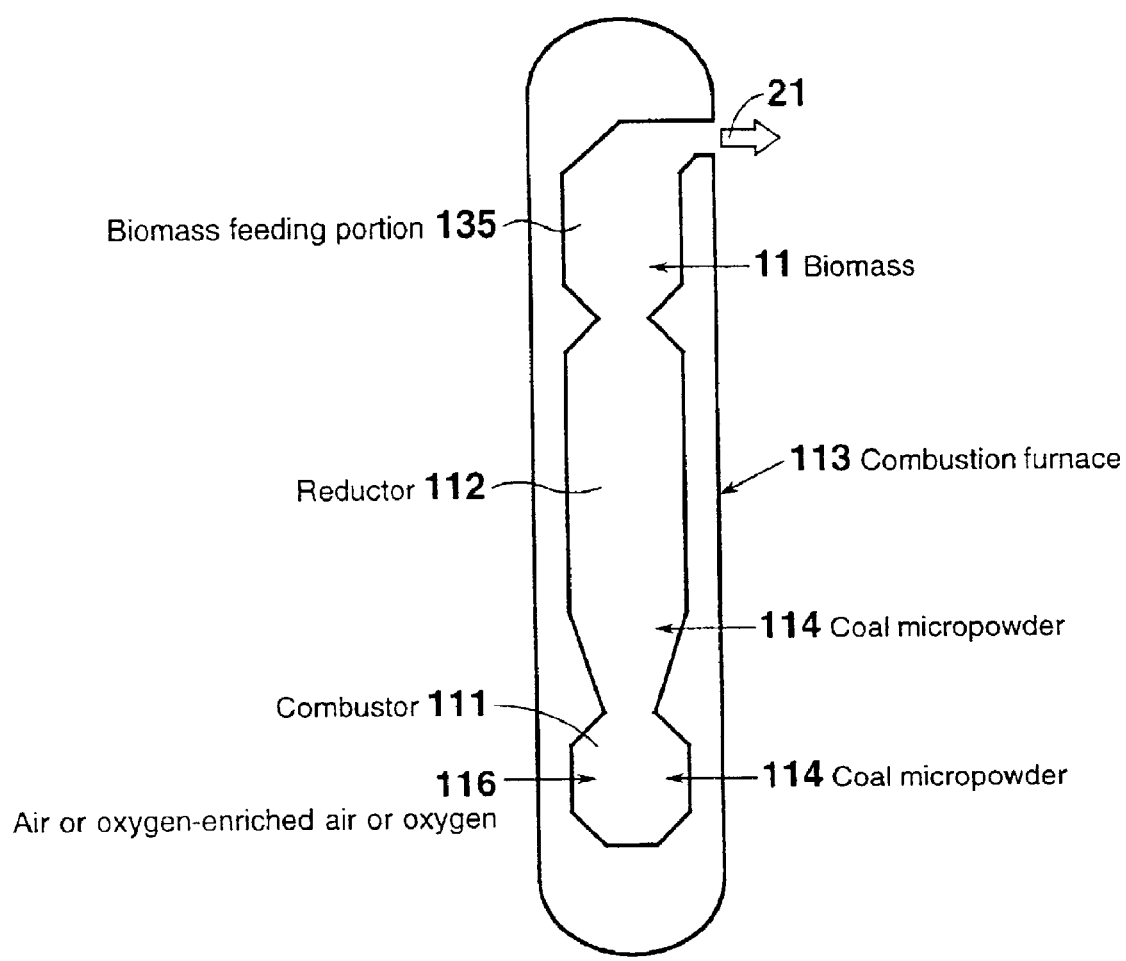

F I G. 41
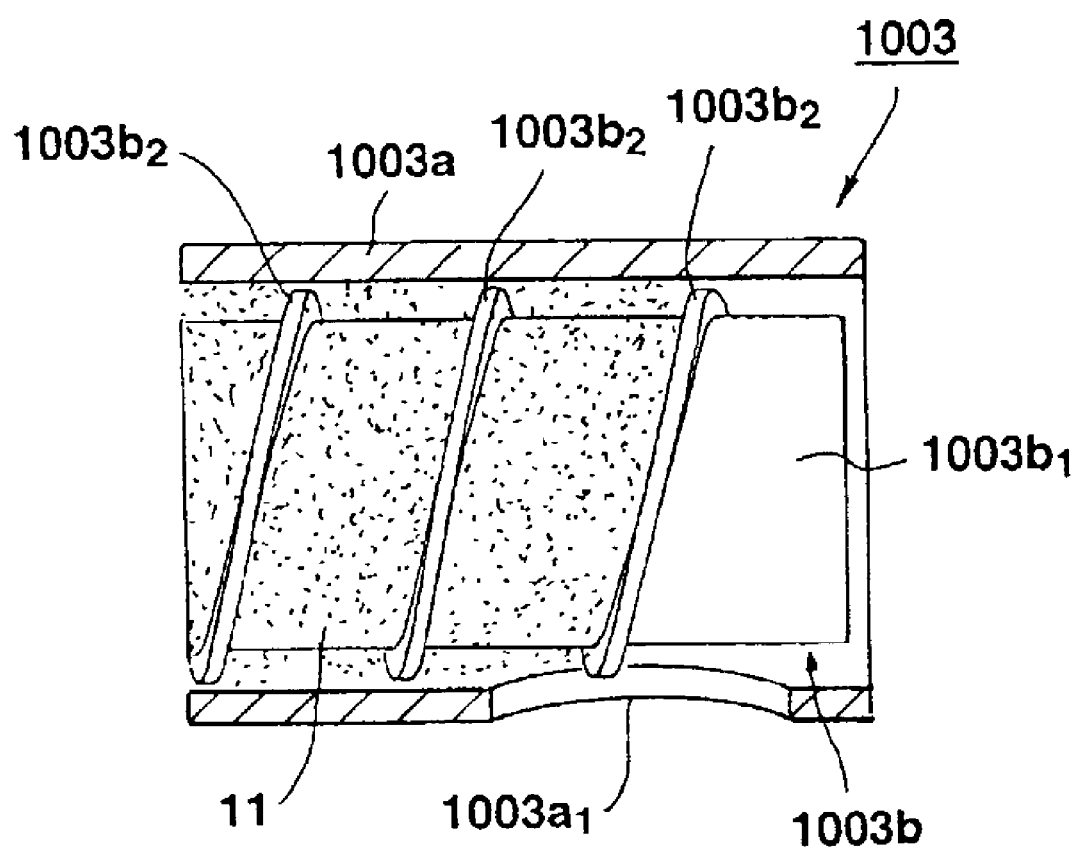

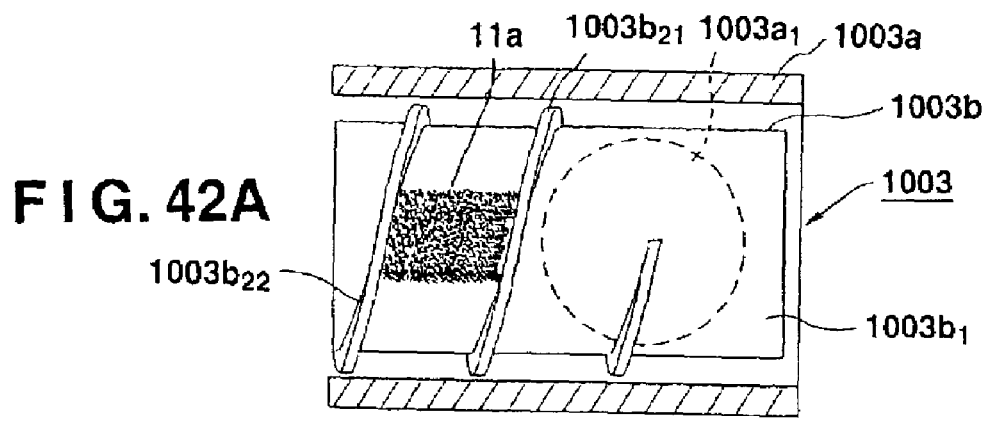
F I G. 42A
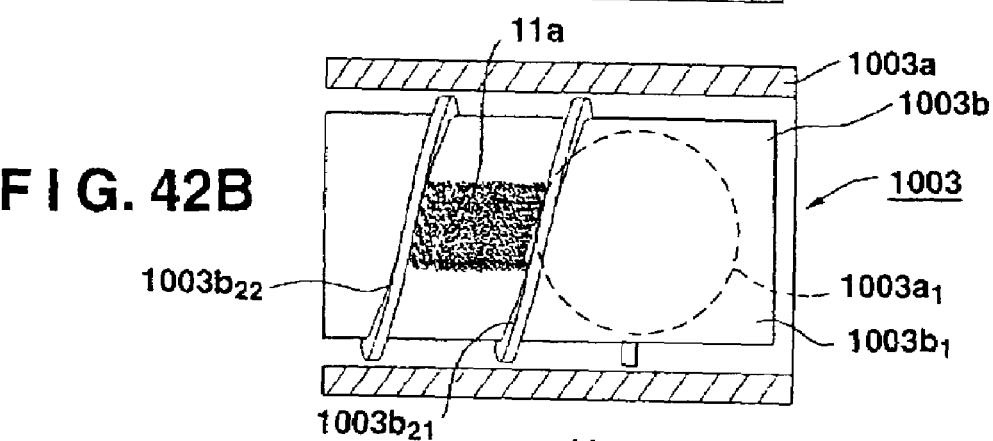
F I G. 42B
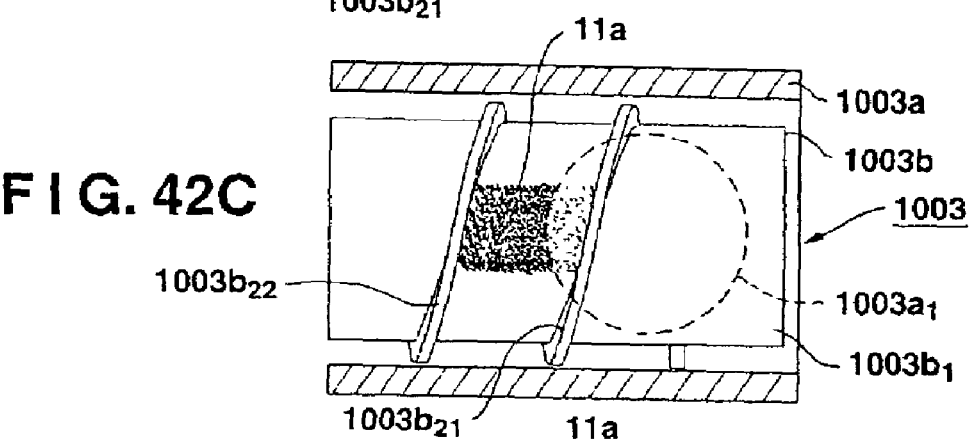
F I G. 42C
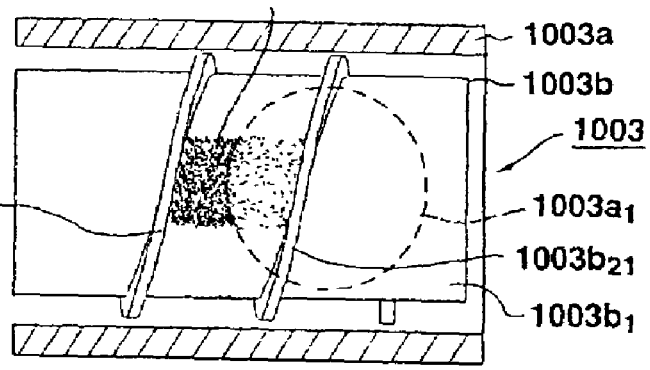
F I G. 42D

BIOMASS GASIFYCATION FURNACE AND SYSTEM FOR METHANOL SYNTHESIS USING GAS PRODUCED BY GASIFYING BIOMASS This application is the national phase under 35 U.S.C. §371 of PCT International Application No. PCT/JP01/01390 which has an International filing date of Feb. 26, 2001, which designated the United States of America and was not published in English.

TECHNICAL FIELD

The present invention relates to a biomass gasification furnace, and to a methanol synthesis system making use of a gas produced through biomass gasification.

BACKGROUND ART

The word biomass generally refers to substances of biological origin (e.g., agricultural products or by-products; lumber; plants; etc.) that can be utilized as an energy source or industrial raw material. Since biomass is produced by solar energy, and by the action of air, water, soil, or similar natural substances, it can be produced infinitely.

Fuel, methanol, and similar materials can be produced making use of the above-described biomass. Also, since biomass that exists in the form of waste can be utilized, a clean environment can be provided. Further, since newly produced biomass is grown through photosynthesis; i.e., fixation of $CO_2$, the concentration of $CO_2$ in the atmosphere is not increased.

Conventionally proposed methods for converting biomass into alcohol include, for example, the fermentation method and the hydrothermal degradation method. The former method, the fermentation method, requires installation of a tank for sugar components, whereas the hydrothermal degradation method involves the problems that high temperature and high pressure are required and yet yield is low. Moreover, another problem is that, considerable amounts of residue are generated from the input biomass, raising the problem of low biomass utilization.

Meanwhile, in the case in which biomass is gasified, a gasification furnace, such as a fixed-bed gasification furnace or a fluidized-bed gasification furnace, has heretofore been employed. However, since only the surface portions of granular biomass undergo reaction, and the reaction cannot proceed uniformly to the innermost portion of the granules, tar is generated, and the produced gas; i.e., the gas obtained through gasification, has a low $H_2$ content and low CO content. Therefore, the thus-produced gas cannot serve as a raw material for methanol synthesis. Moreover, the generated tar is deposited not only onto the inside wall of the furnace, but also onto the apparatuses, etc. installed on the downstream side of the furnace, inviting problematic maloperation of the furnace.

In order to prevent such problems, conventionally, oxygen is supplied in great amounts so as to effect combustion at high temperature. However, in this case, another problem is involved; a high-temperature zone of higher than 1,200° C. is formed at some portions, where gasification of biomass does not proceed successfully, providing large amounts of soot through combustion of biomass.

In view of the foregoing, an object of the present invention is to provide a biomass gasification furnace which promises clean, high-efficiency gasification, which contemplates complete gasification of biomass, and which is capable of producing a gas realizing a highly efficient methanol synthesis. Another object of the present invention is to provide a methanol synthesis system making use of the thus-produced gas.

DISCLOSURE OF THE INVENTION

A variety of modes of the gasification furnace of the present invention making use of biomass as a raw material will next be described.

A first mode is drawn to a biomass gasification furnace employing biomass as a raw material, characterized in that said furnace comprises means for feeding pulverized biomass having an average particle size (D) falling within a range of $0.05 \leq D \leq 5$ mm and combustion-oxidizing-agent-feeding means for feeding oxygen or a mixture of oxygen and steam serving as a combustion-oxidizing agent, and that gasification conditions include a furnace interior temperature of 700–1,200° C.

A second mode is drawn to a biomass gasification furnace in relation to the first mode, wherein the mol ratio of oxygen $[O_2]$/carbon [C] in the biomass gasification furnace falls within a range of $0.1 \leq O_2/C < 1.0$, and the mol ratio of steam $[H_2O]$/carbon [C] falls within a range of $1 \leq H_2O/C$.

A third mode is drawn to a biomass gasification furnace in relation to the first mode, wherein the internal pressure of the biomass gasification furnace is 1–30 atm, and gasification conditions include a superficial velocity of 0.1–5 m/s.

A fourth mode is drawn to a biomass gasification furnace in relation to the first mode, wherein the combustion-oxidizing agent is fed to a plurality of stages in the biomass gasification furnace.

A fifth mode is drawn to a biomass gasification furnace in relation to the first mode, wherein fossil fuel is fed into the biomass gasification furnace.

In the fifth mode, the fossil fuel may be coal.

A sixth mode is drawn to a biomass gasification furnace in relation to the first mode, wherein the biomass gasification furnace comprises a gas-purification unit for purifying a gas formed through gasification carried out in the biomass gasification furnace; and biomass and a combustion-oxidizing agent are fed such that the compositional ratio $H_2/CO$ of the generated gas approaches 2.

A seventh mode is drawn to a biomass gasification furnace in relation to the sixth mode, wherein the amount of oxygen derived from the combustion-oxidizing agent is such that heat generated during partial oxidation of biomass exceeds the heat that has been absorbed during decomposition of biomass.

In the above mode, the combustion-oxidizing agent may have an oxygen content of 3–15%.

An eighth mode is drawn to a biomass gasification furnace in relation to the sixth mode, wherein steam serving as the combustion-oxidizing agent is high-temperature steam of at least 300° C.

In the above mode, the high-temperature steam may be obtained through heat exchange with gas generated through gasification.

A ninth mode is drawn to a biomass gasification furnace in relation to the sixth mode, further comprising steam reforming means provided in the vicinity of an upper outlet of the biomass gasification furnace or on the downstream side of the gasification furnace.

In the above-described mode, the steam reforming means may reform the hydrocarbon contained in the produced gas into CO and $H_2$ by use of a nickel catalyst.

In the above mode, the steam reforming may be performed at 500° C. or higher.

A tenth mode is drawn to a biomass gasification furnace in relation to the first mode, wherein the biomass gsification furnace further comprises feeding means for feeding biomass provided at a top section of a gasification furnace main body, and an ash receiving section provided in a bottom section of the gasification furnace main body.

An eleventh mode is drawn to a biomass gasification furnace in relation to the tenth mode, wherein the biomass gasification furnace further comprises a gas discharge tube provided at a lower portion of a side wall of the gasification furnace main body so as to discharge gas produced through gasification.

A twelfth mode is drawn to a biomass gasification furnace in relation to the tenth mode, wherein the biomass gasification furnace further comprises hollow cylindrical gas-ash introducing means having a downwardly reduced diameter and provided on an inner wall surface of the gasification furnace in the vicinity of the upper section of the gas discharge tube of the gasification furnace.

A thirteenth mode is drawn to a biomass gasification furnace in relation to the eleventh mode, wherein the biomass gasification furnace further comprises cooling means on the side wall of the gasification furnace main body, and at least one soot removing means for blowing out deposits adhering onto an inner wall surface of the gasification furnace.

A fourteenth mode is drawn to a biomass gasification furnace in relation to the twelfth mode, wherein the biomass gasification furnace further comprises a water bath section provided at a bottom section of the biomass gasification furnace, and hollow cylindrical gas-ash introducing means having a downwardly reduced diameter, the end portion of the introducing means being dipped in the water bath section.

A fifteenth mode is drawn to a biomass gasification furnace in relation to the tenth mode, wherein the biomass gasification furnace further comprises a gas discharge tube for discharging produced gas provided at the center of the top section of the biomass gasification furnace, the gas discharge tube extending vertically such that a lower end portion of a predetermined length of the gas discharge tube is inserted into the interior of the gasification furnace with the lower-end opening of the gas discharge tube facing the interior of the furnace.

A sixteenth mode is drawn to a biomass gasification furnace in relation to the fifteenth mode, wherein the bottom section of the gasification furnace main body has a hollow cylindrical shape of downwardly reduced diameter, and the gasification furnace further comprises a water bath section provided at a bottom section thereof.

A seventeenth mode is drawn to a biomass gasification furnace in relation to the tenth mode, wherein the diameter of a lower half portion of the gasification furnace main body is slightly reduced as compared with the diameter of an upper half portion of the main body; a partition is provided vertically in the interior of the diameter-reduced portion of the gasification furnace main body, thereby forming a path for introducing produced gas and ash; the produced gas and ash are caused to pass through the path; and the produced gas is forced to turn at the frontal edge of the partition, thereby removing the ash and discharging the produced gas from the gas discharge tube for discharging the produced gas.

An eighteenth mode is drawn to a biomass gasification furnace in relation to the seventeenth mode, wherein the biomass gasification furnace further comprises a heat exchanger provided in the above-mentioned path so as to perform heat exchange with produced gas.

A nineteenth mode is drawn to a biomass gasification furnace combusting biomass so as to generate combustion gas and to gasify biomass by use of the combustion gas as a heat source, characterized in that a combustion space for combusting the biomass and a gasification space for gasifying the biomass are separated from each other; and a combustion gas feeding line for feeding, into the gasification space, the combustion gas generated in the combustion space is provided between the combustion space and the gasification space.

A twentieth mode is drawn to a biomass gasification furnace in relation to the nineteenth mode, wherein the combustion space and the gasification space are provided in separately disposed combustion and gasification chambers, respectively; a reaction tube is provided in the gasification chamber; the gasification space is provided in the reaction tube; a combustion gas feeding passage connected to the combustion gas feeding line is provided between the inside wall surface of the gasification chamber and the outside wall surface of the reaction tube; and perforations for uniformly feeding the combustion gas from the combustion gas feeding passage to the reaction tube are provided in the reaction tube.

A twenty-first mode is drawn to a biomass gasification furnace in relation to the nineteenth mode, wherein the combustion space and the gasification space are provided in separately disposed combustion and gasification chambers, respectively; a reaction tube is provided in the gasification chamber; the gasification space is provided in the reaction tube; and a combustion gas feeding passage connected to the combustion gas feeding line is provided between the inside wall surface of the gasification chamber and the outside wall surface of the reaction tube.

A twenty-second mode is drawn to a biomass gasification furnace in relation to the nineteenth mode, wherein the combustion space and the gasification space are provided in a single chamber in such a manner that the combustion space and the gasification space are separated from each other; a reaction tube is provided in the single chamber; the gasification space is provided in the reaction tube; a combustion gas feeding passage connected to the combustion gas feeding line is provided between the inside wall surface of the chamber and the outside wall surface of the reaction tube; and perforations for uniformly feeding the combustion gas from the combustion gas feeding passage to the reaction tube are provided in the reaction tube.

A twenty-third mode is drawn to a biomass gasification furnace in relation to the twentieth mode, wherein a line for feeding steam so as to prevent carbon formation and soot formation is provided in the combustion space.

A twenty-fourth mode is drawn to a biomass gasification furnace in relation to the twenty-first mode, wherein a line for feeding steam from which oxygen has been removed is provided in the gasification space.

A twenty-fifth mode is drawn to a biomass gasification furnace in relation to the twentieth mode, wherein heat recovery means and/or dust prevention means is provided in the combustion space.

A twenty-sixth mode is drawn to a biomass gasification furnace in relation to the twentieth mode, wherein a combustion gas exhaust line is provided in the combustion gas feeding passage and heat recovery means is provided in the combustion gas exhaust line.

A twenty-seventh mode is drawn to a biomass gasification furnace in relation to the twentieth mode, wherein a combustion gas exhaust line is provided in the combustion gas feeding passage, and means for recovering unreacted biomass for gasification is provided between the combustion gas exhaust line and the reaction tube.

A twenty-eighth mode is drawn to a biomass gasification furnace in relation to the twentieth mode, wherein a produced-gas exhaust line is provided in the gasification space and heat recovery means is provided in the produced-gas exhaust line.

A twenty-ninth mode is drawn to a biomass gasification furnace in relation to the twentieth mode, wherein the combustion chamber has an opening for feeding biomass for combustion, and the opening is provided with an opening and closing cap attached thereto such that the opening can be opened and closed.

A variety of modes for carrying out the gasification method of the present invention employing biomass as a raw material will next be described.

A thirtieth mode is drawn to a biomass gasification method employing biomass as a raw material, characterized by comprising feeding, to a biomass gasification furnace, pulverized biomass having an average particle size (D) falling within a range of $0.05 \leq D \leq 5$ mm and a mixture of air and steam or a mixture of oxygen and steam serving as a combustion-oxidizing agent; and employing gasification conditions including a mol ratio of oxygen $[O_2]$/carbon $[C]$ falling within a range of $0.1 \leq O_2/C < 1.0$, a mol ratio of steam $[H_2O]$/carbon $[C]$ falling within a range of $1 \leq H_2O/C$, and a furnace interior temperature of 700–1,200° C.

A thirty-first mode is drawn to a biomass gasification method in relation to the thirtieth mode, wherein the internal pressure of the biomass gasification furnace is 1–30 atm, and gasification conditions include a superficial velocity of 0.1–5 m/s.

A thirty-second mode is drawn to a biomass gasification method in relation to the thirtieth mode, wherein the combustion-oxidizing agent is fed to a plurality of stages in the biomass gasification furnace.

A thirty-third mode is drawn to a biomass gasification system characterized by comprising a gas purification unit for purifying gas generated through gasification performed in the biomass gasification furnace as recited in relation to the first mode and a gas turbine employing the resultant purified gas as a fuel.

A thirty-fourth mode is drawn to a biomass gasification method characterized in that a portion of biomass is combusted through partial combustion; the temperature of the interior of the gasification furnace is elevated by effectively utilizing heat of $CO_2$ produced during the course of chemical synthesis; and biomass is gasified while high-temperature steam is supplied.

A thirty-fifth mode is drawn to a biomass gasification method in relation to the thirty-fourth mode, wherein the hydrocarbon contained in the produced gas is steam-reformed to form CO and $H_2$, to thereby control the compositional ratio $H_2$/CO of the gas to approximately 2.

A variety of modes of the methanol synthesis system of the present invention employing biomass as a raw material will next be described.

A thirty-sixth mode is drawn to a methanol synthesis system characterized by comprising a gas purification unit for purifying gas generated through gasification performed in the biomass gasification furnace as recited in relation to the first mode, and a methanol synthesis unit for synthesizing methanol from $H_2$ and CO contained in the resultant purified gas.

A thirty-seventh mode is drawn to a methanol synthesis system in relation to the thirty-sixth mode, further comprising, on the upstream side of the methanol synthesis unit, a CO shift reaction unit for adjusting the compositional ratio of $H_2$ to CO gas contained in a gas.

A thirty-eighth mode is drawn to a methanol synthesis system in relation to the thirty-sixth mode, further comprising a carbon dioxide removal unit provided on the upstream side of the methanol synthesis unit.

In the above-described mode, carbon dioxide gas which has undergone removal of excess carbon dioxide may be employed as a carrier gas for feeding biomass into the biomass gasification furnace.

In the above-described mode, a discharge gas which has undergone recovery of methanol may be employed as a carrier gas for feeding biomass into the biomass gasification furnace.

In the above-described mode, a discharge gas which has undergone recovery of methanol may be fed into the biomass gasification furnace.

A thirty-ninth mode is drawn to a methanol synthesis system making use of biomass, characterized by comprising a gasification furnace as described in relation to the sixth mode, heat exchanging means for removing steam contained in purified gas, and a methanol synthesis unit for synthesizing methanol from cooled gas which has undergone heat exchange.

A fortieth mode is drawn to a methanol synthesis system making use of biomass, the system being as described in relation to the thirty-ninth mode, further comprising a carbon dioxide removal unit, provided on an upstream side of the methanol synthesis unit, for removing $CO_2$ in produced gas.

A forty-first mode is drawn to a methanol synthesis system making use of biomass, comprising a gasification furnace as recited in relation to the sixth mode; heat exchanging means for removing steam contained in purified gas; a methanol synthesis unit for synthesizing methanol from cooled gas which has undergone heat exchange, and a CO shift reaction unit for adjusting the compositional ratio of $H_2$ to CO gas contained in the purified gas.

A forty-second mode is drawn to a methanol synthesis system making use of biomass, the system being as described in relation to the forty-first mode, further comprising, on an upstream side of the methanol synthesis unit, a carbon dioxide removal unit for removing $CO_2$ in produced gas.

In the above-described mode, $CO_2$ from which excess carbon dioxide has been removed may be employed as a carrier gas for feeding biomass into the biomass gasification furnace.

In the above-described mode, the humidity and temperature of oxygen to be fed into the biomass gasification furnace may be elevated by use of water removed by the heat exchanging means.

In the above-described mode, a discharge gas which has undergone recovery of methanol may be employed as a carrier gas for feeding biomass into the biomass gasification furnace.

In the above-described mode, a discharge gas which has undergone recovery of methanol may be fed into the biomass gasification furnace.

In the above-described mode, a discharge gas which has undergone recovery of methanol may be employed as a fuel for a gas engine.

In the above-described mode, heat generated and recovered during production of methanol may be used in a gas turbine.

In the above-described mode, heat generated and recovered during production of methanol may be used for drying biomass.

A forty-third mode is drawn to a methanol synthesis system, wherein a biomass gasification system of the thirty-ninth mode is mounted on a base so as to allow conveyance of the system.

A forty-fourth mode is drawn to a methanol synthesis system, wherein a biomass gasification system of the thirty-ninth mode is mounted on a traveling carriage so as to enable transport of the system.

A forty-fifth mode is drawn to a methanol synthesis system making use of biomass, the system being as described in relation to the forty-first mode, wherein discharge water from the heat exchanging means is introduced into the methanol synthesis unit, so as to recover heat generated during the course of methanol synthesis, and subsequently, the heated water is introduced into the cooling means, to thereby recover heat from the produced gas, and the thus-obtained heated steam is fed into the biomass gasification furnace.

A forty-sixth mode is drawn to a methanol synthesis system making use of biomass, the system being as described in relation to the forty-fifth mode, wherein the heat exchanging means comprises water sprinkling means and alkaline water sprinkling means, and the discharge water after water sprinkling is used for recovering heat.

A forty-seventh mode is drawn to a methanol synthesis system making use of biomass, the system being as described in relation to the forty-fifth mode, further comprising an adsorption column or a guard column inserted between a booster unit and a regenerator and/or between the regenerator and the methanol synthesis unit.

A forty-eighth mode is drawn to a methanol synthesis system making use of biomass, the system being as described in relation to the forty-fifth mode, wherein a gas generated from the methanol synthesis unit is subjected to gas-liquid separation; $H_2$ contained in the separated gas is removed by means of a hydrogen separation unit; and the removed $H_2$ is fed back to a site on the upstream side of the regenerator.

A forty-ninth mode is drawn to a methanol synthesis system making use of biomass, the system being as described in relation to the forty-fifth mode, wherein the methanol synthesis unit is a synthesis column comprising a plurality of stages of catalyst layers, and at least two series of the synthesis columns are provided.

A fiftieth mode is drawn to a methanol synthesis system making use of biomass, the system being as described in relation to the forty-ninth mode, wherein the catalyst layer placed on an inlet side of the synthesis column serves as a guard column.

A variety of modes of the methanol synthesis method making use of biomass serving as a raw material will next be described.

A fifty-first mode is drawn to a methanol synthesis method making use of biomass characterized by synthesizing methanol through removal of $CO_2$ contained in the gas obtained through the gasification method of the thirty-fourth mode.

A fifty-second mode is drawn to a methanol synthesis method making use of biomass, characterized by adjusting, by means of a CO shift reaction unit, the compositional ratio of $H_2$ to CO gas of a gas obtained through the gasification method of the thirty-fourth mode, to thereby regulate the compositional ratio $H_2/CO$ of the gas to approximately 2.

In the above-described mode, $CO_2$ from which excess carbon dioxide has been removed may be employed as a carrier gas for feeding biomass into the biomass gasification furnace.

In the above-described mode, a discharge gas which has undergone recovery of methanol may be employed as a carrier gas for feeding biomass into the biomass gasification furnace.

In the above-described mode, a discharge gas which has undergone recovery of methanol may be fed to the biomass gasification furnace.

In the above-described mode, a discharge gas which has undergone recovery of methanol may be employed as a fuel for a gas engine.

A fifty-third mode is drawn to a methanol synthesis method making use of biomass, the method being as recited in relation to the fifty-first mode, wherein heat generated and recovered during the course of production of methanol is used in a gas turbine.

A fifty-fourth mode is drawn to a methanol synthesis method making use of biomass, the method being as recited in relation to the fifty-first mode, wherein the recovered heat generated during the course of production of methanol is utilized for drying biomass.

A fifty-fifth mode is drawn to a methanol synthesis method making use of biomass, characterized in that, by employing the methanol synthesis system of the forty-ninth mode, a first synthesis column and a second synthesis column are used alternately during synthesis of methanol, and that when one synthesis column is in use, among a plurality of stages of catalyst layers in the other synthesis column, the first-stage catalyst layer on a gas inlet side is removed, the second-stage catalyst layer is caused to serve as the first-stage layer, and a new additional catalyst layer is inserted so as to be placed at the position of the final stage.

A variety of modes of the coal gasification method of the present invention making use of biomass as a raw material will next be described.

A fifty-sixth mode is drawn to a coal gasification method characterized by comprising feeding biomass to a reductor of a coal gasification furnace including a combustor and the reductor or to a site on the downstream side of the reductor, and effecting gasification of coal and the biomass simultaneously.

A fifty-seventh mode is drawn to a coal gasification method as described in relation to the fifty-sixth mode, wherein the biomass is fed after being mixed with coal in advance.

A fifty-eighth mode is drawn to a coal gasification method as described in relation to the fifty-sixth mode, wherein the biomass and coal are fed through positions which face each other.

A fifty-ninth mode is drawn to a coal gasification method as described in relation to the fifty-seventh mode, wherein the biomass is fed through a position on a downstream side of a position through which the coal is fed.

A methanol synthesis system by employment of coal gasification making use of biomass as a raw material will next be described.

A sixtieth mode is drawn to a methanol synthesis system making use of biomass, characterized by comprising a gas purification unit for purifying a gas produced through the gasification method of the fifty-sixth mode, and a methanol synthesis unit for synthesizing methanol from the gas which has been purified.

A sixty-first mode is drawn to a methanol synthesis system making use of biomass, the system being as described in relation to the sixtieth mode, further comprising a steam reforming means for reforming hydrocarbons contained in the produced gas into CO and $H_2$, the reforming means being provided within a gasification furnace or at the outlet of the gasification furnace.

A sixty-second mode is drawn to a methanol synthesis system making use of biomass in relation to the sixtieth mode, further comprising a CO shift reaction unit for regulating the compositional ratio of $H_2$ to CO gas contained in the purified gas.

A sixty-third mode is drawn to a methanol synthesis system making use of biomass in relation to the sixtieth mode, further comprising, on the upstream side of the methanol synthesis unit, a carbon dioxide removing unit for removing $CO_2$ in the produced gas.

A sixty-fourth mode is drawn to a methanol synthesis system including a biomass gasification furnace employing a gas produced through combustion of biomass serving as a heat source for gasifying biomass and a methanol synthesis unit employing, for synthesizing methanol, a synthesis gas produced in the above-described biomass gasification furnace, characterized in that the biomass gasification furnace comprises a combustion space for combusting the biomass and a gasification space for gasifying the biomass, the spaces being provided separately, and a combustion gas feeding line for feeding the combustion gas from the combustion space to the gasification space is provided between the combustion space and the gasification space; and the methanol synthesis unit comprises a pressurizing chamber, a catalyst chamber, and a methanol recovery chamber, and operates such that the synthesis gas introduced from the biomass gasification furnace into the pressurizing chamber, the catalyst chamber, and the methanol recovery chamber is pressurized at a predetermined pressure, to thereby transform the synthesis gas into methanol through catalytic reaction in the catalyst chamber, the methanol is liquefied in the methanol recovery chamber, and the liquefied methanol is recovered and the residual gas is purged.

A sixty-fifth mode is drawn to a methanol synthesis system including a biomass gasification furnace, the system being as described in relation to the sixty-fourth mode, further comprising a storage tank for storing the synthesis gas from the biomass gasification furnace—the gas being stored therein during introduction of the synthesis gas, and synthesis, liquefaction, and recovery of methanol in the methanol synthesis unit of batch-type—between the biomass gasification furnace and the methanol synthesis unit.

A sixty-sixth mode is drawn to a methanol synthesis system including a biomass gasification furnace, the system being as described in relation to the sixty-fourth mode, wherein the catalyst chamber comprises heating means.

A sixty-seventh mode is drawn to a methanol synthesis system including a biomass gasification furnace, the system being as described in relation to the sixty-fourth mode, the methanol recovery chamber comprises cooling means.

A sixty-eighth mode is drawn to a methanol synthesis system including a biomass gasification furnace for producing a synthesis gas through combustion and thermal decomposition of biomass and a methanol synthesis unit for synthesizing methanol from the synthesis gas produced in the biomass gasification furnace, characterized in that the methanol synthesis unit comprises a pressurizing chamber, a catalyst chamber, and a methanol recovery chamber, and operates such that the synthesis gas introduced from the biomass gasification furnace into the pressurizing chamber, the catalyst chamber, and the methanol recovery chamber is pressurized at a predetermined pressure, the synthesis gas is transformed into methanol through catalytic reaction in the catalyst chamber, the methanol is liquefied in the methanol recovery chamber, and the liquefied methanol is recovered and the residual gas is purged.

A variety of modes for feeding biomass into a biomass gasification furnace of the present invention will next be described.

A sixty-ninth mode is drawn to a biomass feeding unit, which serves as feeding means for feeding biomass into a biomass gasification furnace, characterized by comprising a hollow cylindrical hopper for storing granular material, such as fibrous granular biomass obtained by finely pulverizing biomass, and a screw feeder disposed at a lower portion of the hopper and adapted to convey the granular material in a horizontal direction and to discharge the granular material to the outside through an outlet which is provided at the distal end portion of a casing of the screw feeder such that the outlet is opened downward, wherein the feeding unit further comprises stirring means for stirring the granular material contained in the hopper such that the granular material stored in the hopper is fed to the screw feeder.

A seventieth mode is drawn to a biomass feeding unit, which serves as feeding means for feeding biomass into a biomass gasification furnace, characterized by comprising a hollow cylindrical hopper for storing granular material, such as fibrous granular biomass obtained by finely pulverizing biomass, and a screw feeder disposed at a lower portion of the hopper and adapted to convey the granular material in a horizontal direction and to discharge the granular material to the outside through an outlet which is provided at the distal end portion of a casing of the screw feeder such that the outlet is opened downward, wherein the feeding unit further comprises stirring means for stirring the granular material contained in the hopper such that the granular material stored in the hopper is fed to the screw feeder; and on the side on which the base end portion of the screw feeder is present, the outlet provided at the distal end potion of the casing has a side of a straight line crossing the axis of the screw feeder.

A seventy-first mode is drawn to a biomass feeding unit as described in relation to the seventieth mode, wherein the straight line crosses the axial direction of the screw feeder at the right angle.

A seventy-second mode is drawn to a biomass feeding unit as described in relation to the seventieth mode, wherein the straight line is inclined in a direction opposite to the inclination direction of a screw flight of the screw feeder, with respect to a straight line which crosses the axial direction of the screw feeder at the right angle, and the inclination angle of the straight line is identical to the angle between the screw flight and the straight line which crosses the axial direction of the screw feeder at the right angle.

A seventy-third mode is drawn to a biomass feeding unit as described in relation to the seventieth mode, wherein a large-diameter portion having a size larger than that of the remaining portion is provided at the distal end portion of the casing along the axial direction of the screw feeder, and an outlet is provided on a lower surface of the large-diameter portion.

A seventy-fourth mode is drawn to a biomass feeding unit as described in relation to the seventieth mode, wherein a plurality of injection nozzles are radially provided at the distal end portion of the casing, and gas is injected through the nozzles to the granular material which has arrived as conveyed through the screw feeder while being compressed and constrained between adjacent walls of the screw flight of the screw feeder, to thereby eliminate compression and entanglement of the granular material and discharge the granular material downward through the outlet.

A seventy-fifth mode is drawn to a biomass feeding unit as described in relation to the seventieth mode, wherein a screw shaft of the screw feeder is formed of a hollow member, and a perforation penetrating the screw shaft from the outer circumferential surface to the interior thereof, or an injection nozzle utilizing the perforation, is provided between adjacent walls of the screw flight in the vicinity of the distal end portion of the screw feeder, and gas is injected through the perforation or injection nozzle to the granular material which has arrived as conveyed through the screw feeder while being compressed and constrained between adjacent walls of the screw flight of the screw feeder, to thereby eliminate compression and entanglement of the granular material and discharge the granular material downward through the outlet.

A seventy-sixth mode is drawn to a biomass feeding unit as described in relation to the seventieth mode, further comprising a fluidization cone for receiving the granular material discharged and falling through the outlet, and imparting a gyratory flow to the granular material to thereby eliminate entanglement of the granular material, and gas forming the gyratory flow is utilized as a carrier gas for feeding the granular material to a destination apparatus such as a gasification furnace.

A seventy-seventh mode is drawn to a biomass feeding unit as described in relation to the seventy-sixth mode, wherein the fluidization cone comprises stirring means for stirring the granular material received by the cone.

A seventy-eighth mode is drawn to a biomass feeding unit as described in relation to the seventy-fourth mode, further comprising a funnel-shaped portion for receiving the granular material discharged and falling through the outlet, in which the path of the granular material is gradually narrowed, and the granular material is introduced to a feeding line connected to a destination apparatus to which the granular material is fowarded, such as a gasification furnace, and a carrier gas for the granular material is supplied.

A seventy-ninth mode is drawn to a biomass feeding unit as described in relation to the seventieth mode, wherein relatively large pitches are provided between adjacent walls of the screw flight at the distal end portion of the screw shaft of the screw feeder, and relatively small pitches are provided between adjacent walls of the screw flight at the central portion of the screw shaft, which central portion is adjacent to the distal end portion.

An eightieth mode is drawn to a biomass feeding unit as described in relation to the seventieth mode, wherein pitches between adjacent walls of the screw flight of the screw shaft of the screw feeder are gradually reduced from the base portion on the hopper side to an intermediate portion at which the pitches are minimum, and the pitches are gradually increased from the intermediate portion to the distal end portion.

An eighty-first mode is drawn to a biomass feeding unit characterized by comprising a hollow cylindrical hopper for storing granular material such as fibrous granular biomass obtained by finely pulverizing biomass, the hopper including stirring means for stirring the granular material; and a screw feeder for conveying the granular material in a horizontal direction, the feeder being provided at the lower portion of the hopper, wherein the diameter of the distal end portion of the screw feeder is gradually reduced and the distal end thereof is connected to a feeding line having a small diameter; and gas is injected, at the distal end portion of the screw feeder, to the granular material which is compressed by and conveyed through the screw feeder, to thereby loosen compression and eliminate entanglement of particles of the granular material, and the resultant granular material is conveyed and fed, through the feeding line, by a carrier gas stream of the aforementioned gas to a destination apparatus such as a gasification furnace.

An eighty-second mode is drawn to a biomass feeding unit as described in relation to the eighty-first mode, wherein the gas for loosening compression and eliminating entanglement of the granular material and making a carrier gas stream is fed through a perforation or an injection nozzle utilizing the perforation which penetrates the screw shaft of the screw feeder and is provided between adjacent walls of a screw flight in the vicinity of the endmost portion of the screw shaft of the screw feeder formed of a hollow member.

An eighty-third mode is drawn to a biomass feeding unit as described in relation to the eighty-first mode, wherein the gas for loosening compression and eliminating entanglement of the granular biomass and making a carrier gas stream is fed through a plurality of injection nozzles radially provided at the distal end portion of a casing.

An eighty-fourth mode is drawn to a biomass feeding unit as described in relation to the eighty-first mode, wherein relatively large pitches are provided between adjacent walls of the screw flight at the distal end portion of the screw shaft of the screw feeder, and relatively small pitches are provided between adjacent walls of the screw flight at the central portion of the screw shaft, which central portion is adjacent to the distal end portion.

An eighty-fifth mode is drawn to a biomass feeding unit as described in relation to the eighty-first mode, wherein pitches between adjacent walls of the screw flight of the screw shaft of the screw feeder are gradually reduced from the base portion on the hopper side to an intermediate portion at which the pitches are minimum, and the pitches are gradually increased from the intermediate portion to the distal end portion.

BRIEF DESCRIPTION OF THE DRAWINGS

FIG. 12 is a schematic diagram of a methanol synthesis system employing a biomass gasification furnace according to the twelfth embodiment.

FIG. 30 is a schematic diagram of an alternative coal gasification furnace according to the twenty-third embodiment.

FIG. 41 is a longitudinal cross-sectional view showing the tip portion of a screw feeder according to a conventional art.

FIG. 42 conceptionally depicts the state in which finely pulverized biomass is conveyed and discharged by means of the screw feeder shown in FIG. 41.

FIG. 43 conceptionally depicts a biomass feeding unit according to the thirtieth embodiment, wherein

FIG. 46 depicts a biomass feeding unit according to the thirty-first embodiment, wherein

FIG. 47 depicts an example tip portion of the screw feeder according to the thirty-first embodiment, wherein

BEST MODES FOR CARRYING OUT THE INVENTION

With reference to the accompanying drawings, the best modes for carrying out the present invention will next be described in more detail, which should not be construed as limiting the invention thereto.

[First Embodiment]

A first embodiment of the present invention will be described with reference to FIG. 1.

Figure 1:
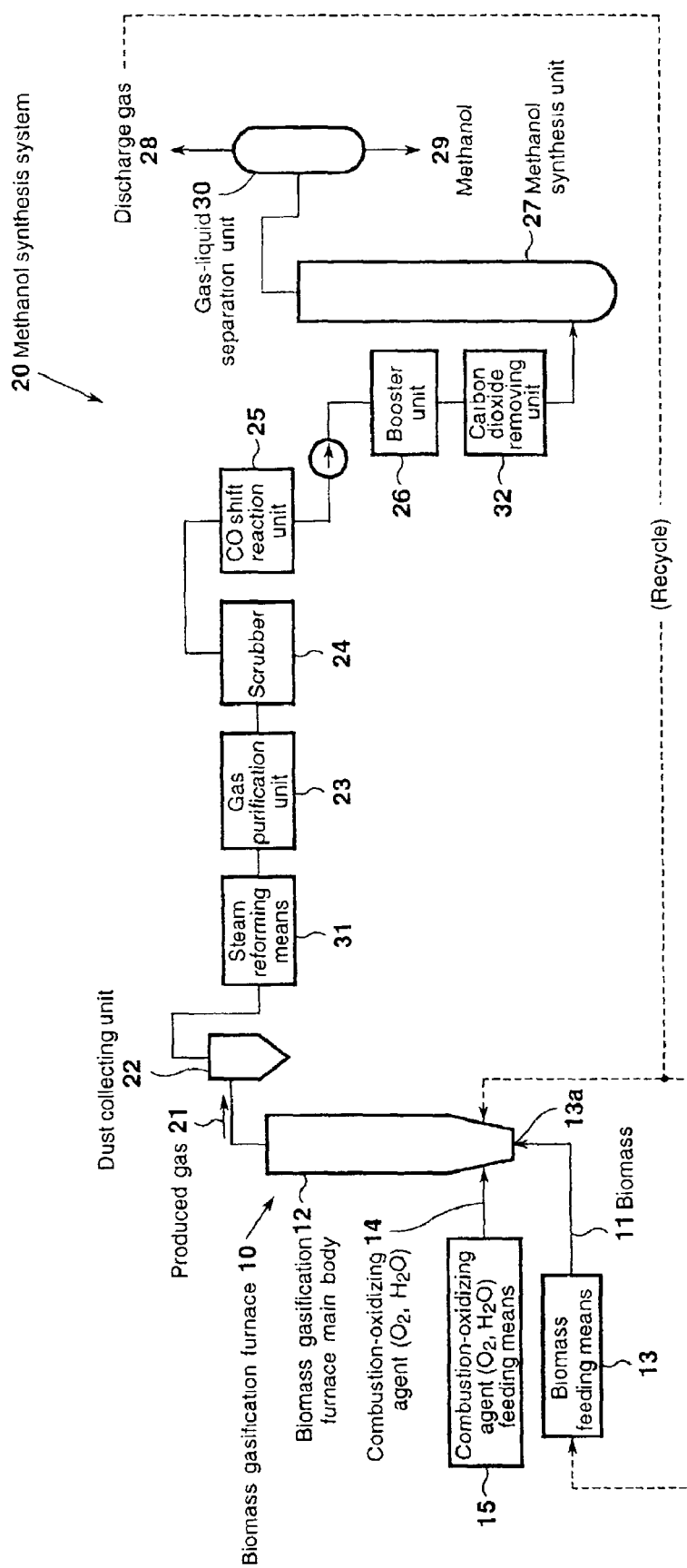
FIG. 1 is a schematic diagram of a methanol synthesis system employing a biomass gasification furnace according to the first embodiment.

FIG. 1 shows a schematic view of a methanol synthesis system employing a biomass gasification furnace according to the present embodiment.

As shown in FIG. 1, a biomass gasification furnace 10 according to the present embodiment is an entrained-bed-type gasification furnace comprising a biomass feeding means 13 for feeding biomass 11 to a furnace main body 12, and combustion-oxidizing agent feeding means 15 which is located above the biomass feeding means 13 (i.e.; on the downstream side of the furnace) and feeds a combustion-oxidizing agent (e.g.; $O_2$ or $H_2O$) 14 comprising oxygen or a mixture of oxygen and steam to the furnace main body 12.

The biomass 11 to be fed to the furnace main body 12 of the present invention is preferably a produced or waste biomass in pulverized, dried form.

As used herein, the word biomass refers to biological resources (such as agricultural products and by-products, lumber, and plants) which can be utilized as energy sources or industrial raw materials. Examples of such biological resources include sweet sorghum, nepiergrass, and spirulina.

In the present invention, the average particle size (D) of the aforementioned granular biomass 11 preferably falls within a range of $0.05 \leq D \leq 5$ mm. The reason is as follows. When the average particle size is 0.05 mm or less, effect of pulverizing biomass becomes disadvantageously poor, whereas when the average particle size is in excess of 5 mm, biomass cannot be satisfactorily combusted to the innermost portion, and reaction is not accelerated, to thereby make high-efficiency gasification difficult.

In the present invention, the combustion-oxidizing agent 14 to be fed to the biomass gasification furnace is preferably a mixture of air and steam or a mixture of oxygen and steam.

The aforementioned combustion-oxidizing agent 14 is added in such an amount that the mol ratio of oxygen $[O_2]$/carbon $[C]$ is controlled to $0.1 \leq O_2/C$, preferably $0.1 \leq O_2/C < 1.0$ (particularly preferably $0.2 \leq O_2/C < 0.5$) and the mol ratio of steam $[H_2O]$/carbon $[C]$ is controlled to $1 \leq H_2O/C$ (particularly preferably $2 \leq H_2O/C \leq 6$).

This is because when the aforementioned mol ratios fall within the above ranges, the supply of steam and oxygen enables satisfactory gasification through partial oxidation, to thereby increase the amounts of $H_2$ and CO in the produced gas with formation of soot and tar in negligible amounts.

The interior temperature of the biomass gasification furnace main body 12, which is one factor of gasification conditions, is preferably controlled to 700–1,200° C.

This is because when the interior temperature of the furnace is lower than 700° C., thermal decomposition of biomass is disadvantageously poor, whereas when the interior temperature is in excess of 1,200° C., soot is undesirably generated through self combustion of biomass.

The internal pressure of the biomass gasification furnace main body 12 is preferably controlled to 1–30 atm.

The reason for this is, although a pressure of approximately 80 atm is preferred for the direct synthesis of methanol (or dimethyl ether, etc.), such a high pressure calls for a pressure-resistant structure of the gasification furnace, disadvantageously elevating production costs.

An internal pressure of approximately 30 atm is preferred, because the superficial velocity can be lowered and the size of the equipment can be reduced.

The superficial velocity in the biomass gasification furnace main body 12, which is one factor of gasification conditions, is preferably controlled to 0.1–5 m/s.

This is because a superficial velocity equal to or lower than 0.1 m/s prolongs the residence time in the furnace, resulting in disadvantageously excessive combustion, whereas a superficial velocity in excess of 5 m/s prevents complete combustion/thermal decomposition, to thereby fail to attain satisfactory gasification.

In order to attain optimal conveyance of pulverized biomass, the particle size of the biomass is more preferably taken into consideration. When the average particle size of the biomass is 0.1–1 mm, a superficial velocity of 0.4–1 m/s is particularly preferred, and when the average particle size is 1–5 mm, a superficial velocity of 1–5 m/s is preferred.

The biomass gasification furnace according to the present invention provides clean gas without formation of soot or similar substances, because the furnace gasifies biomass efficiently through partial oxidation.

The aforementioned produced gas is purified by a gas purification means, and thereafter, can directly serve as a fuel gas for a gas turbine.

Furthermore, by adjusting the compositional ratio of Hz to CO gas contained in the produced gas, the produced gas can be used also as a gas for producing a substance such as methanol (or dimethyl ether).

Hereinbelow, a system in which the thus-obtained gas is employed for methanol synthesis will be described.

<Methanol Synthesis System (1)>

As shown in FIG. 1, a methanol synthesis system 20 for synthesizing methanol employing the above-described biomass gasification furnace comprises a dust collecting unit 22 for removing soot and dust from the produced gas generated in the furnace main body 12 of the biomass gasification furnace 10; a purification unit 23 for purifying the dust-removed gas; a scrubber 24 for removing steam from the purified gas; a CO shift reaction unit 25 for regulating the compositional ratio of $H_2$ to CO gas in the thus-obtained gas; a booster unit 26 for elevating pressure of the gas; a methanol synthesis unit 27 for producing methanol ($CH_3OH$) from $H_2$ and $CO_2$ contained in the pressurized gas; and a gas-liquid separation unit 30 for separating discharge gas 28 and methanol 29.

The biomass 11 which has been fed into the furnace main body 12 of the gasification furnace 10 is partially combusted by use of the combustion-oxidizing agent 14, and combusted under the aforementioned predetermined conditions, to thereby improve efficiency of biomass gasification. The thus-produced gas 21 is subjected to dust removal in the dust collecting unit 22, and then, transferred to the scrubber 24 for removal of steam from the gas, where the gas is cooled, and simultaneously, steam is removed. Subsequently, the $H_2$ content is elevated in the CO shift reaction unit, and the pressure of the gas is elevated by means of the booster 26 to a pressure suitable for methanol synthesis. The pressurized gas is transferred to the methanol synthesis unit 27, where methanol is produced. Thereafter, discharge gas 28 and methanol 29 are separated.

Since $CH_4$ remains in the above discharge gas 28, the gas can be recycled by being fed to the entrained-bed-type gasification furnace 10 again.

The compositional ratio $H_2/CO$ of the gas produced through the aforementioned gasification of biomass will be discussed hereinbelow.

The composition of biomass is represented by the $C_mH_2O_n$ (m=1.0–1.5, n=0.7–1.1). However, for the purpose of convenience, the composition is represented simply by $CH_2O$ and is employed in the following description.

In general, methanol synthesis proceeds in accordance with the following reaction scheme:

$$CO + 2H_2 \rightarrow CH_3OH \tag{1}$$

In a conventional synthesis employing methane ($CH_4$) serving as natural gas, the reaction proceeds as follows:

$$CH_4 + H_2O \rightarrow CO + 3H_2 \tag{2}$$

In a conventional synthesis employing fossil fuel (coal), the reaction proceeds as follows:

$$CH_2 + H_2O \rightarrow CO + 2H_2 \tag{3}$$

Generally, when biomass is just simply gasified, the reaction proceeds as follows:

$$CH_2O \rightarrow CO + H_2 \quad (4),$$

and the $H_2/CO$ ratio never exceeds 2.

In order to solve this problem, in the present invention, a combustion-oxidizing agent 14 is introduced into a furnace, to thereby cause partial combustion ($CO + 1/2O_2 \rightarrow CO_2$), and the produced heat is used. $CO_2$ is removed in a subsequent step, to thereby enhance the $[H_2]/[CO]$ ratio.

Since the aforementioned reaction is endothermic, the reaction must be carried out while heating. However, since heating of solid biomass from the outside is difficult, gasification through partial combustion is employed.

As used herein, the term "partial combustion" refers to a mode of combustion in which a portion of biomass serving as fuel is subjected to combustion with a stoichiometrically insufficient amount of oxidizing agent (air or oxygen), so as to reserve a combustible gas of uncombusted fuel.

In order to promote partial oxidation reaction, thermal decomposition, and gasification reaction, biomass is finely pulverized so as to increase the reaction surface area. According to the present invention, this can be attained by adjusting the average particle size (D) of the granular biomass 11 to $0.05 \leq D \leq 5$ mm.

Provided that biomass is represented by $CH_2O$, the basic reactions of the biomass are as follows.

$$CH_2O \rightarrow CO + H_2 \quad (5) \text{ [endothermic reaction]}$$

$$CH_2O + 1/2O_2 \rightarrow CO_2 + H_2 \quad (6) \text{ [exothermic reaction]}$$

If the above reactions are achieved, a $H_2/CO$ ratio of 2 or more, which is required for methanol synthesis, can be attained.

Heat of formation of the above-described reactions at 25° C. is:

for reaction; −26.4+27.7=+1.3 Kcal (5) [endothermic reaction] and for reaction; −94+27.7=−66.3 Kcal (6) [exothermic reaction].

Thus, the overall reaction is exothermic.

In the case in which $CH_2O$ is completely combusted ($CH_2O + O_2 \rightarrow CO_2 + H_2O$), the heat of formation is −124.3 (exothermic).

If the above-described reactions (5) and (6) were changed to a complete combustion, the heat of formation would be as follows.

−124.3×2≈250 Kcal

Accordingly, in the overall reaction of (5) and (6):

−65.3/−250≈0.26, which indicates a ratio of about ¼ being justified to attain an ideal combustion.

However, the above-described reaction generates less heat than combustion reaction does. Thus, the temperature of the reaction field rises only to 450–500° C. (≈0.26×1, 800–1,900° C.), resulting in a prolonged reaction time.

In order to maintain a combustion field at 800–1,000° C. which allows the reaction to proceed, separate addition of high-temperature vapor at approximately 400–500° C. is required.

To meet this requirement, a high-temperature steam (about 400–500° C.) which has been obtained through heat exchange of the heat of high temperature gas produced in the gasification furnace main body 12 is introduced separately.

The above-described gasification system utilizing the vapor and oxygen gas in combination is an ideal reaction system. However, an actual reaction system yields, other than CO and $H_2$, approximately 7–8% hydrocarbons such as $CH_4$, $C_2H_4$—$C_2H_6$, $C_3H_6$—, tar, and soot.

Hydrocarbons such as the aforementioned $CH_4$ can be converted to CO and $H_2$ through steam reforming at a temperature equal to or greater than 550° C. (suitably 900° C.±100° C.) in the presence of steam and a nickel catalyst.

The $H_2$ obtained from the steam reforming can serve as a raw material for methanol synthesis as described above.

In other words, by adding a steam reforming means to a gasification system in which steam and oxygen are used in combination, CO and $H_2$ can be produced.

Thus, tar and soot, which are basically carbon-containing substances, can also undergo steam reforming if sufficient residence time is provided.

Specifically, steam reforming of substances such as tar and soot is performed by means of a steam reforming means 31 comprising a catalyst (honeycomb radiation converter bearing a Ni catalyst thereon) placed between the dust collecting unit 22 and the purification unit 23, to thereby yield C and $H_2$.

When the biomass reaction proceeds as shown by reaction schemes (5) and (6), $CO_2$ is contained in the produced gas as a result of the employment of internally generated heat.

$CO_2$ can also be used for methanol synthesis in the presence of a metallic catalyst such as Cu, Zn, or Cr, according to the following reaction formula (7):

$$CO_2 + 3H_2 \rightarrow CH_3OH + H_2O \quad (7).$$

However, this formula contemplates only the balance among CO, $CO_2$, and $H_2$ in the produced gas, and unnecessary $CO_2$ merely expands the reaction system.

Thus, in order to improve the percent methanol recovery, excess $CO_2$ is preferably removed from the system in a contacting manner by use of a $CO_2$ removing unit provided for removing $CO_2$, such as an amine-based wet $CO_2$ removing unit, in the final stage of the reaction system.

For this purpose, as shown in FIG. 1, a carbon dioxide removing unit 32 for removing $CO_2$ is interposed between the booster unit 26 and the methanol synthesis unit 27, to thereby remove excess $CO_2$.

According to the present embodiment, not limiting the invention thereto, the carbon dioxide removing unit 32 is interposed between the booster unit 26 and the methanol synthesis unit 27, to thereby remove $CO_2$. Alternatively, the carbon dioxide removing unit 32 may be provided on the upstream side of the booster unit 26, to thereby remove $CO_2$ in advance, and the resultant gas is pressurized by the booster unit 26.

Thus, through removal of excess $CO_2$, the gas serving as a raw material for methanol production and to be introduced into the methanol synthesis unit 27 has a composition of CO and $2H_2$, to thereby proceed methanol synthesis effectively, resulting in a yield of methanol of about 60% based on the biomass which has been supplied.

When a steam reforming means 31 is provided, the above-described CO shift reaction unit 25 for generating $H_2$ can be omitted, because the amount of $H_2$ increases during the gasification step.

A portion of the thus-separated and thus-removed $CO_2$ can be utilized as a carrier gas of the biomass feeding means 13. Thus, introduction of unnecessary $N_2$ into the furnace can be prevented, when a carrier medium such as air is used.

[Second Embodiment]

<Methanol Synthesis System (2)>

A second methanol synthesis system according of the present invention will next be described.

Components having the same functions as those in the first synthesis system are denoted by the same reference numerals, and repeated descriptions of such components are omitted.

Figure 2:
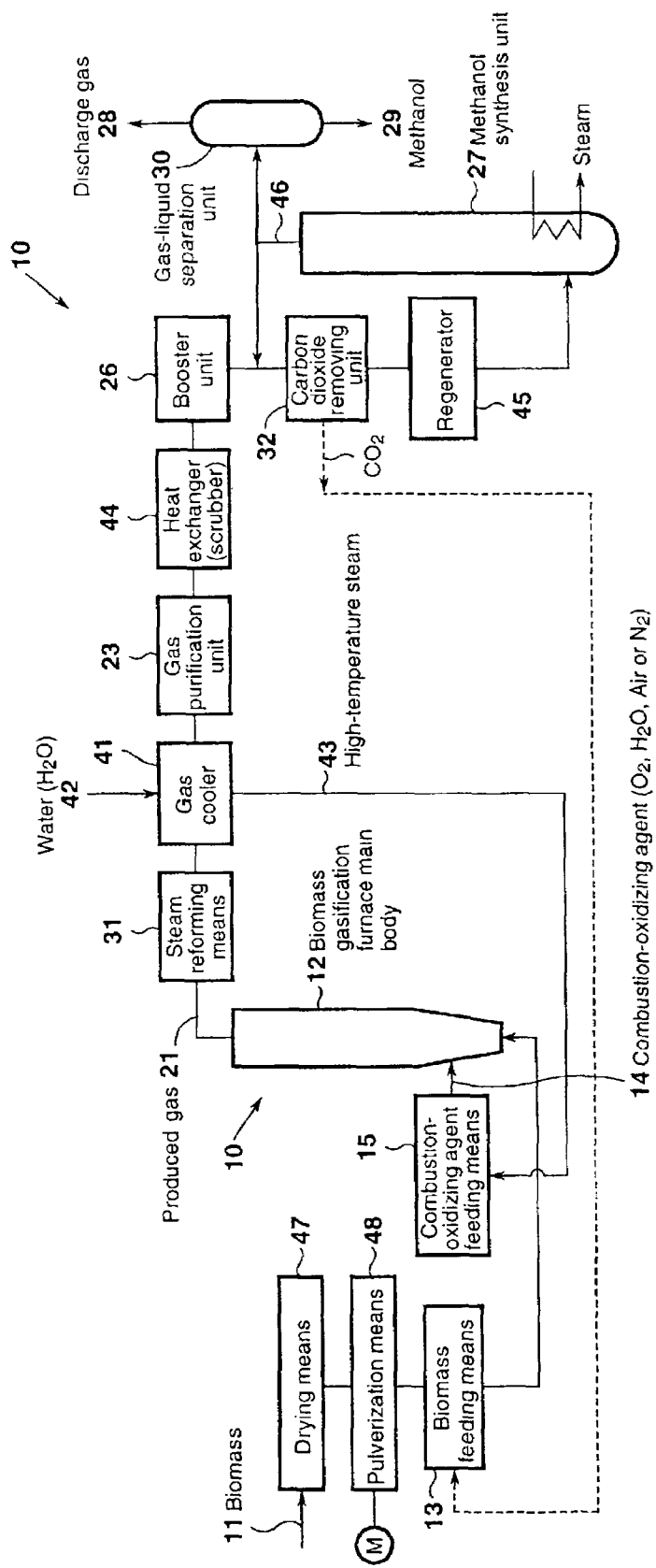
FIG. 2 is a schematic diagram of a methanol synthesis system employing a biomass gasification furnace according to the second embodiment.

FIG. 2 shows a schematic diagram of a methanol synthesis system making use of biomass comprising a biomass gasification system employing a biomass gasification furnace according to the present embodiment.

As shown in FIG. 2, the biomass gasification system according to the second embodiment comprises a biomass gasification furnace 10 for performing gasification utilizing biomass ($CH_2O$) 11 and a combustion-oxidizing agent 14 fed to the furnace, to thereby form gases such as $H_2$ and CO; steam reforming means 31 for reforming, in the presence of a nickel catalyst, hydrocarbon such as $CH_4$ contained in a produced gas 21 obtained through gasification in the biomass gasification furnace 10; a cooler 41 for cooling a gas reformed by means of the steam reforming means 31; heat-exchanging means (not illustrated) which is installed in the cooler 41 and generates high-temperature steam 43 through heat exchange with water 42 supplied from the outside; and a gas purification unit 23 for purifying the cooled produced gas; a heat exchanger 44 for removing steam from the gas which has been purified by means of the purification unit 23; a booster unit 26 for elevating the pressure of the gas; a carbon dioxide removing unit 32 for removing $CO_2$ contained in the pressurized gas; a regenerator 45 for heating the carbon-dioxide-removed gas to a temperature suitable for methanol production; a methanol synthesis unit 27 for producing methanol ($CH_3OH$) from $2H_2$ and CO contained in the gas; and a gas-liquid separation unit 30 for separating the produced gas 46 obtained by means of the methanol synthesis unit 27 into methanol 29 and discharge gas 28.

In the biomass gasification furnace 10 according to the second embodiment, biomass 11 is introduced to a biomass feeding means 13 for feeding biomass into a furnace main body 12, and steam 43 whose temperature is elevated by use of the aforementioned heat-exchanging means is introduced into combustion-oxidizing agent feeding means 15, to thereby supply high-temperature steam to the biomass gasification furnace 10.

Preferably, the biomass 11 to be fed to the furnace main body 12 according to the present invention is produced or waste biomass, and is dried by drying means 47, followed by pulverization to a predetermined particle size by a pulverization means 48.

In the methanol synthesis system according to the present embodiment, the formed gas from which carbon dioxide gas has been removed by means of a carbon dioxide removing unit 32 is heated by a regenerator 45 for heating the carbon-dioxide-removed formed gas so as to raise the temperature of the $CO_2$-removed formed gas to a temperature suitable for methanol synthesis, to thereby enhance the efficiency of methanol synthesis.

In the above-described methanol synthesis system, biomass 11 is dried in advance in the biomass gasification furnace 10 for gasifying biomass serving as a raw material; then pulverized to a predetermined particle size; and fed into the furnace main body 12. In such an operation, the biomass 11 is gasified through partial combustion at low temperature with $O_2$ in an amount ¼ the amount for the ideal combustion, while the heat attributed to $CO_2$ generated during the course of chemical synthesis is effectively utilized, to thereby elevate the interior temperature of the gasification furnace. In addition, high-temperature steam 43 is supplied from the outside, to thereby to maintain the interior temperature of the furnace at approximately 900° C., leading to proceed desirable gasification.

Although hydrocarbon such as $CH_4$ is generated in the formed gas 21, the hydrocarbon is reformed into CO and $H_2$ by means of the steam reforming means 31 provided on the outlet side of the gasification furnace, to thereby attain a gas composition suitable for methanol synthesis.

$CO_2$, which is unnecessary for synthesizing methanol, is removed to the outside by means of the carbon dioxide removing unit 32, to thereby attain a considerably ideal gas composition, wherein CO and $H_2$ serving as essential components for methanol synthesis are contained and the $H_2/CO$ ratio is becomes $2<(H_2/CO)$. Moreover, the CO2-removed formed gas is heated by means of the regenerator 45 to a temperature suitable for methanol synthesis, thereby enhancing the efficiency of methanol synthesis.

Thus, by effective use of the biomass 11, a clean gas for methanol synthesis containing no generated soot or similar substances is obtained. The gas enhances methanol synthesis efficiency, and approximate 60% the biomass 11 is converted to methanol fuel.

[Third Embodiment]

<Methanol Synthesis System (3)>

A third embodiment of the present invention will next be described with reference to FIG. 3.

Figure 3:
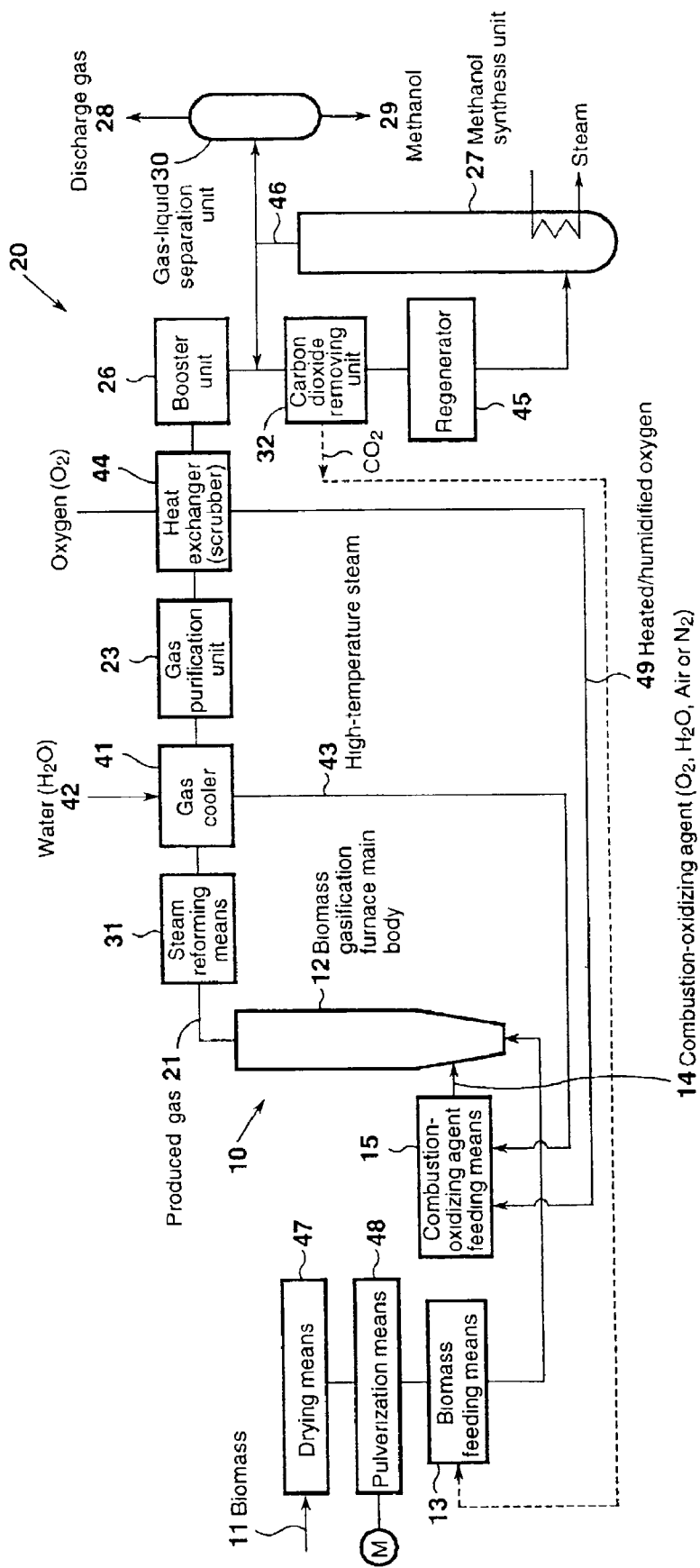
FIG. 3 is a schematic diagram of a methanol synthesis system employing a biomass gasification furnace according to the third embodiment.

FIG. 3 is a schematic diagram of a methanol synthesis system making use of a gas produced through gasification performed in a biomass gasification furnace according to the third embodiment.

Components having the same functions as those in the aforementioned methanol synthesis system are denoted by the same reference numerals, and repeated descriptions of such components are omitted.

In the biomass gasification system according to this embodiment, as shown in FIG. 3, unnecessary steam removed by means of the aforementioned heat exchanger 44 is used for heating and humidifying oxygen serving as a combustion-oxidizing agent 14 to be fed into the furnace main body 12 of the gasification furnace 10.

No particular limitation is imposed on the means for heating and humidifying oxygen, and an indirect heat exchange method, which includes bubbling oxygen through heat-recovered water provided from an indirect heat exchanging means or a similar means, may be employed.

The thus-heated/humidified oxygen 49 is fed to the biomass gasification furnace 1Z via the combustion-oxidizing agent feeding means 15, to thereby enhance efficiency of biomass gasification reaction. Thus, latent heat of low-temperature steam at about 50° C. which has been obtained by means of the heat exchanger 44 can be effectively recovered.

[Fourth Embodiment]

<Methanol Synthesis System (4)>

A fourth embodiment of the present invention will be described with reference to FIG. 4.

Figure 4:
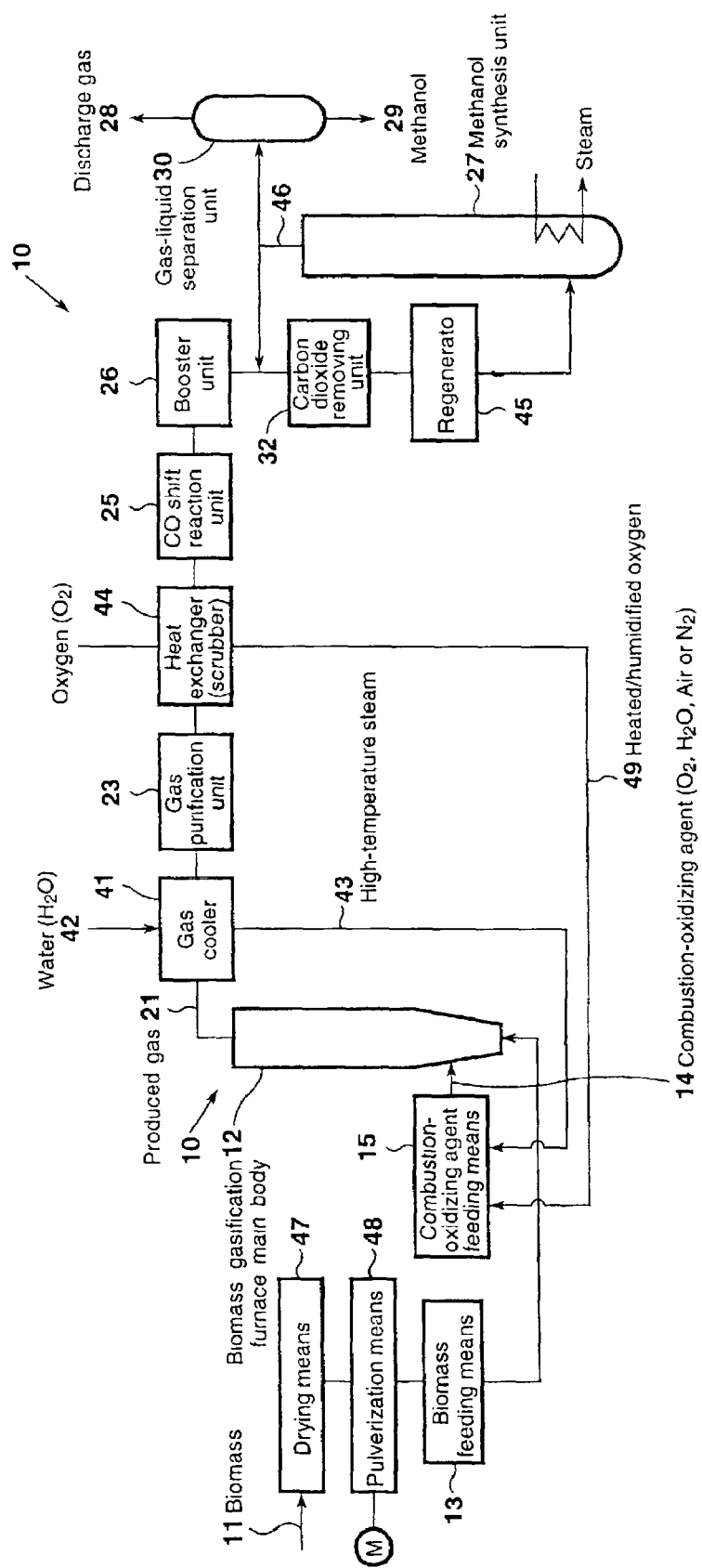
FIG. 4 is a schematic diagram of a methanol synthesis system employing a biomass gasification furnace according to the fourth embodiment.

FIG. 4 is a schematic diagram of a methanol synthesis system employing a biomass gasification furnace according to the present embodiment.

Components having the same functions as those in the aforementioned methanol synthesis system are denoted by the same reference numerals, and repeated descriptions of such components are omitted.

As shown in FIG. 4, the biomass gasification system according to this embodiment comprises a biomass gasification furnace 10 for gasifying fed biomass 11; a gas purification unit 23 for purifying a gas 21 produced through gasification in the biomass gasification furnace 10 and cooled by means of a cooler 41; a heat exchanger 44 for removing steam from the purified gas; a CO shift reaction unit 25 for adjusting the compositional ratio of $H_2$ to CO gas of the cooled gas; a booster unit 26 for elevating the pressure of the gas; a carbon dioxide removing unit 32 for removing $CO_2$ contained in the gas to the outside; a regenerator 45 for heating the carbon-dioxide-removed, pressurized gas to a temperature for methanol production; a methanol synthesis unit 27 for producing methanol ($CH_3OH$) from $H_2$ and CO contained in the gas; and a gas-liquid separation unit 30 for separating the synthesized gas 46 obtained by means of the methanol synthesis unit 27 into methanol 29 and discharge gas 28.

In the aforementioned embodiment, $CH_4$ contained in the gas produced through gasification is reformed into $H_2$ and CO by employment of a steam reforming means 31. However, in this embodiment, $H_2$ required for the methanol synthesis is produced by the CO shift reaction unit 25, instead of the steam reforming means 31. Although $CO_2$ is generated in the aforementioned CO shift reaction unit 25, excess $CO_2$ is removed from the reaction system to the outside by means of the aforementioned carbon dioxide removing unit 32.

As described in connection to the aforementioned embodiment, $CO_2$ removed by the carbon dioxide removing unit 32 may be used as a gas for carrying biomass 11. In addition, oxygen serving as a combustion-oxidizing agent 14 may also be heated and humidified by means of the high-temperature steam 43 provided from the cooler 41.

[Fifth Embodiment]

<Methanol Synthesis System (5)>

A fifth embodiment of the present invention will be described with reference to FIG. 5.

Figure 5:
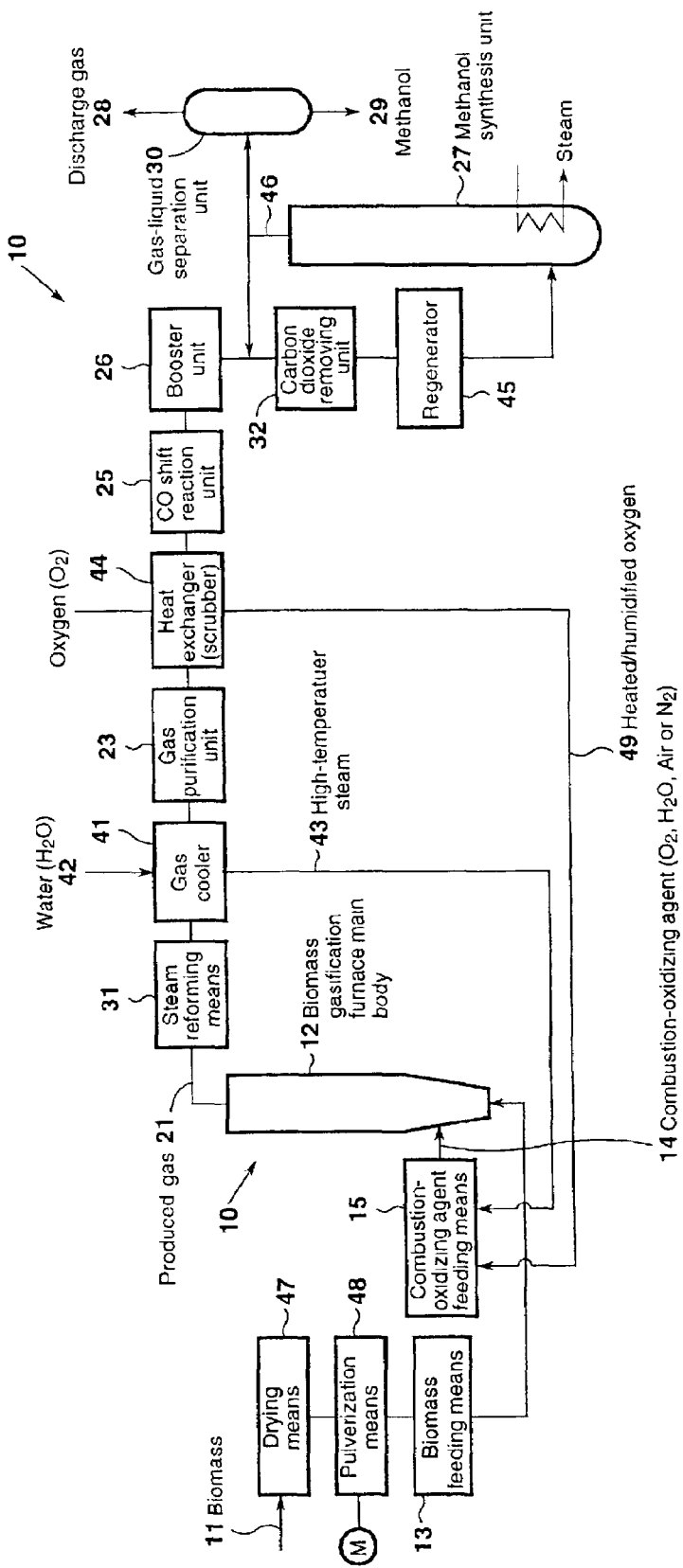
FIG. 5 is a schematic diagram of a methanol synthesis system employing a biomass gasification furnace according to the fifth embodiment.

FIG. 5 is a schematic diagram of a methanol synthesis system making use of a gas produced through gasification performed in a biomass gasification furnace according to the fifth embodiment.

As shown in FIG. 5, the methanol synthesis system according to the present embodiment comprises a biomass gasification furnace 10 for gasifying biomass 11 fed into the furnace; a steam reforming means 31 for reforming, in the presence of a nickel catalyst, hydrocarbons such as $CH_4$ contained in the gas 21 produced through gasification in the biomass gasification furnace 10; a cooler 41 for cooling the gas reformed by the steam reforming means 31; a gas purification unit 23 for purifying the gas cooled by the cooler 41; a heat exchanger 44 for removing steam contained in the purified gas; a CO shift reaction unit 25 for regulating the compositional ratio of $H_2$ to CO gas contained in the cooled gas; a booster unit 26 for pressurizing the resultant gas; a carbon dioxide removing unit 32 for removing to the outside $CO_2$ contained in the gas; a regenerator 45 for heating the pressurized/carbon-dioxide-removed gas to a temperature suitable for methanol production; a methanol synthesis unit 27 for producing methanol ($CH_2OH$) from $H_2$ and CO contained in the gas; and a gas-liquid separation unit 30 for separating the gas 46 synthesized by the methanol synthesis unit 27 into discharge gas 28 and methanol 29.

In the aforementioned first and other embodiments, $CH_4$ contained in the gas produced through gasification is reformed into $H_2$ and CO by employment of the steam reforming means 31. However, in this embodiment, a larger amount of Hz, required for methanol synthesis, is obtained through employment of the CO shift reaction unit 25 in combination with the steam reforming means. Although the CO shift reaction unit 25 generates $CO_2$, excess $CO_2$ is separated by the aforementioned carbon dioxide removing unit 32.

As described in connection with the aforementioned embodiment, $CO_2$ removed by the carbon dioxide removing unit 32 may be used as a carrier gas for the biomass 11. In addition, oxygen to be fed as the combustion-oxidizing agent 14 may also be heated and humidified by the heat exchanger 44.

[Sixth Embodiment]

<Methanol Synthesis System (6)>

A sixth embodiment of the present invention will next be described with reference to FIG. 6.

Figure 6:
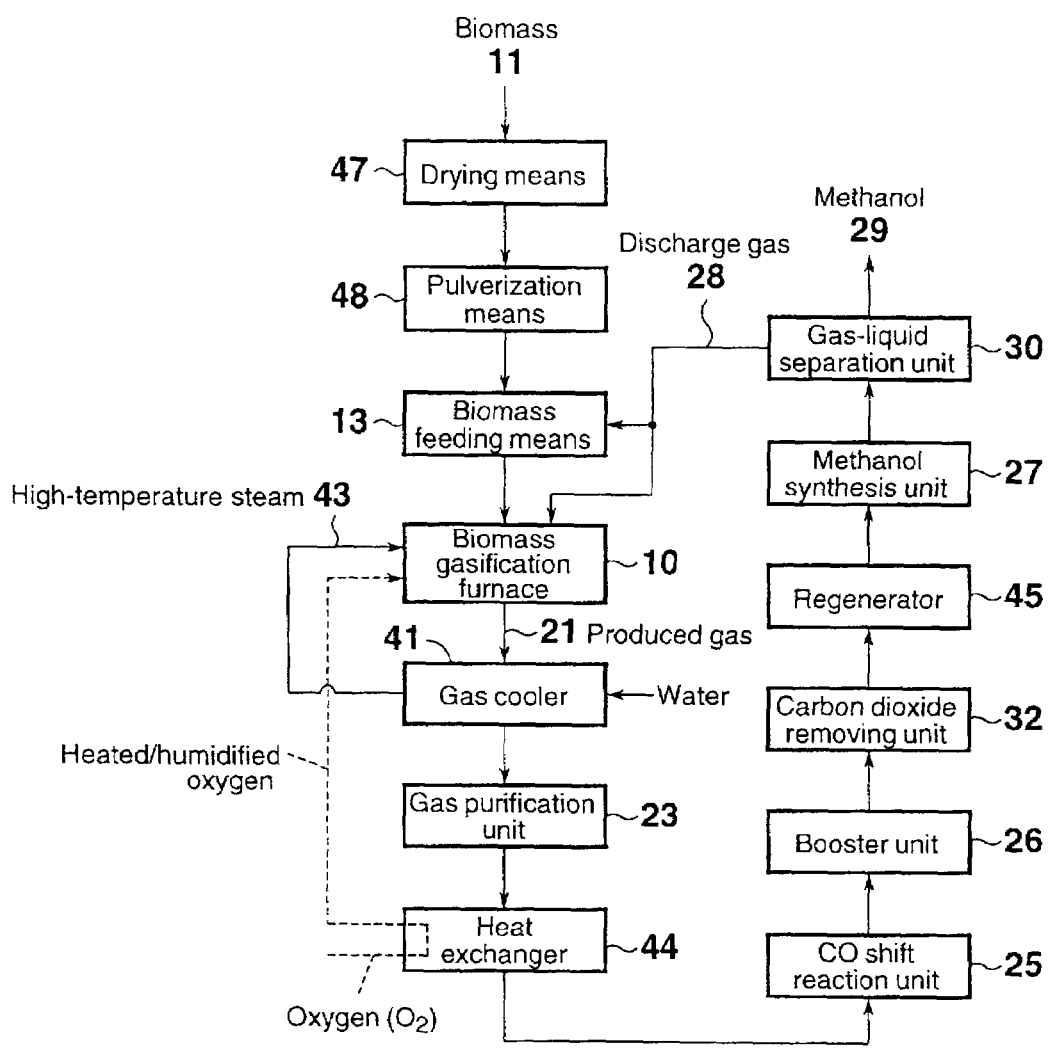
FIG. 6 Is a schematic diagram of a methanol synthesis system employing a biomass gasification furnace according to the sixth embodiment.

FIG. 6 is a schematic diagram of a methanol synthesis system making use of a gas produced through gasification performed in a biomass gasification furnace according to the sixth embodiment.

As shown in FIG. 6, the methanol synthesis system according to the sixth embodiment comprises a biomass gasification furnace 10 for gasifying biomass 11 fed into the furnace; a gas purification unit 23 for purifying gas 21 produced through gasification in the biomass gasification furnace 10 and cooled by a cooler 41; a heat exchanger 44 for removing steam contained in the purified gas; a CO shift reaction unit 25 for regulating the compositional ratio of $H_2$ to CO gas contained in the cooled gas; a booster unit 26 for pressurizing the gas; a carbon dioxide removing unit 32 for removing $CO_2$ contained in the gas to the outside the system; a regenerator 45 for heating the pressurized, carbon-dioxide-removed gas to a temperature suitable for methanol production; a methanol synthesis unit 27 for producing methanol ($CH_3OH$) from $H_2$ and CO contained in the gas; and a gas-liquid separation unit 30 for separating the synthesized gas into discharge gas 28 and methanol 29. In this gasification system, residual $CH_4$ contained in the discharge gas 28 separated by the gas-liquid separation unit 30 is recirculated into the biomass gasification furnace 10.

Thus, heat generated through combustion of the residual $CH_4$ in the discharge gas 28 can be utilized for partial oxidation, and the generated $CO_2$ is removed by means of the carbon dioxide removing unit 32. Since the composition of the gas for methanol synthesis remains constant by removing generated $CO_2$ by means of the carbon dioxide removing unit 32, methanol synthesis in the methanol synthesis unit 27 can be performed steadily.

The aforementioned discharge gas 28 yielded through gas-liquid separation may be effectively employed as a carrier gas for carrying the granular biomass 11 to the biomass gasification furnace 10, thereby feeding the biomass into the furnace.

The aforementioned discharge gas 28 can be used for driving a gas engine so as to effectively serve in the system as a power source for various equipment, such as a pulverizer for biomass, and an oxygen production unit for producing oxygen.

[Seventh Embodiment]

<Methanol Synthesis System (7)>

A seventh embodiment of the present invention will next be described with reference to FIG. 7.

Figure 7:
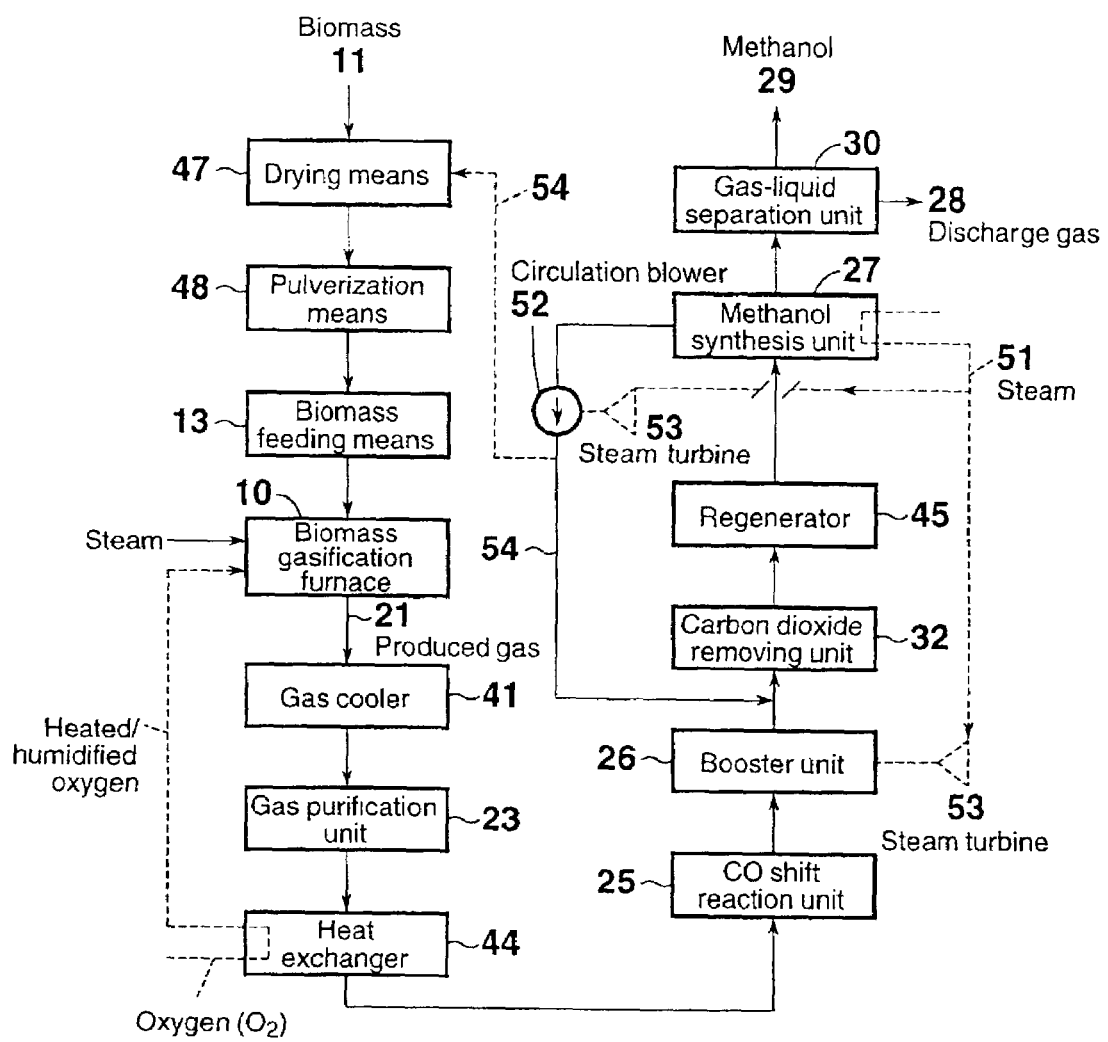
FIG. 7 is a schematic diagram of a methanol synthesis system employing a biomass gasification furnace according to the seventh embodiment.

FIG. 7 is a schematic diagram of a methanol synthesis system making use of a gas produced through gasification performed in a biomass gasification furnace according to the seventh embodiment.

As shown in FIG. 7, the methanol synthesis system according to the seventh embodiment comprises a biomass gasification furnace 10 for gasifying biomass 11 fed into the furnace; a gas purification unit 23 for purifying the gas 21 produced through gasification in the biomass gasification furnace 10 and cooled by a cooler 41; a heat exchanger 44 for removing steam contained in the purified gas; a CO shift reaction unit 25 for regulating the compositional ratio of $H_2$ to CO gas contained in the cooled gas; a booster unit 26 for pressurizing the gas; a carbon dioxide removing unit 32 for removing $CO_2$ contained in the gas to the outside of the system; a regenerator 45 for heating the pressurized gas to a temperature suitable for methanol production; a methanol synthesis unit 27 for producing methanol ($CH_3OH$) from $H_2$ and CO contained in the gas; and a gas-liquid separation unit 30 for separating synthesized gas into discharge gas 28 and methanol 29. In this system, a steam turbine 53, serving as a power sources for units such as a circulation blower 52 and the booster unit, is driven by use of steam 51 produced by recovering heat generated from methanol synthesis performed in the methanol synthesis unit 27.

The reaction carried out in the aforementioned methanol synthesis unit 27 is exothermic, and the thus-generated heat is used, attaining effective heat utilization in the system.

In addition, a portion of gas, contained in the methanol synthesis unit 27, is recycled to a site on the upstream side of the carbon dioxide removing unit 32 by means of the circulation blower 52, so as to enhance the efficiency of the synthesis. A portion of the recycled gas 54 can be employed in the drying means 47 as a gas for drying biomass 11.

[Eighth Embodiment]

<Methanol Synthesis System (8)>

An eighth embodiment of the present invention will next be described with reference to FIG. 8.

Figure 8:
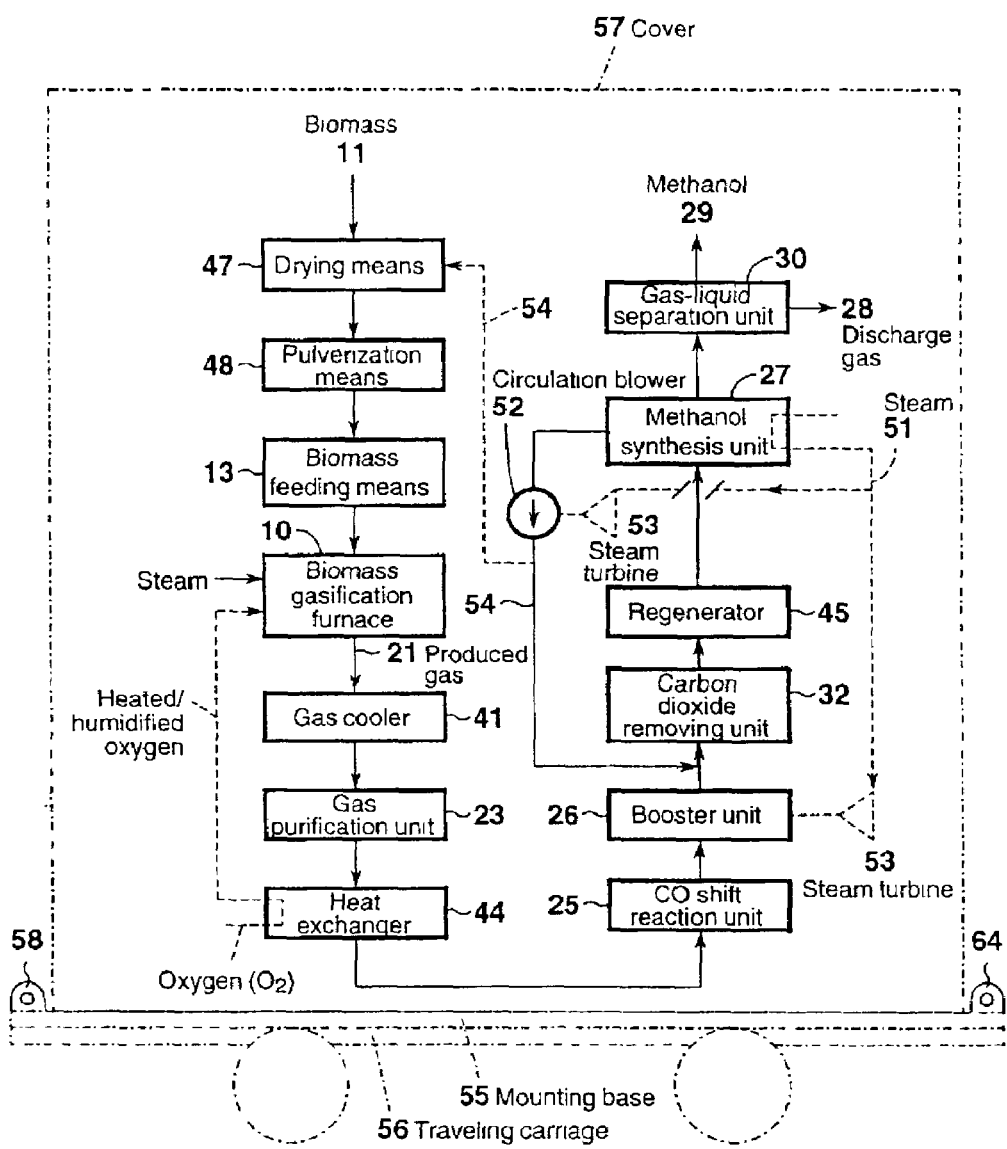
FIG. 8 is a schematic diagram of a methanol synthesis system employing a biomass gasification furnace according to the eighth embodiment.

FIG. 8 is a schematic diagram of a methanol synthesis system making use of a gas produced through gasification performed in a biomass gasification furnace according to the eighth embodiment.

As shown in FIG. 8, the biomass gasification system according to the seventh embodiment is mounted on a mounting base 55; or the entirety of the system mounted on the mounting base 55 is mounted on a traveling carriage 56; or the entirety of the system is mounted directly on the traveling carriage 56, so as to make the system movable.

As shown in FIG. 8, the entire system is mounted on the mounting base 55. The entirety mounting base 55 may be covered with a cover 57 so as to protect the apparatus therein. In order to move or transfer the system by suspending the same by means of a crane or similar means, lifting lugs 58 may be attached to the four corners of the mounting base 55, further enhancing operability.

Furthermore, by mounting the entire system on the traveling carriage 56, a movable system can be attained. The traveling carriage 56 may be equipped with wheels for towing by a tractor, or the traveling carriage 56 is equipped with driving means, to thereby make the system a self-moving biomass gasification system.

Alternatively, the system mounted on the mounting base 55 may be mounted on the traveling carriage 56 so as to transfer the system.

According to the present embodiment, the dimensions of the biomass gasification system can be considerably reduced as compared with a conventional technique. Therefore, the system can be suspended by means of a crane or a similar means; can be moved or towed by conveying means; or can move itself to an arbitrary site, attaining excellent transportability.

Thus, the system is capable of being transferred to the site where biomass is produced or waste is collected, to thereby gasify the biomass and produce methanol at the site.

Such transportability according to the eighth embodiment may be similarly imparted to the systems according to the aforementioned embodiments as well as the systems described hereinafter.

[Ninth Embodiment]

<Methanol Synthesis System (9)>

A ninth embodiment of the present invention will be described with reference to FIG. 9.

Figure 9:
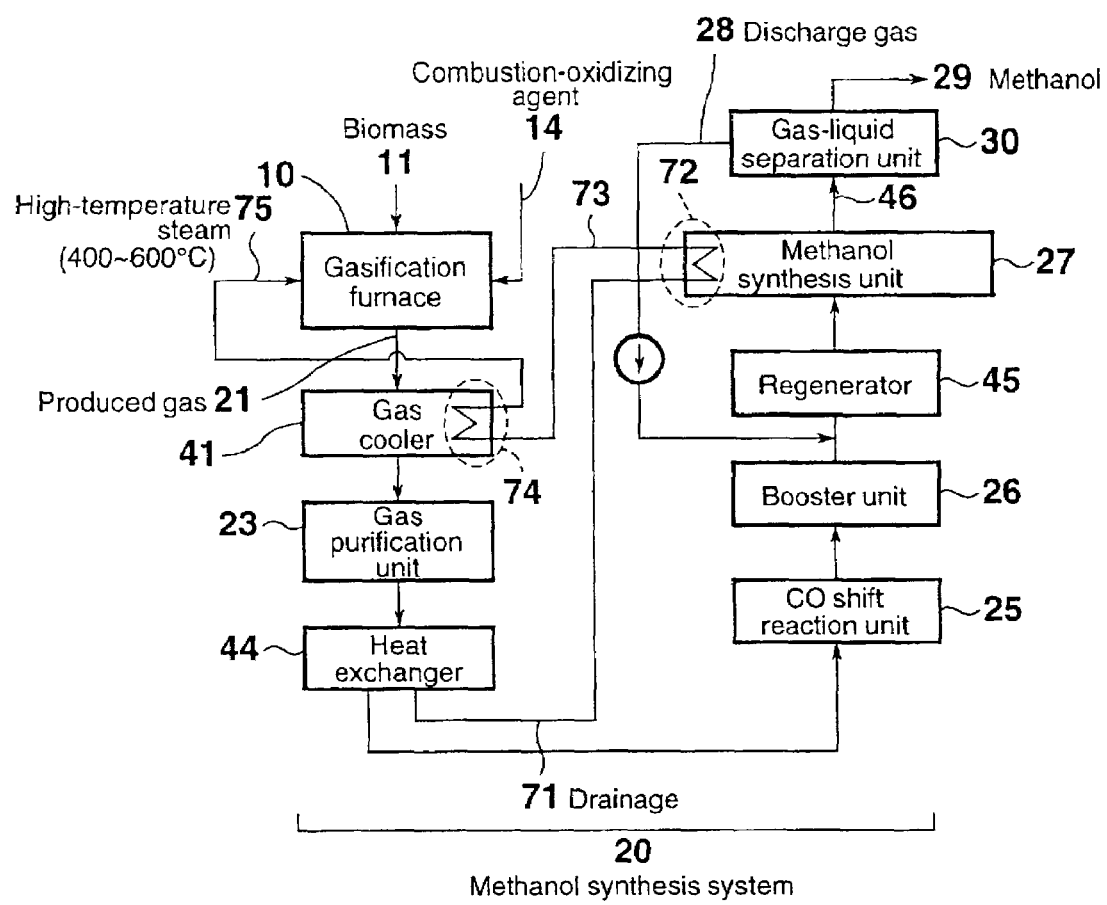
FIG. 9 is a schematic diagram of a methanol synthesis system employing a biomass gasification furnace according to the ninth embodiment.

FIG. 9 is a schematic diagram of a methanol synthesis system making use of a gas produced through gasification performed in a biomass gasification furnace according to the ninth embodiment.

As shown in FIG. 9, the methanol synthesis system according to the ninth embodiment comprises a biomass gasification furnace 10 for gasifying biomass 11 fed thereto; a gas purification unit 23 for purifying gas 21 produced through gasification in the gasification furnace 10 and cooled by means of a cooler 41; a heat exchanger 44 for removing steam from the purified gas; a CO shift reaction unit 25 for regulating the compositional ratio of $H_2$ to CO gas contained in the cooled gas; a booster unit 26 for elevating the pressure of the gas; a regenerator 45 for elevating the temperature of the pressurized gas to a temperature suitable for methanol synthesis; a methanol synthesis unit 27 for producing methanol ($CH_3OH$) from $H_2$ and CO contained in the gas; and a gas-liquid separation unit 30 for separating, from the synthesis gas, a discharge gas 28 and methanol 29. In this methanol synthesis system, the heat of reaction (approximately 300° C.) generated from the catalytic reaction in the methanol synthesis unit 27 is exchanged by water 71 discharged from the heat exchanger 44 in a first heat exchanger 72 provided inside the methanol synthesis unit 27.

Subsequently, the steam 73 having heat-exchanged is introduced into the cooler 41 for cooling the gas 21 produced from the gasification furnace 10, so as to recover the heat from high-temperature produced gas (e.g.; approximately 900° C.) through heat exchange in a second heat exchanger 74 provided inside the cooler 41. The thus-obtained high-temperature (400–600° C.) steam 75 is fed to the biomass gasification furnace 10.

The high-temperature steam 75 obtained in the system can be utilized as a component of the combustion-oxidizing agent 14, to thereby enhance efficiency of the methanol synthesis system employing biomass.

[Tenth Embodiment]

<Methanol Synthesis System (10)>

A tenth embodiment will next be described with reference to FIG. 10.

Figure 10:
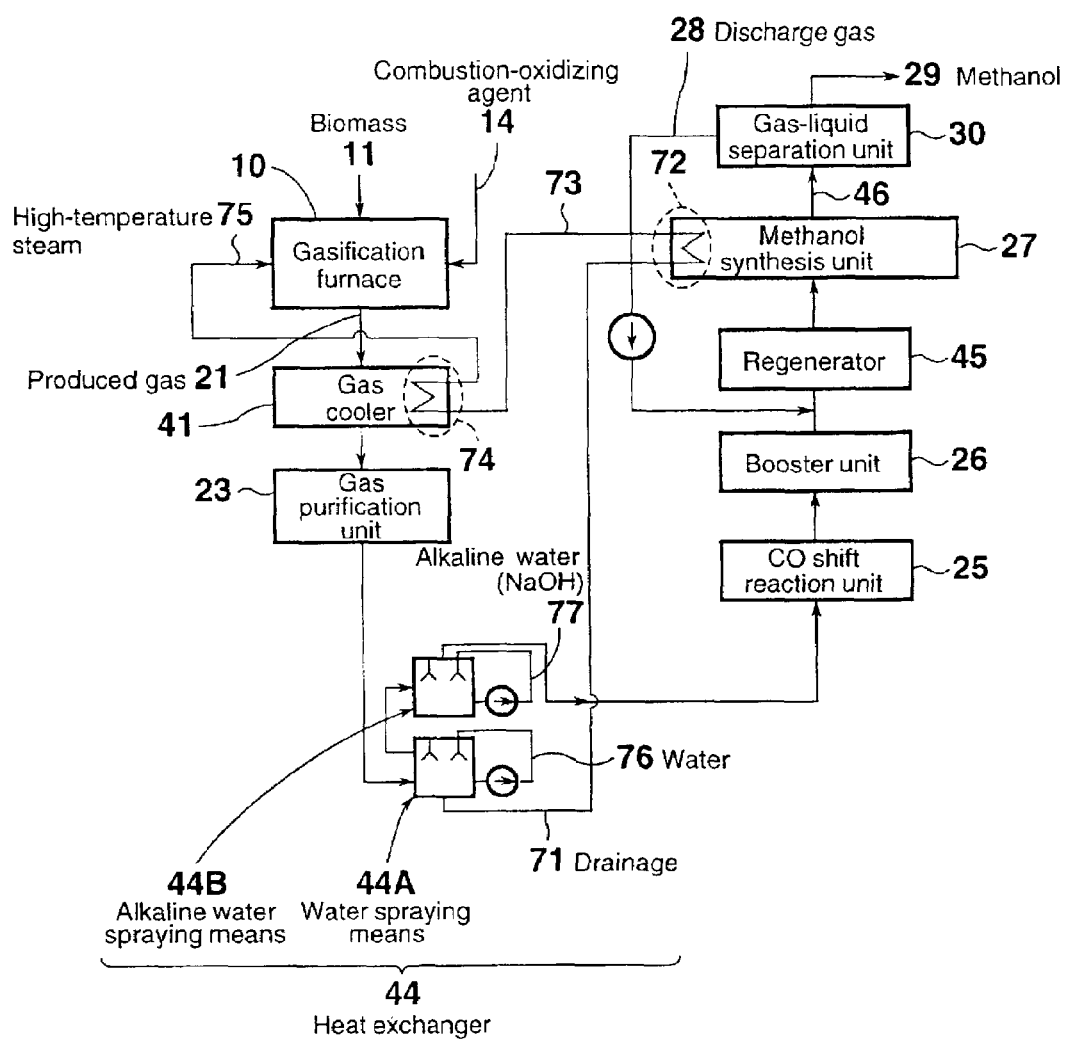
FIG. 10 is a schematic diagram of a methanol synthesis system employing a biomass gasification furnace according to the tenth embodiment.

FIG. 10 is a schematic diagram of a methanol synthesis system making use of a gas produced through gasification performed in a biomass gasification furnace according to the tenth embodiment.

Components having the same functions as those in the aforementioned methanol synthesis system are denoted by the same reference numerals, and repeated descriptions of such components are omitted.

As shown in FIG. 10, in the methanol synthesis system according to the tenth embodiment, the heat exchanger 44 for cooling the gas purified by the gas purification unit 26 and for removing moisture in the gas, comprises a water sprinkling means 44A for sprinkling water 76; and an alkaline water sprinkling means 44B for sprinkling alkaline solution 77 (e.g., NaOH). Heat recovery is carried out in a manner similar to that employed in the ninth embodiment, employing discharge water 71 resulting from sprinkling of water by the water sprinkling means 44A, to thereby obtain high-temperature steam 75 and feed the steam into the gasification furnace 10.

According to the present embodiment, the purified gas is first introduced into the water sprinkling means 44A, where the gas is cooled and moisture contained in the gas is recovered by sprinkling water 76. Subsequently, the thus-obtained gas is introduced into the alkaline water sprinkling means 44B for sprinkling an alkaline solution 77 (e.g.; NaOH), where acidic gases (e.g.; ammonia gas, hydrogen chloride, and a sulfur component ($H_2S$)) are removed from the gas by sprinkling the alkaline water.

Similar to the case of the ninth embodiment, in a first heat exchanger 72, discharge water 71 drained from the water sprinkling means 44A is subjected to heat-exchange with heat (approximately 300° C.) generated by catalytic reaction carried out in the methanol synthesis unit 27. Subsequently, the gas 21 produced from the gasification furnace 10 is fed to a cooling means 41, to thereby recover heat of the produced high temperature gas (e.g.; at approximately 900° C.) in a second heat exchanger 74. The resultant high-temperature steam 75 is supplied to the biomass gasification furnace 10.

In addition to the effect obtained from the ninth embodiment, the present embodiment employs a two-stage scrubber including the water sprinkling means 44A and the alkaline water sprinkling means 44B. Thus, cooling and moisture removal are effected by sprinkled water 76 at a first-stage, and at a second-stage, an acidic gas is removed by sprinkled alkaline water 77, to thereby prevent deterioration of units and piping on the downstream side caused by corrosion etc.

[Eleventh Embodiment]

<Methanol Synthesis System (11)>

A eleventh embodiment of the present invention will be described with reference to FIG. 11.

Figure 11:
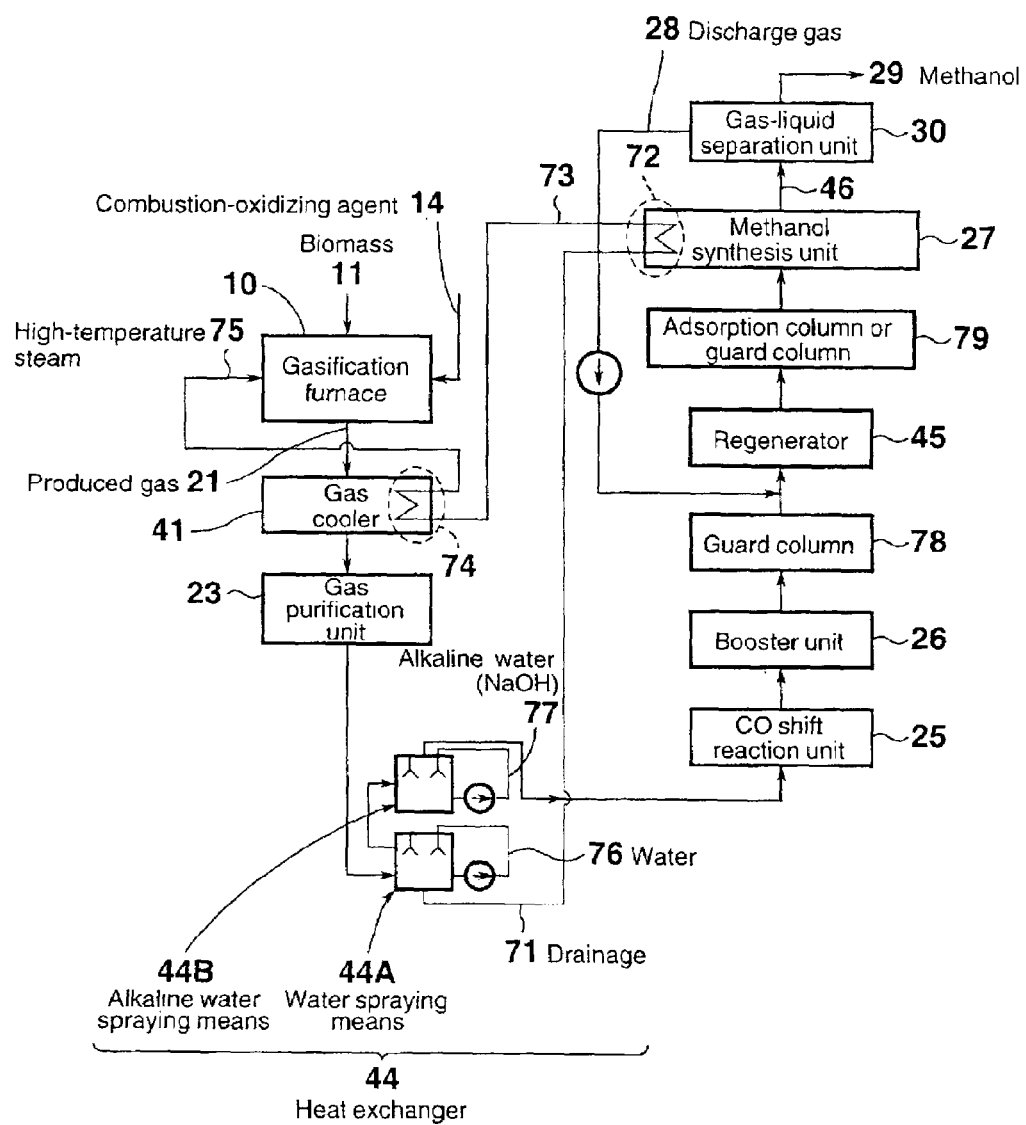
FIG. 11 is a schematic diagram of a methanol synthesis system employing a biomass gasification furnace according to the eleventh embodiment.

FIG. 11 is a schematic diagram of a methanol synthesis system making use of a gas produced through gasification performed in a biomass gasification furnace according to the eleventh embodiment.

Components having the same functions as those in the aforementioned methanol synthesis system are denoted by the same reference numerals, and repeated descriptions of such components are omitted.

The methanol synthesis system according to the present embodiment includes a first adsorption column or guard column 78 provided between the aforementioned booster unit 26 and regenerator 45 in the methanol synthesis system; and a second adsorption column or guard column 79 provided between the aforementioned regenerator 45 and methanol synthesis unit 27.

The aforementioned adsorption columns are filled with a substance having adsorption capability, such as silica gel or activated carbon. The guard columns are filled with a catalyst which is also employed in the methanol synthesis unit 27. They are "disposable" columns which are to be disposed or regenerated after use for a predetermined period of time.

These adsorption columns or guard columns are effective to prevent poisoning of a catalyst in the methanol synthesis system. Therefore, the methanol synthesis can be performed steadily for a long period of time.

In the present embodiment, two-stage protection is attained by use of the first adsorption column or guard column 78 and the second adsorption column or guard column 79. However, the present invention is not limited thereto. For example, only the first adsorption column or guard column 78 may be employed.

[Twelfth Embodiment]

<Methanol Synthesis System (12)>

A twelfth embodiment of the present invention will be described with reference to FIG. 12.

FIG. 12 is a schematic diagram of a methanol synthesis system making use of a gas produced through gasification performed in a biomass gasification furnace according to the twelfth embodiment.

Components having the same functions as those in the aforementioned methanol synthesis system are denoted by the same reference numerals, and repeated descriptions of such components are omitted.

The methanol synthesis system according to the twelfth embodiment effectively utilizes $H_2$ contained in discharge gas 28 which has been separated through gas/liquid separation of the gas 46 produced in a methanol synthesis unit 27.

As shown in FIG. 12, the produced gas 46 synthesized by the aforementioned methanol synthesis unit 27 is separated into methanol 29 and discharge gas 28 by means of a gas/liquid separation unit 30. Generally, the discharge gas 28 is fed back to a site on the upstream side of the regenerator 45 without any additional treatment. However, in this embodiment, a hydrogen ($H_2$) separation unit 80 for isolating only $H_2$ from the relevant discharge gas 28 is employed, to thereby elevate the $H_2$ content in the discharge gas 28 to be recycled.

The hydrogen separation unit 80 may employ a known hydrogen separation technique such as $H_2$ separation on the basis of a pressure swing technique or membrane separation.

According to the present embodiment, $H_2$ is exclusively isolated by the hydrogen separation unit 80, and the isolated $H_2$ is recycled to a site on the upstream side of the regenerator 45. Therefore, residual $H_2$ can be used effectively, leading to improved efficiency of hydrogen utilization for methanol synthesis.

[Thirteenth Embodiment]

<Methanol Synthesis System (13)>

A thirteenth embodiment of the present invention will next be described with reference to FIG. 13.

Figure 13:
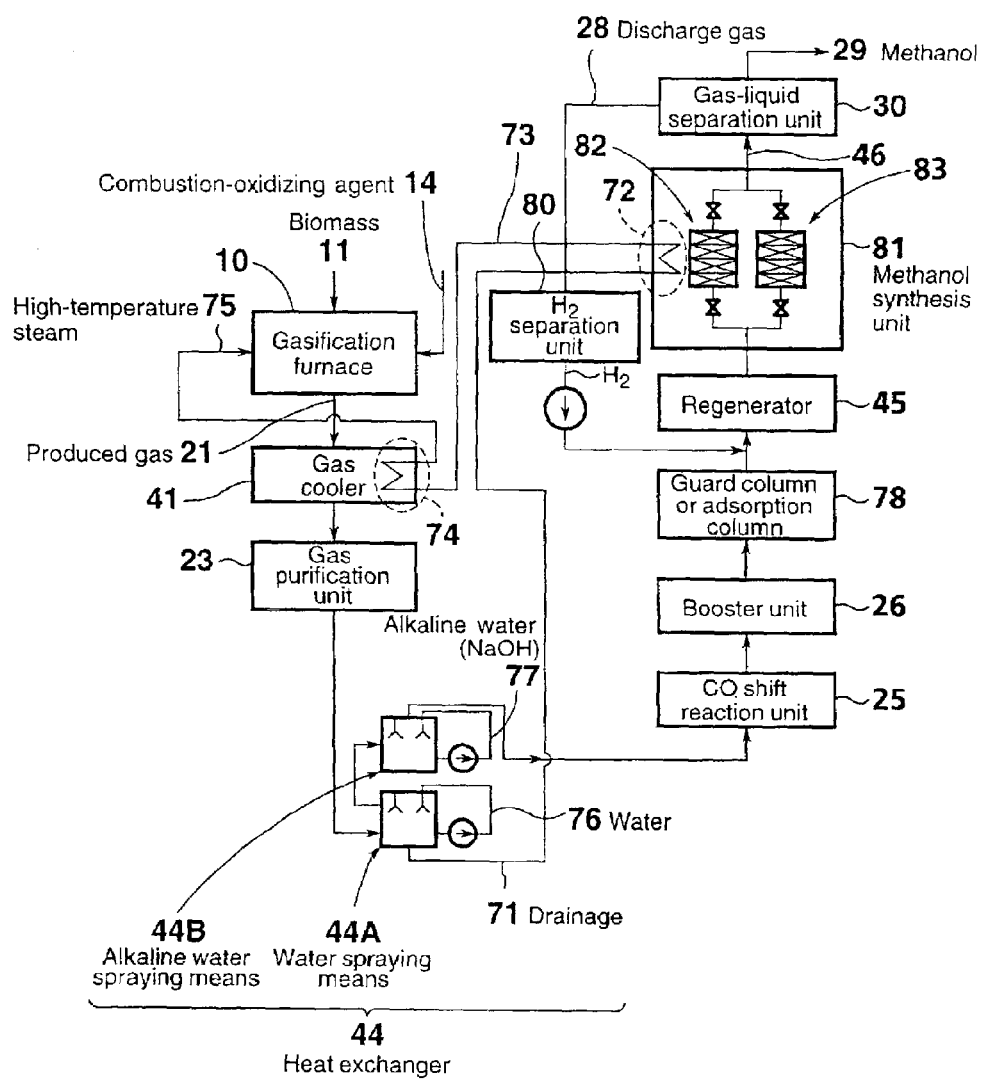
FIG. 13 is a schematic diagram of a methanol synthesis system employing a biomass gasification furnace according to the thirteenth embodiment.

FIG. 13 is a schematic diagram of a methanol synthesis system making use of a gas produced through gasification performed in a biomass gasification furnace according to the thirteenth embodiment.

Components having the same functions as those in the aforementioned methanol synthesis system are denoted by the same reference numerals, and repeated descriptions of such components are omitted.

The methanol synthesis system according to the thirteenth embodiment employs a methanol synthesis unit having two separate synthesis systems so as to continuously synthesize methanol.

Figure 14:
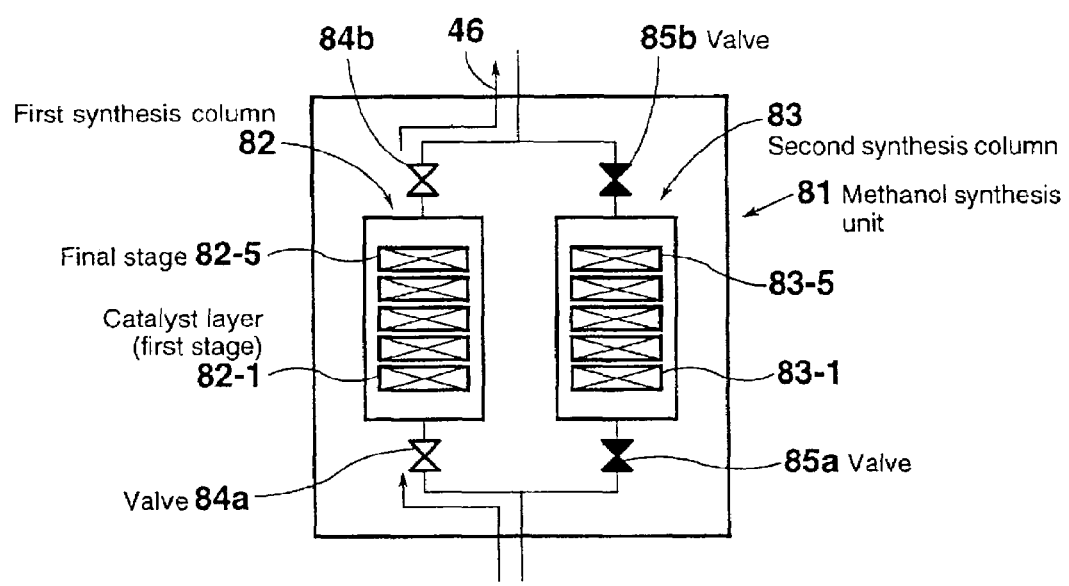
FIG. 14 is an enlarged view of the relevant portion of FIG. 13.

FIG. 14 shows an enlarged view of a methanol synthesis unit according to the thirteenth embodiment. As shown in FIGS. 13 and 14, the methanol synthesis unit 81 according to the present embodiment includes two separate synthesis systems; i.e., a first synthesis column 82 and a second synthesis column 83.

The first synthesis column 82 comprises valves 84a and 84b provided at both ends of the column. In the first synthesis column 82, a catalyst layer 82-1 serving as a first stage through a catalyst layer 82-5 serving as a final stage (five stages in this embodiment) are provided. Similarly, the second synthesis column 83 comprises valves 85a and 85b provided at both ends of the column. In the second synthesis column 83, a catalyst layer 83-1 serving as a first stage through a catalyst layer 83-5 serving as a final stage (five stages in this embodiment) are provided.

According to the thirteenth embodiment, as shown in FIG. 14, the first synthesis column 82 and the second synthesis column 83 are employed alternately during methanol synthesis. For example, during use of the first synthesis column 82, the valves 85a and 85b of the second synthesis column 83 are closed. Among catalyst layers of the second synthesis column 83, the degraded first-stage catalyst layer 83-1 provided in the vicinity of the gas inlet is removed, and the secondstage catalyst layer 83-2 is shifted to the position of the first stage. The remaining catalyst layers are shifted successively, and a new catalyst layer is placed as the final stage, to thereby sequentially substitute a degraded portion by a new catalyst layer.

Through the aforementioned substitution, the second-stage catalyst layer serves as a first-stage catalyst layer, to thereby maintain desirable catalyst activity, attaining excellent methanol synthesis.

Through the employment of the thirteenth embodiment, ease of maintenance of the methanol synthesis unit is improved.

In the thirteenth embodiment, although a guard column 78 is provided on the upstream side of the regenerator 45, the guard column 78 is not essential. However, provision of the guard column 78 prevents poisoning of the catalyst and decrease in catalyst activity.

Alternatively, guard columns may be employed as the first-stage catalyst layers 82-1 and 83-1, and may be disposed of after use for a predetermined period of time.

The present embodiment employs two series of catalytic synthesis columns. However, the present invention is not limited thereto, and a plurality of series of synthesis columns may be employed for the enhancement of synthesis efficiency.

[Fourteenth Embodiment]

Figure 15:
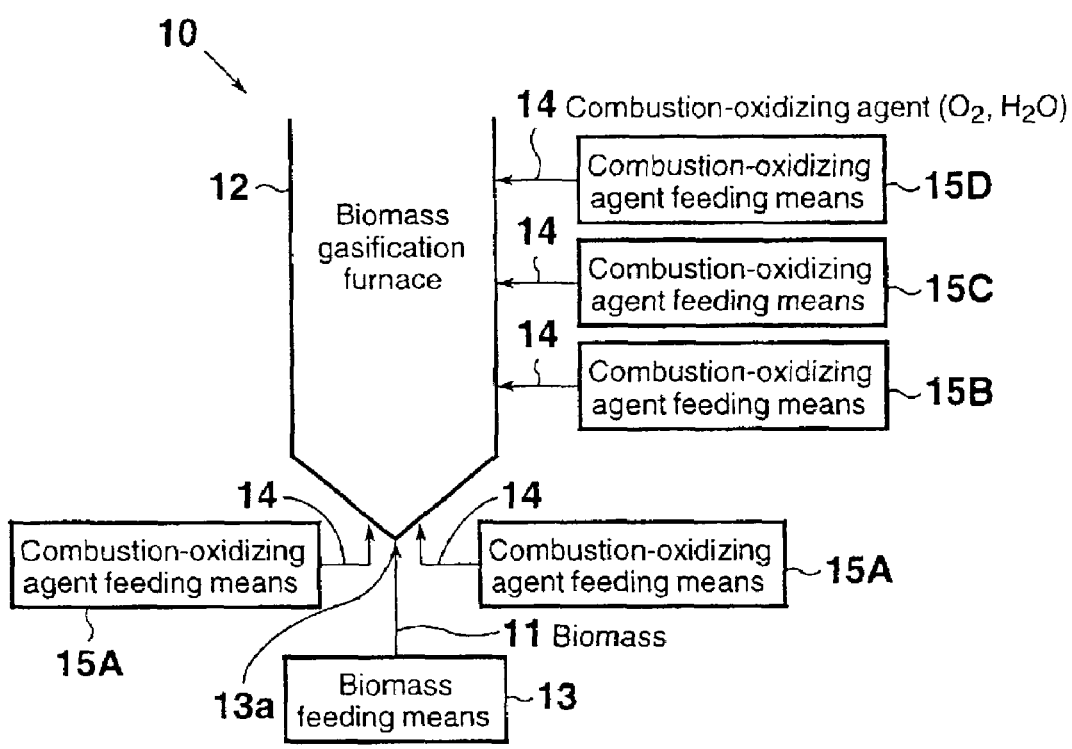
FIG. 15 is a schematic diagram of a biomass gasification furnace according to the fourteenth embodiment.

FIG. 15 shows a schematic view of a biomass gasification furnace according to the fourteenth embodiment.

In a biomass gasification furnace 10 according to the present embodiment, a combustion-oxidizing agent 14 which contains oxygen or a mixture of oxygen and steam is fed to a furnace main body 12 through a multi-stage-feeding method.

According to the present embodiment, as shown in FIG. 15, feeding means 15A to 15D are provided for feeding the combustion-oxidizing agent 14 via a plurality of points which are provided along the perpendicular axis of the furnace main body 12. The feeding means 15A to 15D are provided upward in a sequential manner at predetermined intervals, so that the combustion-oxidizing agent 14 for promoting gasification is fed sequentially downstream with respect to the gas flow.

According to the present embodiment, biomass 11 is fed by a biomass feeding means 13 so that the biomass is supplied from the lower section of the furnace main body 12, and a plurality of feeding ports (two ports in the case of this embodiment) of the combustion-oxidizing agent feeding means 15A are provided at predetermined points on concentric circles centering the feeding port 13a of the feeding means 13.

Therefore, since the combustion-oxidizing agent 14 is fed in a sequential manner from a plurality of stages, gasification efficiency is improved.

Employment of a gasification furnace according to the present embodiment serving as the gasification furnace for the aforementioned methanol synthesis system will improve the efficiency of the methanol synthesis.

[Fifteenth Embodiment]

Figure 16:
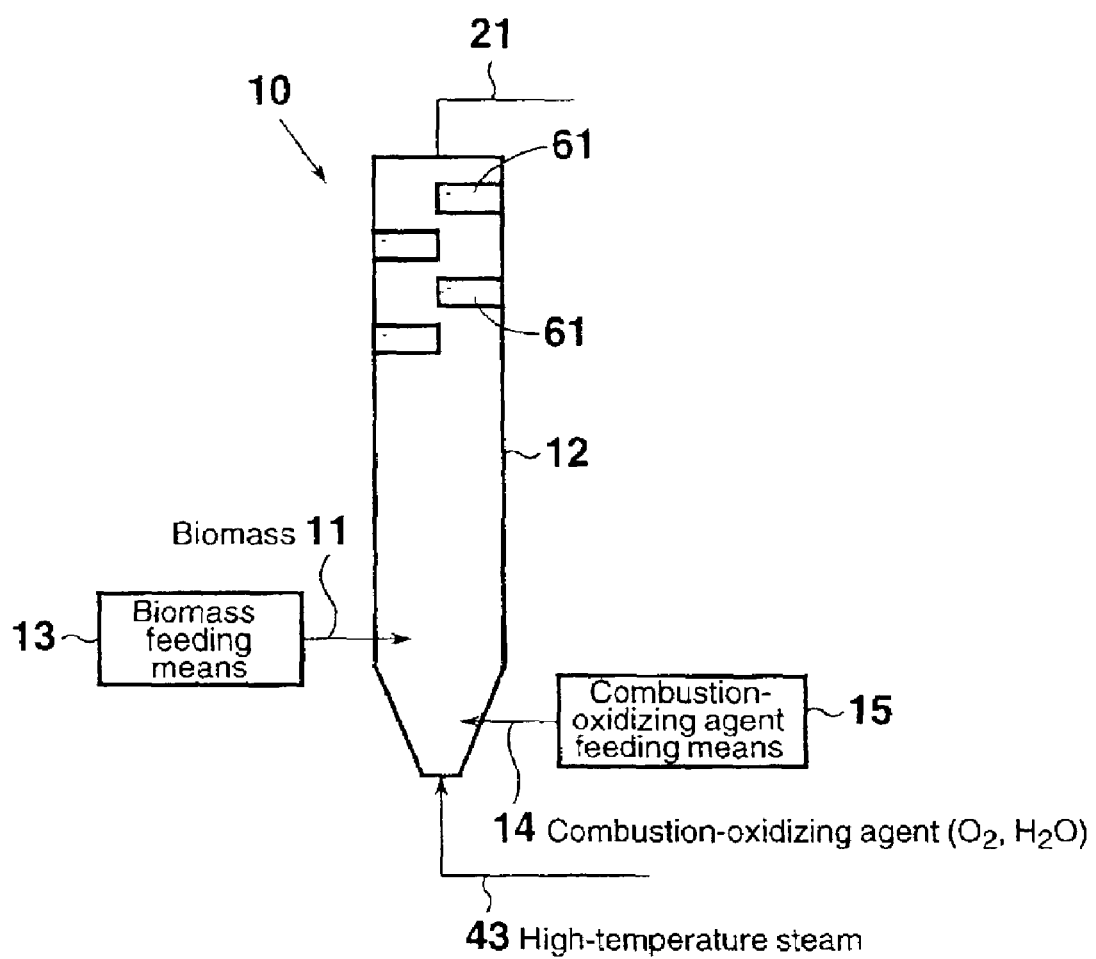
FIG. 16 is a schematic diagram of a biomass gasification furnace according to the fifteenth embodiment.

FIG. 16 is a schematic diagram of a biomass gasification furnace according to the fifteenth embodiment. As shown in FIG. 16, the biomass gasification furnace 10 according to the fifteenth embodiment a comprises biomass feeding means 13 for feeding biomass 11 into the furnace main body 12; a combustion-oxidizing agent feeding means 15, provided at a site on the upstream side of the biomass feeding means 13 (on the downstream side of the furnace), for feeding a combustion-oxidizing agent 14 comprising oxygen or a mixture of oxygen and steam into the furnace main body 12; and a plurality of nickel-catalyst-on-ceramic foam plates 61 provided within the upper portion of the furnace such that the plates alternately extend in opposite directions.

The ceramic foam plates 61 capture tar and soot contained in the gas generated through gasification of biomass 11 and decompose captured tar substances into CO and $H_2$ by the action of nickel catalysts, to thereby provide a gas having a composition suitable for methanol synthesis.

Since the aforementioned plates of ceramic foam 61 also serve as radiation converters, a uniform gasification temperature throughout the interior of the gasification furnace main body 12 can be attained, resulting in enhancement of gasification reaction efficiency in the gasification furnace main body 12.

In the present embodiment, high-temperature steam 43 is introduced from the outside through the bottom section of the furnace main body 12.

[Sixteenth Embodiment]

Figure 17:
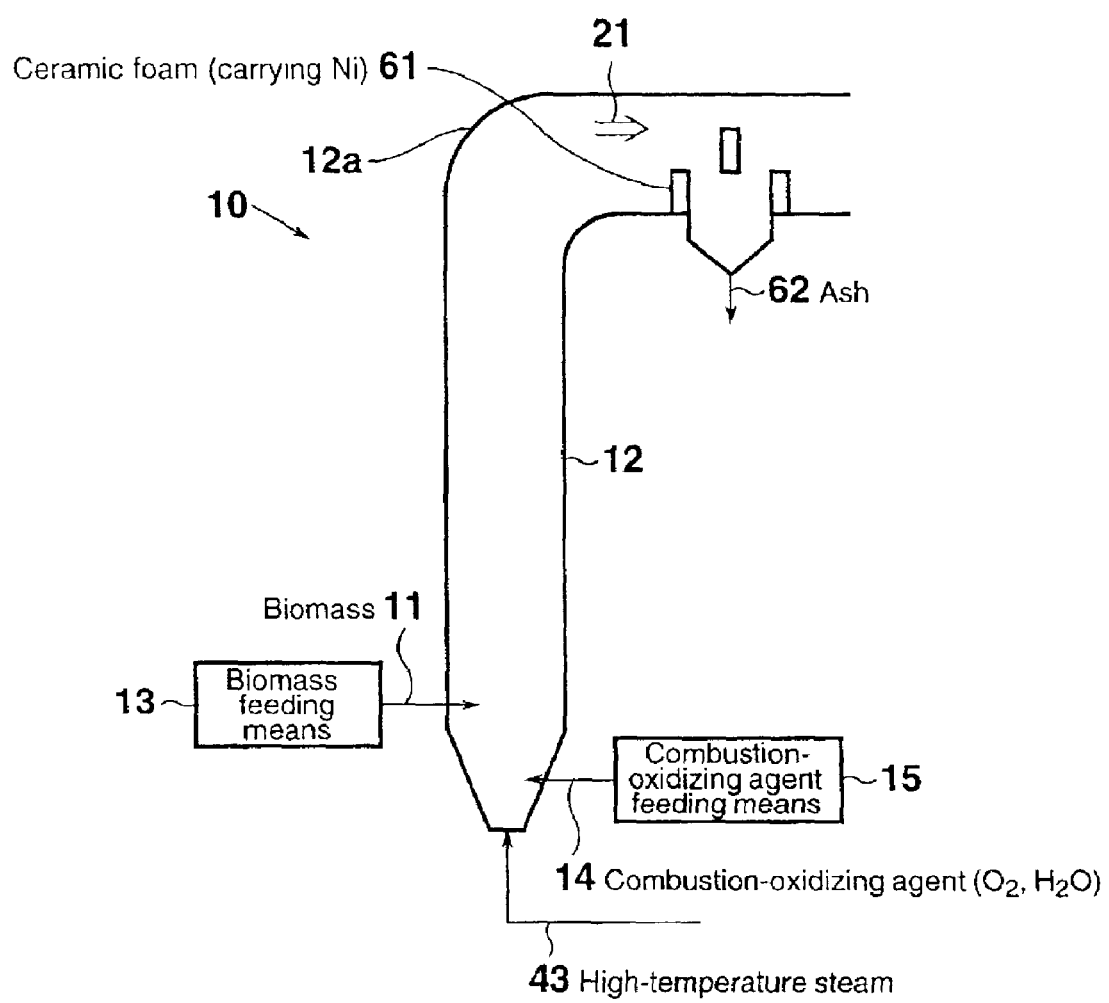
FIG. 17 is a schematic diagram of a biomass gasification furnace according to the sixteenth embodiment.

FIG. 17 is a schematic diagram of a biomass gasification furnace according to a sixteenth embodiment.

As shown in FIG. 17, the biomass gasification furnace 10 according to the present embodiment comprises a plurality of Ni-catalyst-on-ceramic foam plates 61 provided at a site on the downstream side of the bent portion of the upper portion 12a of the furnace main body 12 such that the plates alternately extend in opposite directions.

The ceramic foam plates 61 capture tar and soot contained in the gas generated through gasification of biomass 11 and decompose captured tar substances into CO and $H_2$ by the action of nickel catalysts, to thereby provide a gas having a composition suitable for methanol synthesis.

Ash 62 deposited on the ceramic foam 61 can be discharged to the outside through unillustrated means such as steam spraying.

[Seventeenth Embodiment]

Figure 18:
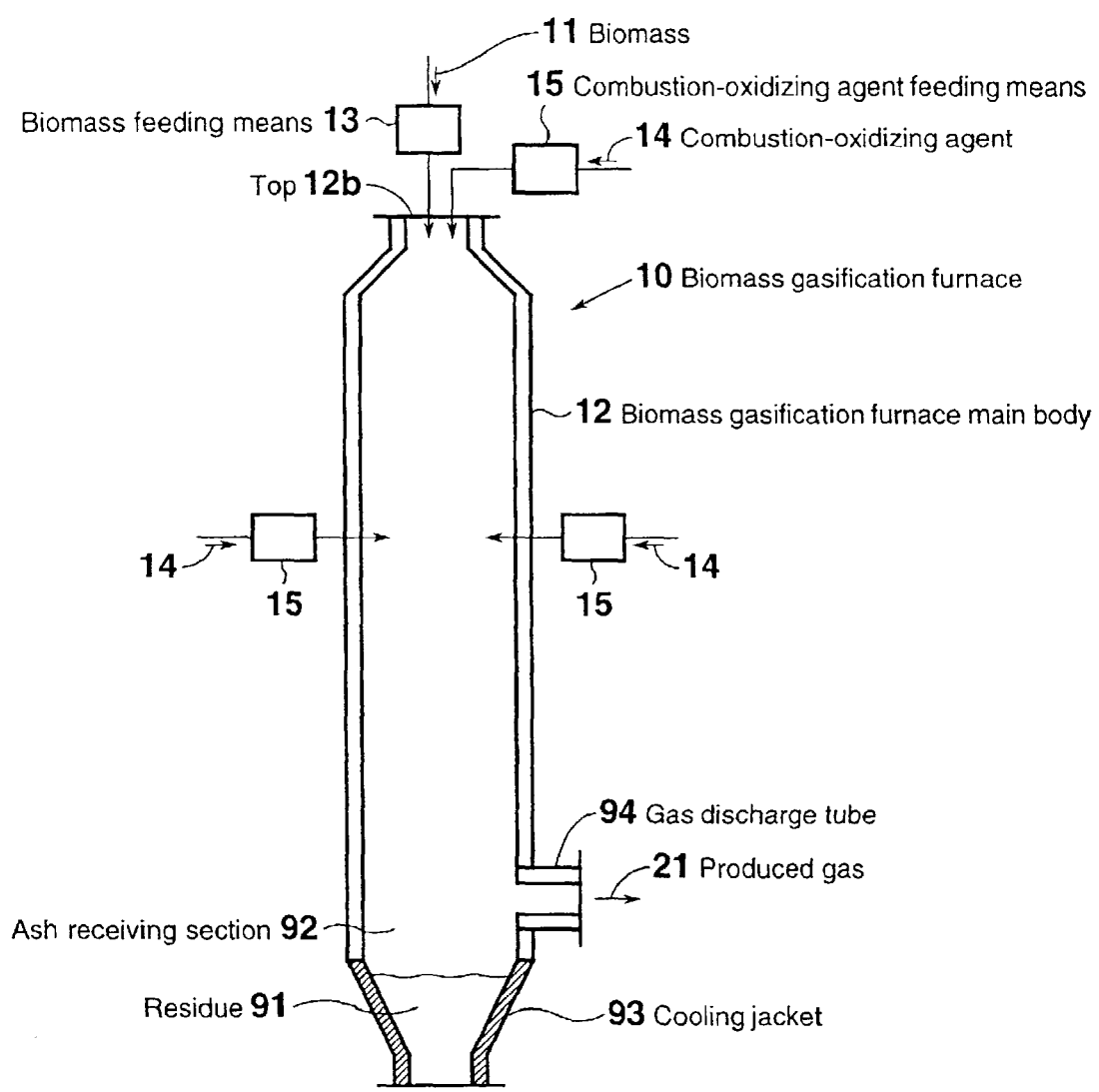
FIG. 18 is a schematic diagram of a biomass gasification furnace according to the seventeenth embodiment.

FIG. 18 shows a schematic diagram of a biomass gasification furnace according to the seventeenth embodiment. As shown in FIG. 18, the biomass gasification furnace 10 according to the seventeenth embodiment produces a gas 21 through gasification/combustion of biomass 11 and a combustion-oxidizing agent 14, such as oxygen, at high temperature. The biomass gasification furnace 10 includes, at a top section 12b of a gasification furnace main body 12 made of a refractory material, a biomass feeding means 13 for feeding biomass 11 which has been pulverized to a predetermined grain size into the furnace; and a combustion-oxidizing agent feeding means 15 for feeding a combustion-oxidizing agent 14, such as a mixture of oxygen or air and steam, into the furnace main body 12.

The lower section of the furnace main body 12 includes an ash receiving section 92 for receiving combustion residue 91 containing substances that remain uncombusted after gasification. The wall defining the ash receiving section 92 makes a cooling jacket 93 having a downwardly reduced diameter.

A gas discharge tube 94 is provided in a lower section of the side wall of the furnace main body 12. The gas discharge tube 94 discharges gas 21 produced by biomass gasification.

In the present embodiment, the biomass 11 is fed downward from the top section 12b of the biomass gasification furnace 10. Therefore, even when biomass contains large amounts of low-melting-point substances, unlike the case in which biomass is blown upward, deposition of uncombusted components onto the inner wall surface of the furnace can be prevented, thereby realizing continuous biomass gasification.

Particularly, when biomass containing a larger amount of an alkaline component, such as an Na salt, a K salt, and a P salt, is used as starting material, the ash melting point lowers to as low as 600° C. However, feeding the biomass 11 from the top section 12b of the furnace prevents deposition and formation of ash.

According to the present invention, biomass of any composition other than biomass having a specific high melting point can be gasified. The invention provides a gasification furnace highly suited for general purposes, not for specific biomass of high melting point.

Since solid ash is deposited to the inner surface of the ash receiving section 92 through cooling by the cooling jacket 93, deposition between the ash and the inner surface is weak. Therefore, the ash can be forcedly removed through blowing of steam by use of, for example, soot removing means.

[Eighteenth Embodiment]

Figure 19:
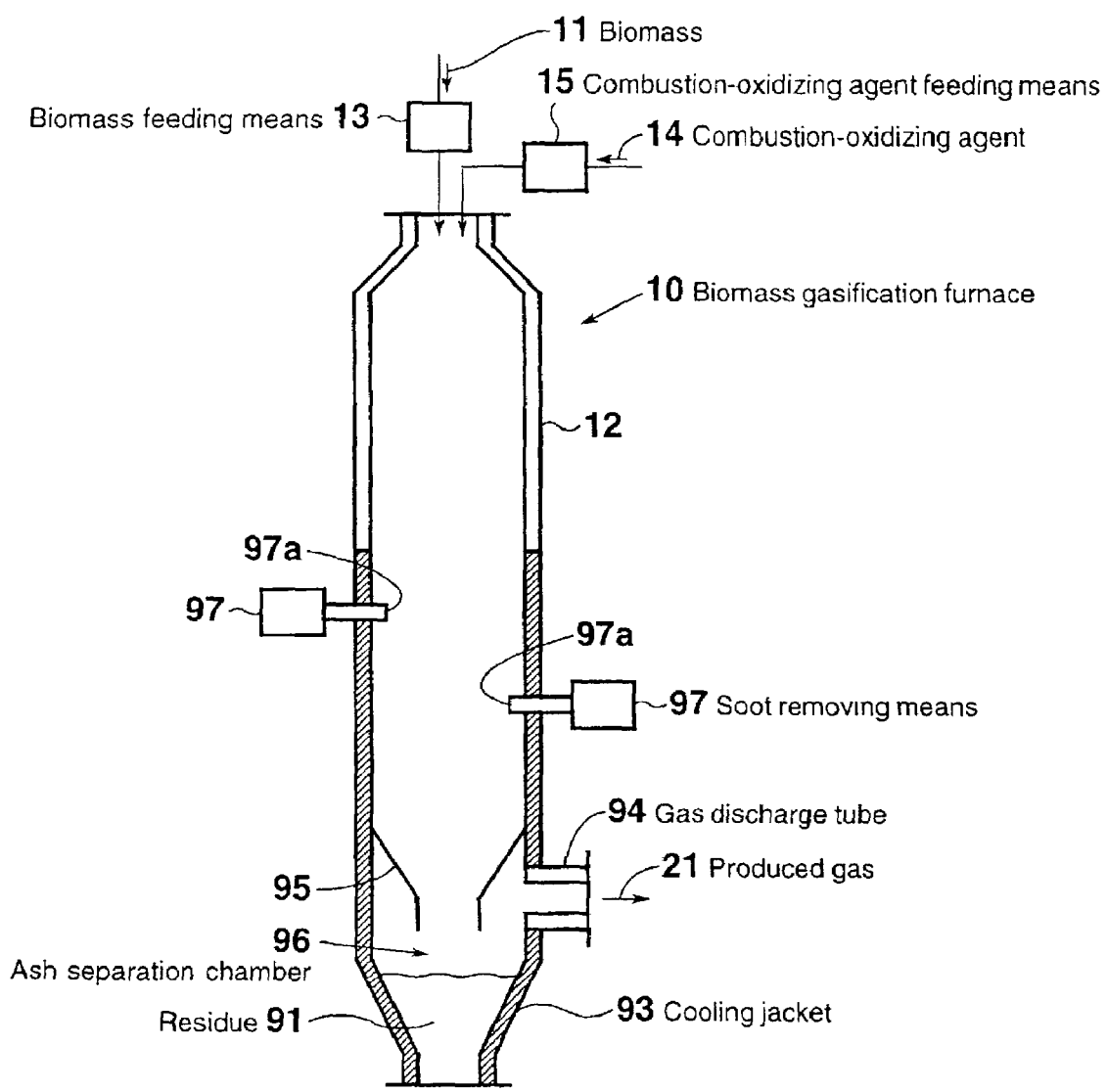
FIG. 19 is a schematic diagram of a biomass gasification furnace according to the eighteenth embodiment.

FIG. 19 shows a schematic diagram of a biomass gasification furnace according to the present embodiment. Components identical with those in the gasification furnace of the above-described embodiments are represented by the same reference numerals, and repeated descriptions of such components are omitted.

As shown in FIG. 19, the biomass gasification furnace 10 according to the eighteenth embodiment includes a hollow cylindrical gas-ash introducing means 95 having a downwardly reduced diameter, which means is provided above and in the vicinity of a gas discharge tube 94 provided in the side wall of the lower portion of the gasification furnace main body 12, the upper end of the means 95 being joined to the inner surface of the main body, and an ash separation chamber 96 being provided below the gas-ash introducing means 95.

According to the present embodiment, since the gas-ash introducing means 95 and the ash separation chamber 96 are provided, the flow rates of the gas and ash which are introduced into the ash separation chamber 96 from the ash introducing means 95 are reduced in the chamber 96. Therefore, the ash and the gas are easily separated from each other, and transfer of the ash to the gas discharge tube 94 is prevented.

In this embodiment, a cooling jacket 93 is provided so as to extend from the central portion to the lower portion of the gasification furnace main body, and soot removing means (desludger) 97 for injecting steam toward the inner surface of the furnace is provided, thereby facilitating removal of solid matter deposited to the inner surface.

The soot removing means 97 of this embodiment has two injection openings 97a facing each other in an offset manner. However, the present invention is not limited thereto, and, if necessary, the position of each injection opening may be changed, and the number of the injection openings may be increased.

Figure 20:
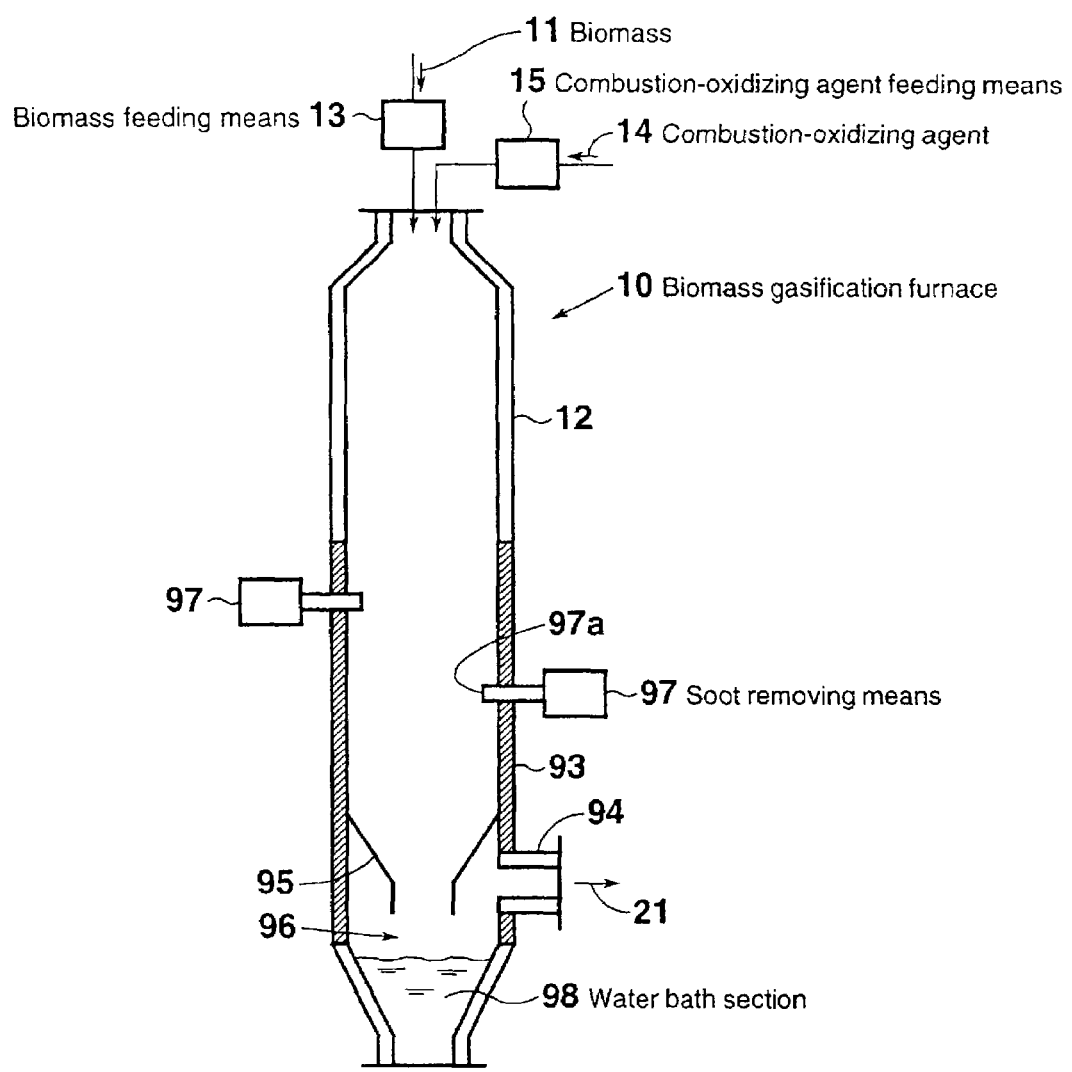
FIG. 20 is a schematic diagram of an alternative gasification furnace according to the eighteenth embodiment.

As shown in FIG. 20, a water bath section 98 may be provided at the lower section of the gasification furnace so as to recover the separated ash in a wet state.

[Nineteenth Embodiment]

Figure 21:
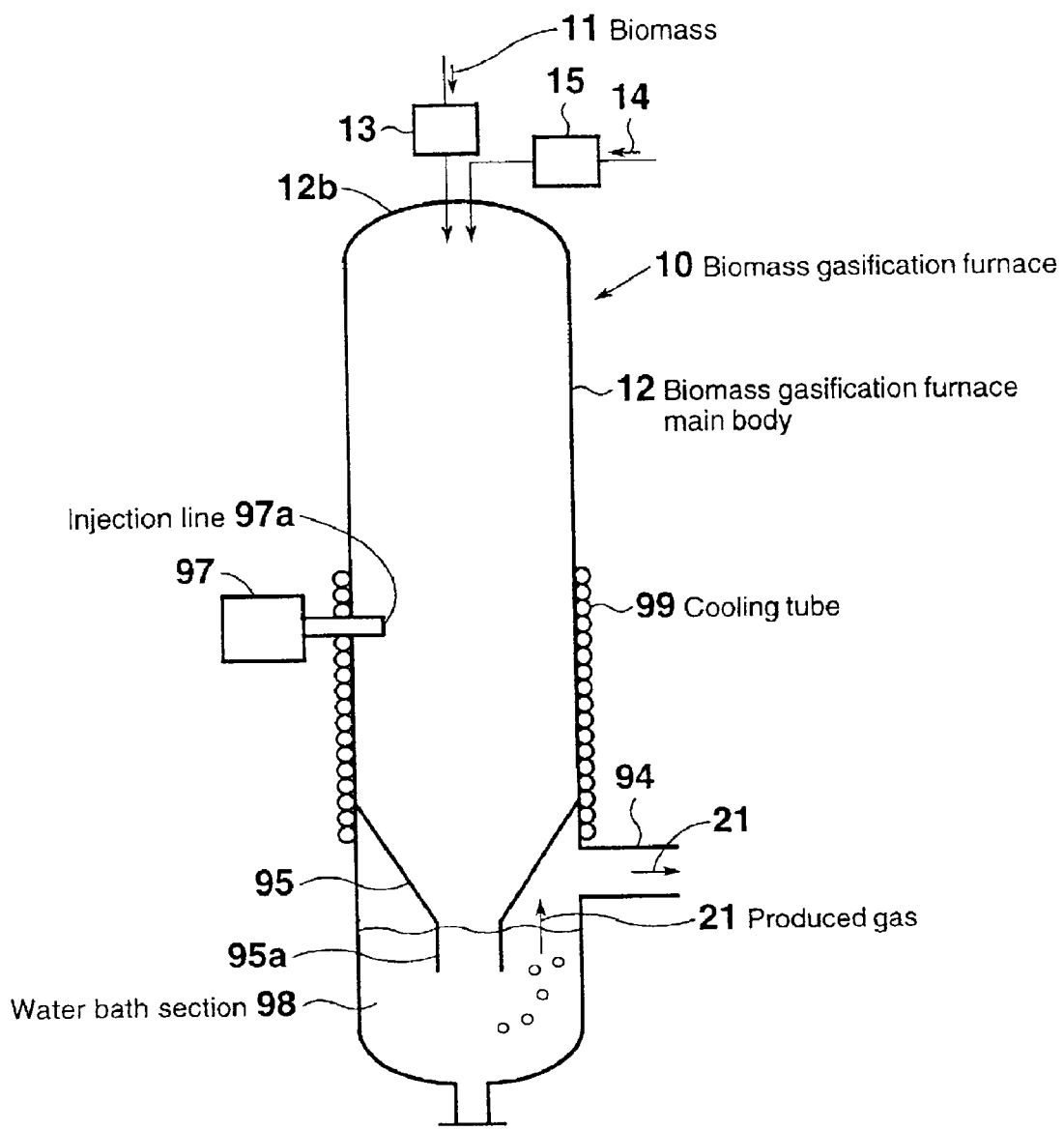
FIG. 21 is a schematic diagram of a biomass gasification furnace according to the nineteenth embodiment.

FIG. 21 shows a schematic diagram of a biomass gasification furnace according to the nineteenth embodiment. Components identical with those in the gasification furnace of the above-described embodiments are represented by the same reference numerals, and repeated descriptions of such components are omitted.

The biomass gasification furnace 10 according to the present embodiment includes a water bath section 98 provided at the lower portion of a gasification furnace main body 12; and a hollow cylindrical gas introducing means 95 having a downwardly reduced diameter, the tip end portion 95a of the means 95 being dipped in the water bath section 98.

In this embodiment, a water-cooling tube 99 is provided in such a manner that the tube 99 extends from the central portion to the lower portion of the gasification furnace main body 12 so as to cool the side wall of the main body 12.

According to the nineteenth embodiment, since the produced gas is passed once through the water bath section 98, water contained in the gas is removed.

Since the gas is introduced into the water bath section, a trace amount of ash contained in the gas is actively cooled and solidified.

Particularly, the nineteenth embodiment is suitable for gasification of biomass which produces ash of low melting point.

[Twentieth Embodiment]

Figure 22:
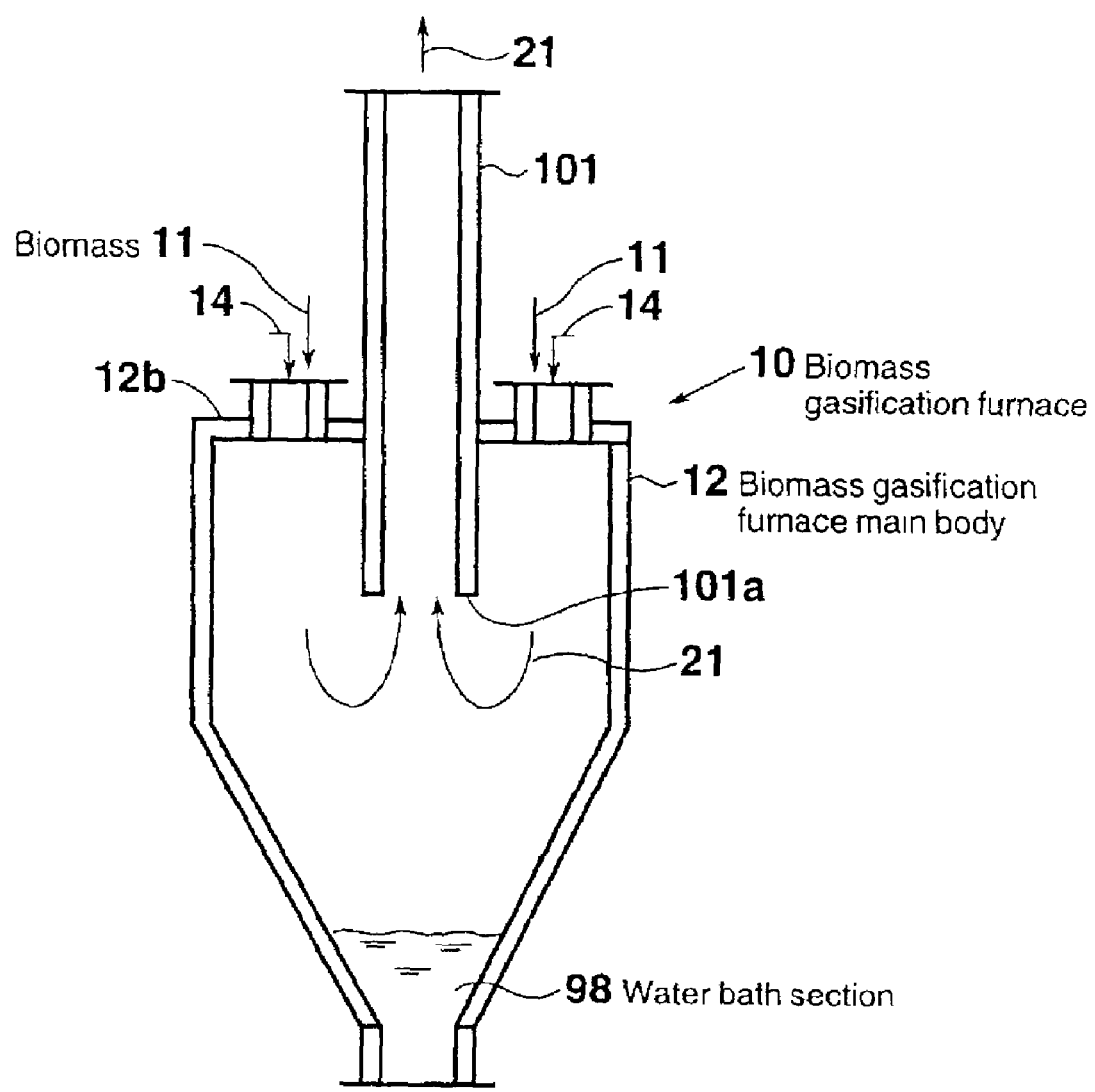
FIG. 22 is a schematic diagram of the biomass gasification furnace according to the twentieth embodiment.

FIG. 22 shows a schematic diagram of a biomass gasification furnace according to the twentieth embodiment. Components identical with those in the gasification furnace of the above-described embodiments are represented by the same reference numerals, and repeated descriptions of such components are omitted.

As shown in FIG. 22, the biomass gasification furnace 10 according to the present embodiment includes a gas discharge tube 101 for discharging a produced gas 21 and provided at the center of the top section 12b of a gasification furnace main body 12, the gas discharge tube 101 vertically extending such that a lower portion of the gas discharge tube projects into the interior of the gasification furnace for a predetermined length, and a lower end opening 101*a* of the gas discharge tube 101 faces the interior of the gasification furnace.

The lower portion of the gasification furnace main body 12 has a hollow cylindrical shape having a downwardly reduced diameter, and a water bath section 98 is provided at the lower side of the main body 12, to thereby trap melted ash.

According to the present embodiment, biomass 11 is downwardly fed to the gasification furnace. However, since the gas 21 produced through gasification is discharged upward through the gas discharge tube 101, a gasification region increases, to thereby enhance gasification efficiency.

Since the entirety of the lower portion of the gasification furnace main body has a downwardly reduced diameter, the produced gas 21 is concentrated to the central portion of the main body, to thereby efficiently introduce the gas 21 into the discharge tube 101.

Since the lower portion of the gasification furnace main body has a downwardly reduced diameter, melted ash readily falls, to thereby increase the trapping ratio of the melted ash in the water bath section 98.

[Twenty-First Embodiment]

Figure 23:
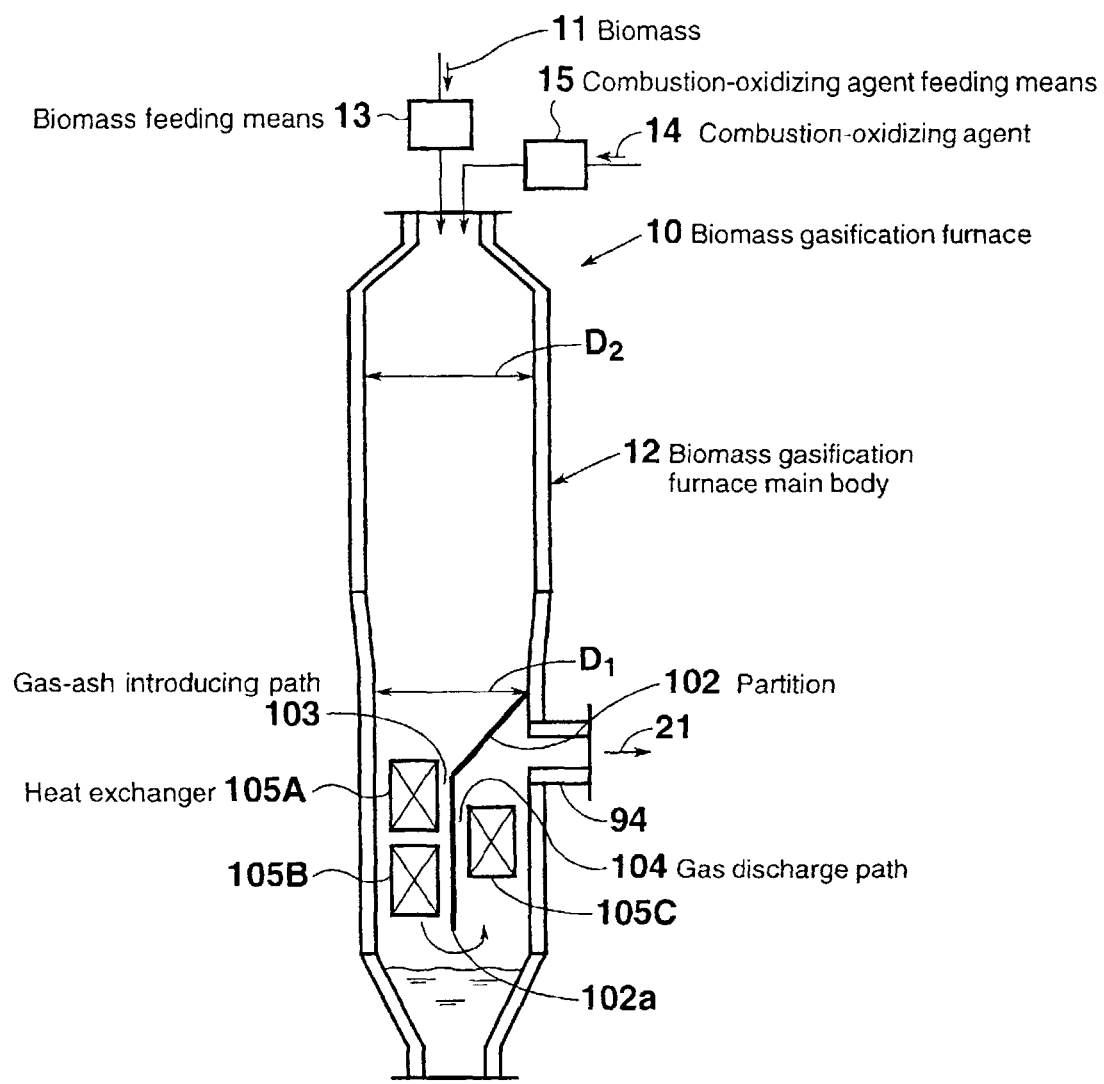
FIG. 23 is a schematic diagram of a biomass gasification furnace according to the twenty-first embodiment.

FIG. 23 shows a schematic diagram of a biomass gasification furnace according to the present embodiment. Components identical with those in the gasification furnace of the above-described embodiments are represented by the same reference numerals, and repeated descriptions of such components are omitted.

As shown in FIG. 23, the biomass gasification furnace 10 according to the present embodiment has a structure such that the diameter $D_1$, of the aforementioned gasification furnace main body 12 in the portion below the central portion is slightly smaller than the diameter $D_2$ of the main body 12 in the portion above the central portion, and a partition 102 is vertically provided in such a manner that one end of the partition 102 is joined to the inner wall surface of the smaller-diameter portion of the main body. By providing the partition 102 inside the furnace main body, a path 103 for introducing a produced gas and ash and a gas discharge path 104 are formed, so as to allow the produced gas and ash to pass through the path, and the flow of the produced gas 21 is turned upward at the end 102*a* of the partition 102, thereby separating the ash from the produced gas and allowing the gas to pass through the gas discharge path 104 for discharge through a produced gas discharge tube 94.

In the twenty-first embodiment, heat exchangers 105A, 105B, and 105C are provided in the gas-ash introducing path 103 and the gas discharge path 104, to thereby subject latent heat of the gas to heat exchange.

According to the twenty-first embodiment, separation of the produced gas 21 can be carried out efficiently, and steam, etc. are effectively utilized through recovery of the latent heat of the gas.

[Twenty-Second Embodiment]

In the above-described embodiments, biomass is employed as a raw material for gasification. In this embodiment, one example of gasification by use of a fossil fuel, such as coal, will be described.

In a twenty-second embodiment, biomass is combusted in combination with a fossil fuel. Examples of the fossil fuel include coal and heavy oil.

Figure 24:
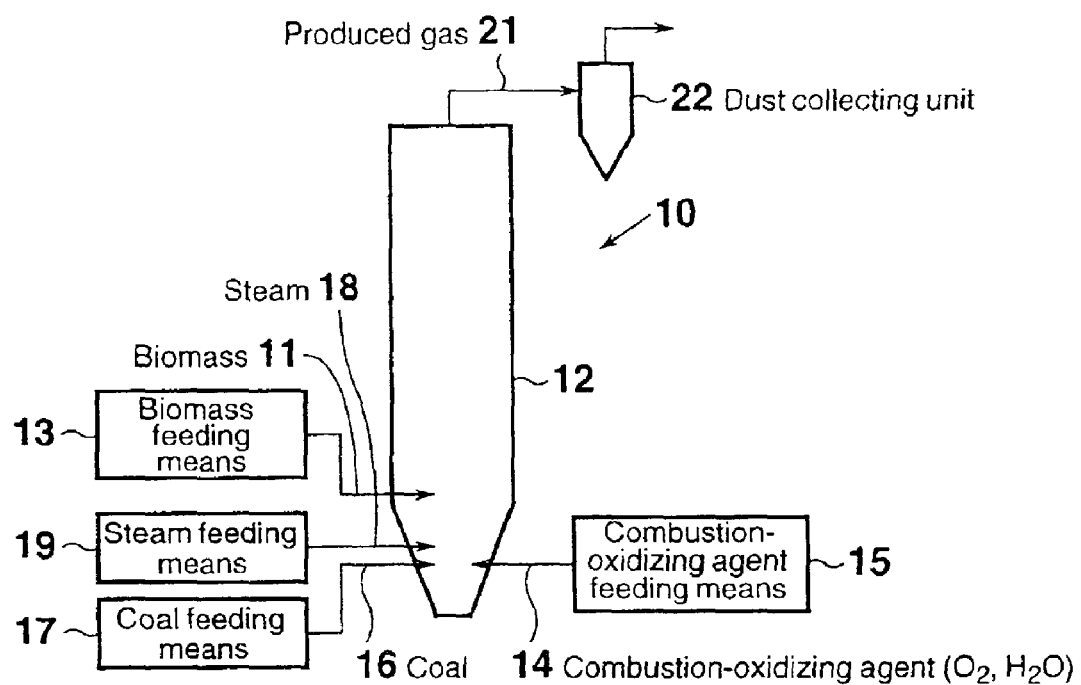
FIG. 24 is a schematic diagram of a biomass gasification furnace according to the twenty-second embodiment.

FIG. 24 shows a schematic diagram of a biomass gasification furnace according to the twenty-second embodiment. As shown in FIG. 24, the biomass gasification furnace 10 according to the twenty-second embodiment is an entrained-bed-type gasification furnace, comprising a biomass feeding means 13 for feeding biomass 11 to a furnace main body 12; a combustion-oxidizing agent feeding means 15 for feeding a combustion-oxidizing agent 14 containing oxygen or a mixture of oxygen and steam to the furnace main body 12, the means 15 being provided below (i.e.; on the downstream side of the furnace) the biomass feeding means; a coal feeding means 17 for feeding coal 16 to the furnace, the means 17 facing the combustion-oxidizing agent feeding means 15; and a steam feeding means 19 for feeding steam 18, the means 19 being provided at a central position between the coal feeding means 17 and the biomass feeding means 13.

In the twenty-second embodiment, in order to provide a combustion aid portion at the lower portion of the furnace main body 12, coal 16 serving as fossil fuel is fed to the furnace, and a high-temperature portion is formed through combustion of coal 16 serving as fossil fuel, without permitting combustion of biomass 11. The biomass 11 is fed to the thus-formed high temperature portion, to thereby efficiently carry out thermal decomposition and gasification of the biomass 11. In this embodiment, the combustion-oxidizing agent is employed also as a fuel for providing the high-temperature portion.

Heretofore, when reaction proceeds slowly in the case in which, for example, the calorific value of biomass is low, fossil fuel is supplied together with the biomass. According to the present invention, since fossil fuel and biomass are supplied separately through different positions, a high-temperature portion is provided at a combustion aid portion without self-combustion of biomass, and the biomass is gasified at the high-temperature portion. Therefore, gasification of the biomass can be carried out at high efficiency.

As a result, a gas suitable for methanol synthesis can be produced at high efficiency and low cost; conversion of carbon can be enhanced; problems caused by, for example, deposition of tar and a like substance can be eliminated, and the feed amount of oxygen or air can be reduced. In addition, a gas containing a large amount of hydrogen can be produced.

In the case in which coal 16 is employed as fossil fuel, the coal may be pulverized to form coal micropowder, and conveyed in the form of a gas mixture containing steam and air, or steam and oxygen.

In addition, when a heavy oil or an oil typically employed for combustion is employed to promote combustion, these oils may be sprayed into the furnace in the form of a gas mixture containing a spray medium, such as steam and air, or steam and oxygen.

[Twenty-Third Embodiment]

In a twenty-third embodiment, biomass is fed to a coal gasification furnace, so as to enhance the efficiency of the production of a gas for methanol synthesis.

Figure 25:
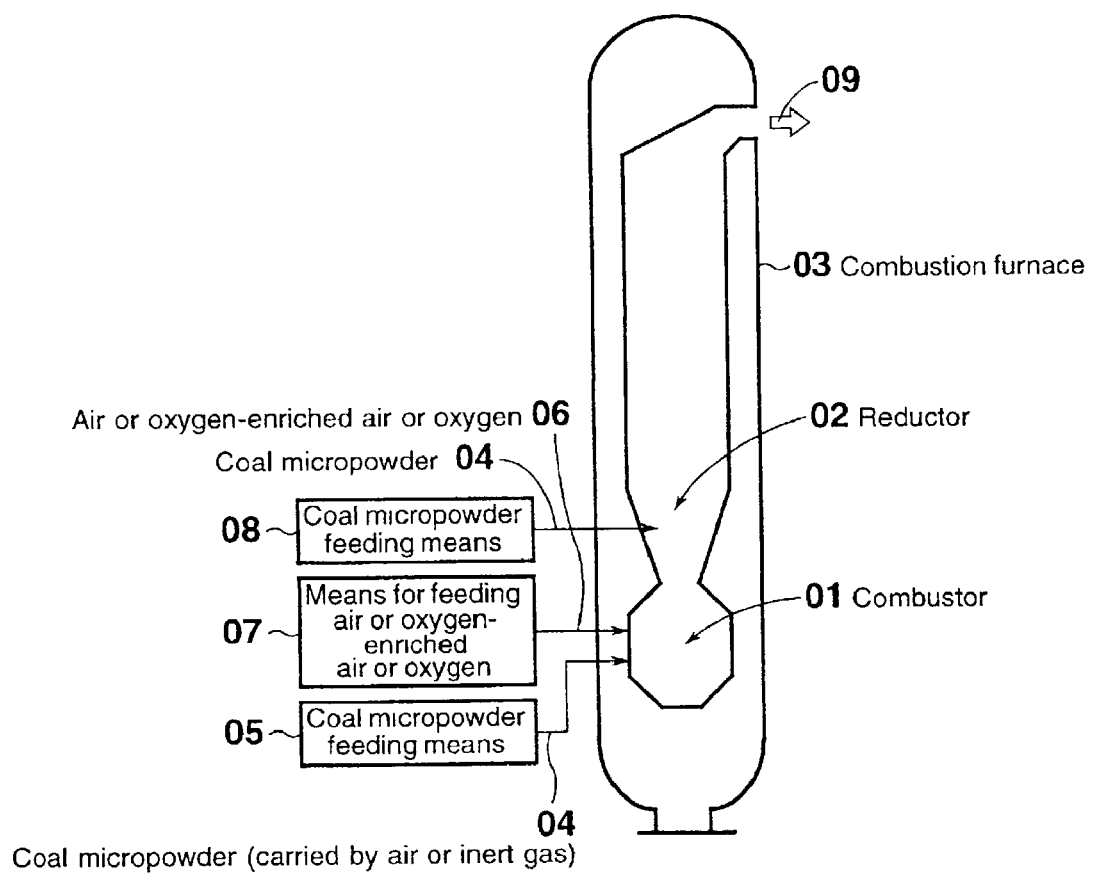
FIG. 25 is a schematic diagram of a conventional coal gasification furnace.

FIG. 25 schematically shows a conventional two-stage entrained-bed-type gasification furnace comprising a combustor and a reductor. As shown in FIG. 25, the two-stage entrained-bed-type gasification furnace comprises a combustion furnace 03 comprising therein a combustor 01, for carrying out combustion, and a reductor 02 for carrying out gasification reaction, the reductor 02 being provided above the combustor 01; a coal micropowder feeding means 05 for feeding, into the combustor 01, coal micropowder 04 obtained by pulverizing coal; an air supplying means 07 for supplying air, oxygen-enriched air, or oxygen 06 for combustion; and a coal micropowder feeding means 08 for feeding, into the reductor 02, coal micropowder 04. Construction of a gasification furnace is not limited to the embodiment shown in FIG. 25, wherein the regions of the combustor and the reductor are not clearly defined by a narrowed portion.

The coal micropowder 04 fed from the coal micropowder feeding means 05 is subjected to high-temperature—high-load combustion in the presence of air, oxygen-enriched air, or oxygen 06 for combustion. The thus-generated high-temperature combustion gas is fed to the reductor 02. The coal micropowder 04 is sprayed into the reductor 02 from the separately provided coal micropowder feeding means 08, and is subjected to dry-distillation by use of the high-temperature combustion gas generated in the combustor 01, thereby causing gasification.

A gas 09 formed through gasification is purified, and subsequently, the resultant gas is transported to a gas turbine to be utilized for generating electricity.

However, the gas 09 formed through gasification of coal predominantly contains CO has a low calorific value and a poor hydrogen content. Thus, the gas 09 is not suitable to serve as a raw material for methanol synthesis. Therefore, development of a method for gasification through employment of a coal gasification furnace that produces a gas having a useful composition for methanol synthesis has been desired.

Figure 26:
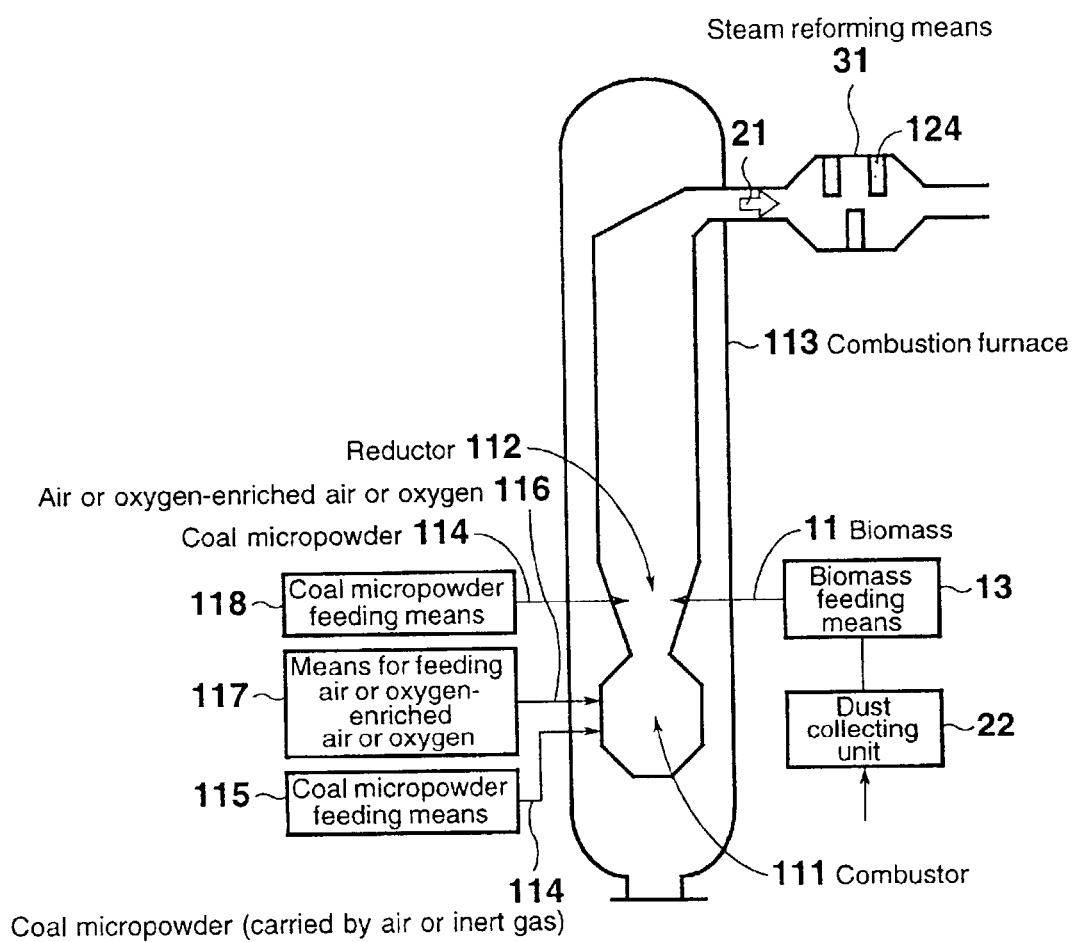
FIG. 26 is a schematic diagram of a coal gasification furnace according to the twenty-third embodiment.

Accordingly, the coal gasification furnace of the present embodiment is drawn to a two-stage entrained-bed-type gasification furnace, comprising, as shown in FIG. 26, a combustion furnace 113 equipped therein with a combustor 111 for carrying out combustion and a reductor 112 for carrying out gasification, the reductor 112 being provided above the combustor 111; a coal micropowder feeding means 115 for feeding, to the combustor 111, coal micropowder 114 obtained through pulverization of coal; means for feeding air, oxygen-enriched air, or oxygen (hereinafter referred to as "air, etc. feeding means") 117 for feeding air or oxygen-enriched air or oxygen (hereinafter referred to as "air, etc.") 116 for combustion; a coal micropowder feeding means 118 for feeding coal micropowder 114 to the reductor 112; and a biomass feeding means 13 for feeding pulverized biomass 11 to the reductor 112.

In the above apparatus, the coal micropowder 114 fed through the coal micropowder feeding means 115 is subjected to high-temperature—high-load combustion in the presence of air, etc. 116 for aiding combustion. The resultant high-temperature combustion gas is fed to the reductor 112. The coal micropowder 114 fed from the separately provided coal micropowder feeding means 118 and the biomass 11 fed by the biomass feeding means 13 are injected into the reductor 112, and are subjected to dry-distillation under the high-temperature combustion gas generated in the combustor 111, to thereby gasify the biomass, yielding a produced gas 21.

Figure 27A:
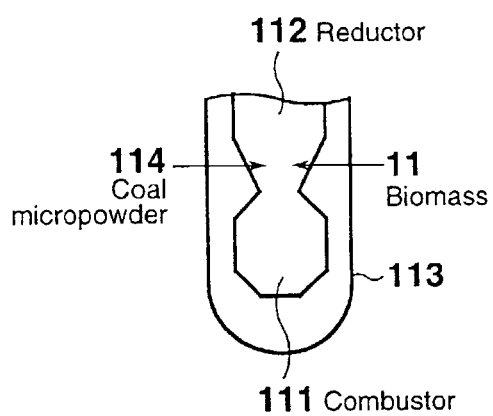
FIG. 27 is a schematic diagram illustrating a method for feeding coal micropowder and biomass according to the twenty-third embodiment.
Figure 27B:
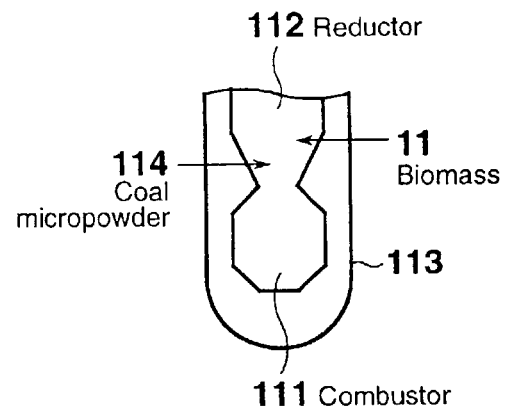

As shown in FIG. 27, in the case in which coal micropowder 114 and biomass 11 are fed separately, methods for feeding biomass include: (1) a method in which the coal micropowder 114 and the biomass 11 are fed through positions which are oppositely facing each other (as shown in FIG. 27(A)); or (2) an offset method in which the biomass 11 is fed through the position provided slightly above the position through which the coal micropowder 114 is fed (as shown in FIG. 27(B)). The coal micropowder or the biomass may be fed through a plurality of positions.

Figure 28:
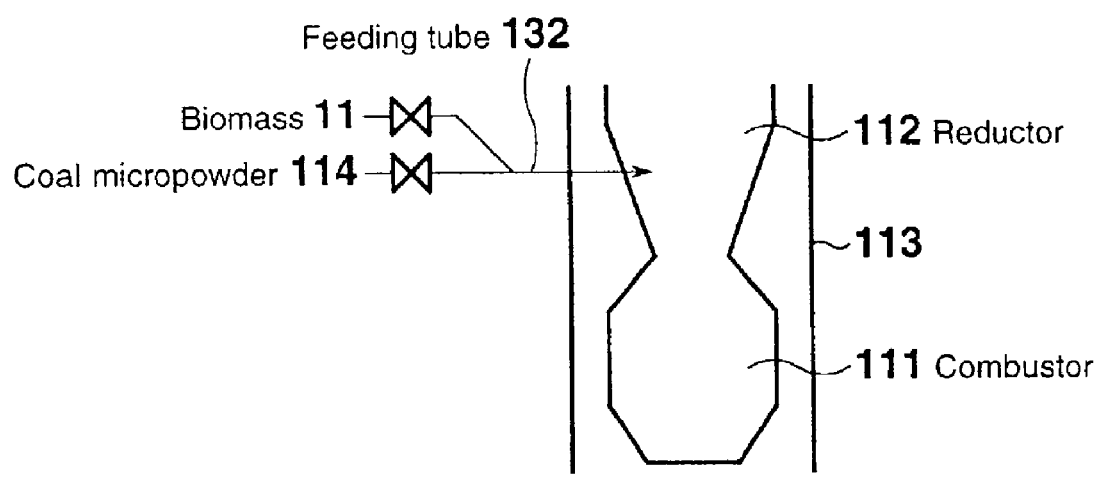
FIG. 28 is a schematic diagram illustrating an alternative method for feeding coal micropowder and biomass according to the twenty-third embodiment.

In addition to biomass feeding methods shown in FIG. 27, coal micropowder 114 and biomass 11 may be fed through a single feeding tube 132, as shown in FIG. 28.

Figures 29A, 29B:
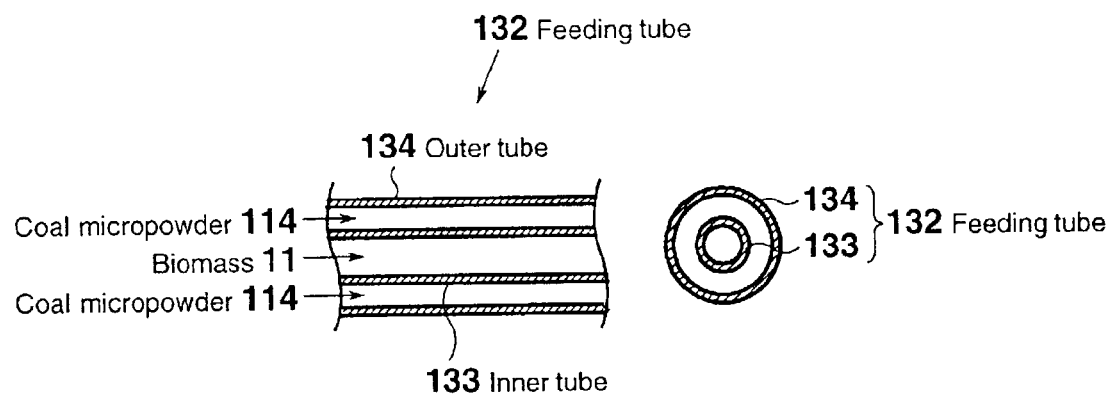
FIG. 29 is a schematic diagram of feeding tubes for feeding coal micropowder and biomass according to the twenty-third embodiment.

As shown in FIG. 29, the feeding tube 132 may have a dual structure in which tubes are provided concentrically, such that biomass 11 is fed through an inner tube 133 and the coal micropowder 114 is fed through an outer tube 134, to thereby inject them into the reductor 112.

As shown in FIG. 30, a biomass feeding portion 135 may further be provided above the reductor 112 in the combustion furnace 113 shown in FIG. 26, so as to feed biomass 11 to the biomass feeding portion 135. This structure can prevent combustion of the biomass 11 in the reductor 112, which may otherwise occur in a combustion furnace shown in FIG. 26. Therefore, gasification efficiency is improved.

In the present embodiment, as shown in FIG. 26, a steam reforming means 31 (for example, Ni-catalyst-carrying ceramic foam (a honeycomb-type radiation exchanger) 124) may be provided, according to needs, in the vicinity of the outlet of the combustion furnace, such that the ratio of $H_2$ to CO contained in a gas obtained through gasification in the combustion furnace 113 satisfies $2 < [H_2]/[CO]$.

Thus, the temperature in the reductor 112 of the combustion furnace 113, which is one factor of gasification conditions, is controlled to 700–1,200° C. (preferably about 800–1,000° C.).

This is because when the temperature in the furnace is lower than 700° C., combustion proceeds unsatisfactorily, whereas when the temperature is in excess of 1,200° C., soot is disadvantageously generated due to combustion of the biomass itself.

The superficial velocity in the combustion furnace 113, which is one factor of gasification conditions, is not particularly limited, and is preferably controlled to 0.1–5 m/s similar to that employed in the biomass gasification furnace described in the first embodiment.

In the above biomass gasification furnace 113, the gas 14 produced through gasification of biomass 11 may contain, other than the aforementioned $H_2$, CO, and $CO_2$, hydrocarbons such as $CH_4$, $C_2H_4$—$C_2H_6$, $C_3H_6$—, tar, and soot, depending on the gasification conditions.

Hydrocarbons such as the aforementioned $CH_4$ can be converted to CO and $H_2$ by means of the steam reforming means 31 at a temperature equal to or greater than 550° C. (suitably 900° C.±100° C.) in the presence of steam and a nickel catalyst. The $H_2$ obtained from the steam reforming means 31 can serve as a raw material for methanol synthesis as described above.

In other words, by adding the steam reforming means 31 for steam-reforming a gas 21 produced from the supplied biomass to a coal gasification system, CO and $H_2$ can be produced.

Thus, tar and soot, which are basically carbon-containing substances, can also undergo steam reforming if sufficient residence time is provided.

According to the aforementioned coal gasification furnace, since fed coal and biomass 11 are gasified, the gas produced through gasification has a compositional ratio of $H_2/CO$ greater than 2. Therefore, gasification and reforming are carried out efficiently, and a gas having an excellent composition for methanol synthesis can be obtained.

The produced gas is purified in the gas purification unit, and the compositional proportions of gas components in the gas are regulated, to thereby provide a raw material for the synthesis of various fuels (e.g., methanol and ethanol).

Figure 31:
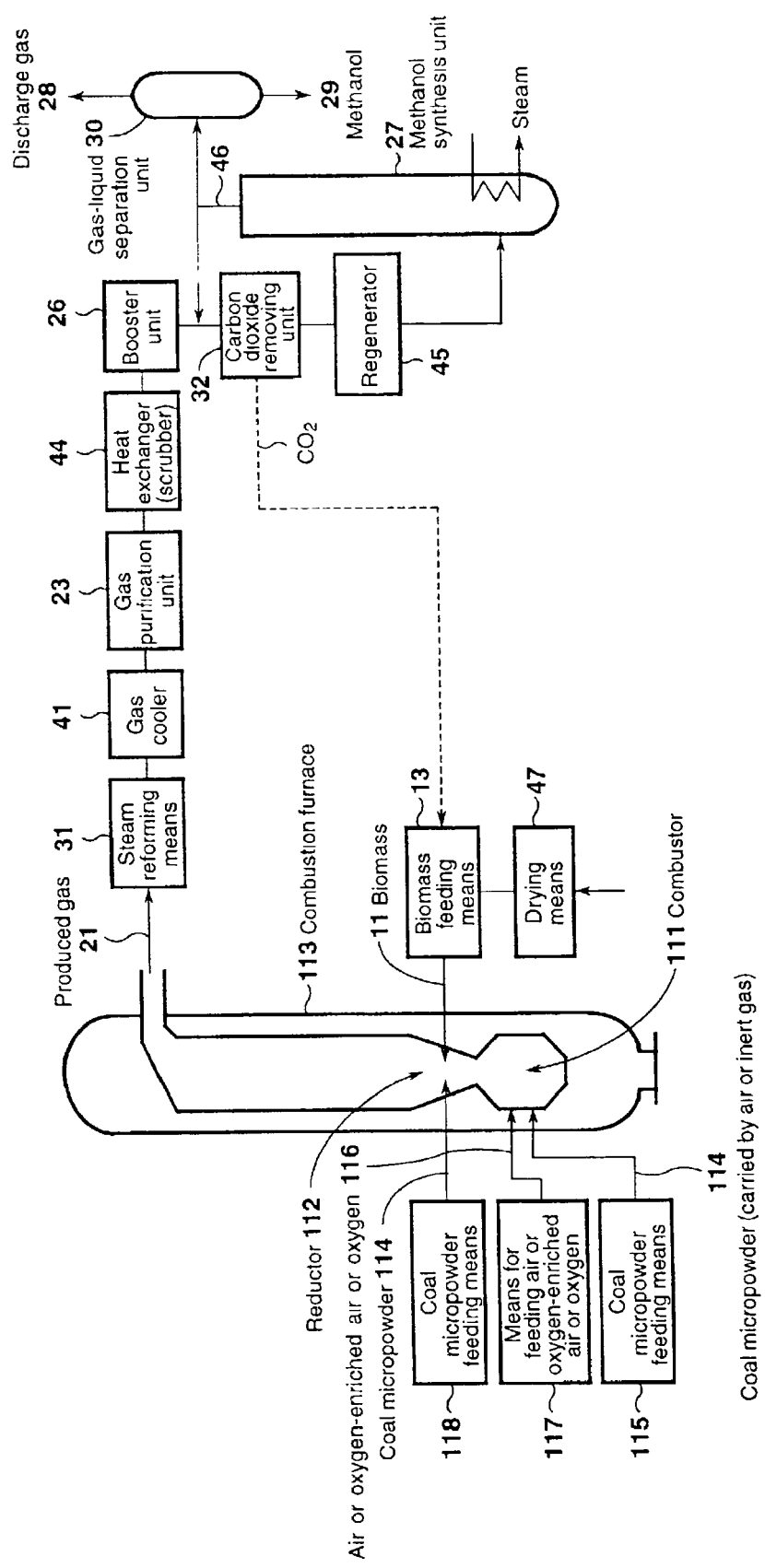
FIG. 31 is a schematic diagram of a methanol synthesis system employing a coal gasification furnace according to the twenty-third embodiment.

A system, according to the present embodiment, for synthesizing methanol for use as fuel will next be described with reference to FIG. 31. As shown in FIG. 31, the methanol synthesis system according to the present embodiment includes the aforementioned purification unit 23 for removing dust, etc. from the gas 21 produced in the combustion furnace 113 and cooled by means of a cooler 41, to thereby purify the gas; a heat exchanger 44 for removing steam from the purified gas; a booster unit 26 for increasing the pressure of the gas; a carbon dioxide removing unit 32 for removing $CO_2$ from the pressure-increased gas; a regenerator 45 for heating the carbon-dioxide-removed gas to the temperature for methanol production; a methanol synthesis unit 27 for producing methanol ($CH_3OH$) from $2H_2$ and CO contained in the gas; and a gas-liquid separation unit 30 for separating the gas 46 produced in the methanol synthesis unit 27 into methanol 29 and a discharge gas 28.

The above methanol synthesis system includes the carbon dioxide removing unit 32 for removing unnecessary $CO_2$ from the gas 21 produced through gasification, the gas containing CO, $CO_2$, and $H_2$. Therefore, excess $CO_2$ is removed from the system in a contacting manner at a final stage of the system by use of the carbon dioxide removing unit for removing $CO_2$, for example, an amine-wet-type carbon dioxide removing unit, to thereby increase the recovery percentage of methanol.

Thus, as shown in FIG. 31, the carbon dioxide removing unit 32 for removing $CO_2$ is provided between the booster unit 26 and the methanol synthesis unit 27, to thereby remove excess $CO_2$. Alternatively, the carbon dioxide removing unit 32 may be provided on the upstream side of the booster unit 26, to thereby increase the pressure of the gas from which $CO_2$ has been removed in advance.

Therefore, since excess $CO_2$ is removed from the methanol raw material gas fed to the methanol synthesis unit 27, the gas has a composition of CO and $2H_2$, to thereby efficiently effect methanol synthesis, i.e.; to attain high-efficiency synthesis.

$CO_2$ removed from the gas in the carbon dioxide removing unit 32 may be recycled as a carrier gas for the biomass.

According to the present invention, gasification of coal micropowder and biomass can be effectively performed. Thus, the gas composition of the produced gas becomes suitable for methanol synthesis.

In addition, as shown in FIG. 31, if necessary, the steam reforming means 31 may be provided at the outlet of the gasification furnace, to thereby reform, in the vicinity of the outlet of the gasification furnace, hydrocarbons contained in the produced gas 21 into CO and $H_2$ and attain a gas composition suitable for methanol synthesis.

$CO_2$, which is unnecessary for methanol synthesis, is removed by the carbon dioxide removing unit 32 to the outside, and the resultant gas contains CO and $2H_2$, which are required for methanol synthesis. The ratio of $H_2/CO$ in the gas becomes greater than 2, to thereby provide an remarkably ideal gas for methanol synthesis.

[Twenty-Fourth Embodiment]

A methanol synthesis system, according to the twenty-fourth embodiment of the present invention, employing a coal gasification furnace will be described with reference to FIG. 32.

Figure 32:
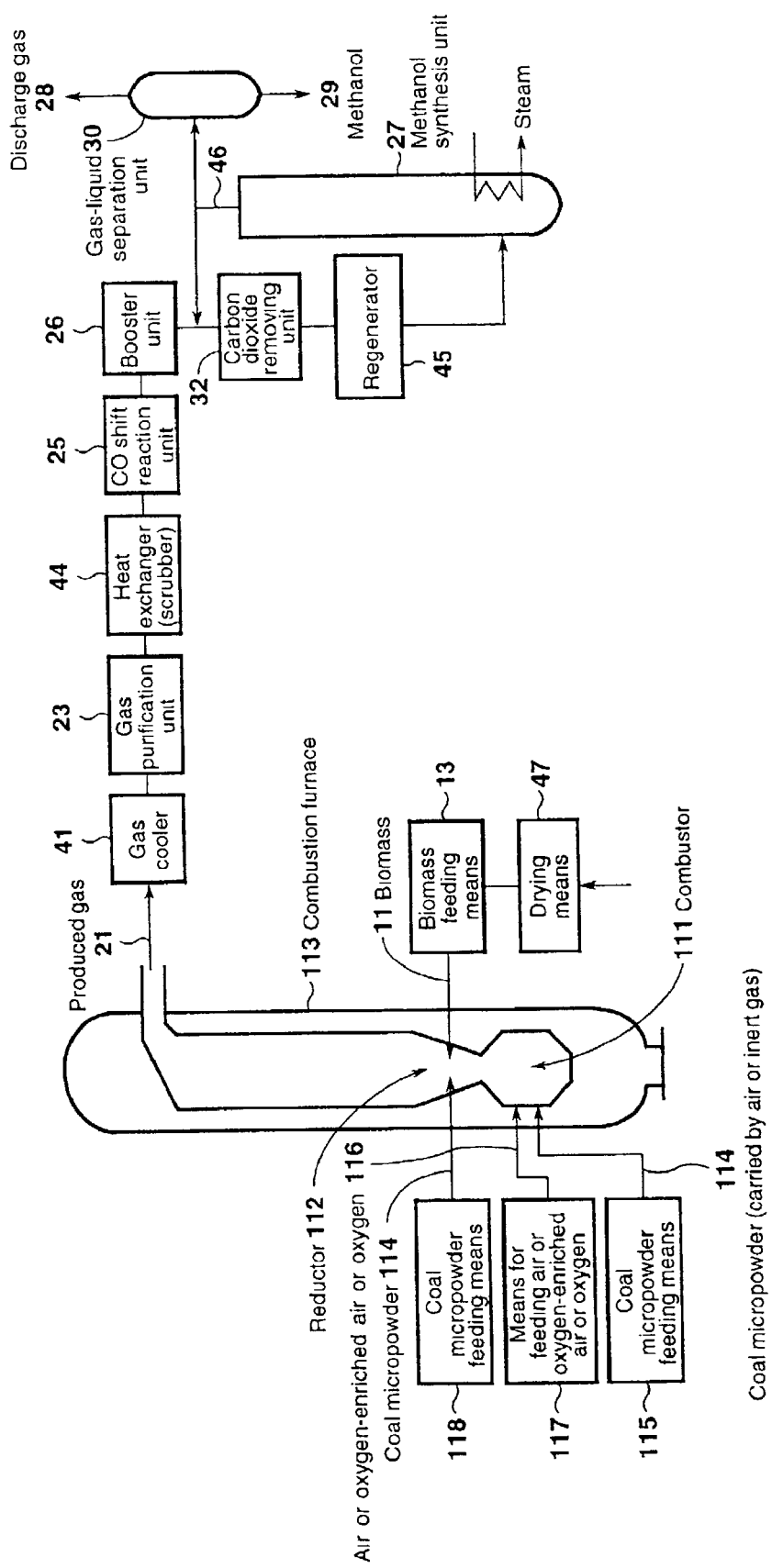
FIG. 32 is a schematic diagram of a methanol synthesis system employing a coal gasification furnace according to the twenty-fourth embodiment.

As shown in FIG. 32, the methanol synthesis system making use of biomass according to the present embodiment includes a combustion furnace 113 for gasifying fed biomass 11; a gas purification unit 23 for purifying the produced gas 21 obtained through gasification in the combustion furnace 113 and is cooled by means of a cooler 41; a heat exchanger 44 for removing steam from the purified gas; a CO shift reaction unit 25 for regulating the compositional ratio of $H_2$ to CO gas in the cooled gas; a booster unit 26 for increasing the pressure of the gas; a carbon dioxide removing unit 32 for removing $CO_2$ from the gas to the outside of the system; a regenerator 45 for heating the pressure-increased and $CO_2$-removed gas to the temperature for methanol production; a methanol synthesis unit 27 for producing methanol ($CH_3OH$) from $H_2$ and CO contained in the gas; and a gas-liquid separation unit 30 for separating a gas 46 synthesized in the methanol synthesis unit 27 into a discharge gas 28 and methanol 29.

In the aforementioned system shown in FIG. 31 according to the twenty-third embodiment, $CH_4$ contained in the gas produced through gasification is reformed into $H_2$ and CO through the steam reforming means 31. In contrast, in the system according to the present embodiment, $H_2$, which is essential for methanol synthesis, is obtained by use of the CO shift reaction unit 25. Although $CO_2$ is generated in the CO shift reaction unit 25, excess $CO_2$ is removed through separation of $CO_2$ by use of the carbon dioxide removing unit 32.

As described in connection with the first embodiment, $CO_2$ removed by the carbon dioxide removing unit 32 may be employed as a carrier gas for biomass 11.

[Twenty-Fifth Embodiment]

Figure 33:
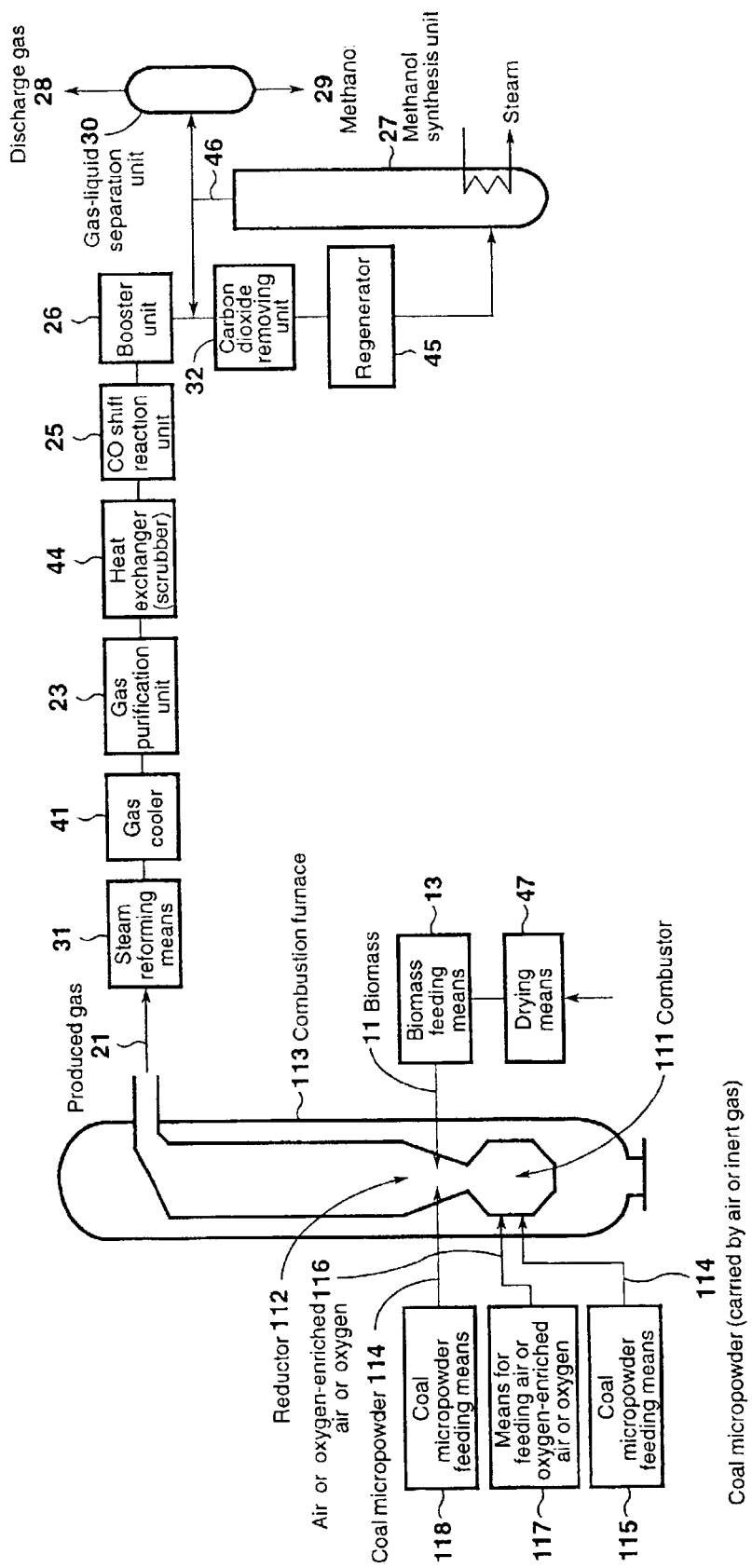
FIG. 33 is a schematic diagram of a methanol synthesis system employing a coal gasification furnace according to the twenty-fifth embodiment.

FIG. 33 shows a schematic diagram of a biomass gasification system employing a biomass gasification furnace according to the twenty-fifth embodiment.

As shown in FIG. 33, the methanol synthesis system, according to the present embodiment, making use of biomass includes a gasification combustion furnace 113 for gasifying fed biomass 11; a steam reforming means 31 for reforming hydrocarbons such as $CH_4$ contained in a gas 14 produced through gasification in the combustion furnace 113, in the presence of a nickel catalyst; a cooler 41 for cooling the gas which is reformed through the steam reforming means 31; a gas purification unit 23 for purifying the gas which has been cooled in the cooler 41; a heat exchanger 44 for removing steam from the purified gas; a CO shift reaction unit 25 for regulating the compositional ratio of $H_2$ to CO gas in the cooled gas; a booster unit 26 for increasing the pressure of the gas; a carbon dioxide removing unit 33 for removing $CO_2$ from the gas to the outside of the system; a regenerator 45 for heating the pressure-increased and CO2-removed gas to the temperature for methanol production; a methanol synthesis unit 27 for producing methanol ($CH_3OH$) 29 from $H_2$ and CO contained in the gas; and a gas-liquid separation unit 30 for separating a gas 46 synthesized in the methanol synthesis unit 27 into a discharge gas 28 and methanol 29.

In the above-described twenty-third embodiment, $CH_4$ contained in the gas produced through gasification is reformed into $H_2$ and CO through reformation by means of the steam reforming means 31. In the present embodiment, $H_2$, which is necessary for methanol synthesis, is obtained in a large amount by use of the CO shift reaction unit 25. Although $CO_2$ is generated in the CO shift reaction unit 25, excess $CO_2$ is removed through separation of $CO_2$ by use of the carbon dioxide removing unit 32.

[Twenty-Sixth Embodiment]

In the biomass gasification furnaces according to the first and the fourteenth through the twenty-first embodiments, the to-be-gasified biomass serving as a raw material is efficiently gasified by employment of a combination of combustion and gasification of biomass fed to a furnace. The present invention alternatively provides another configuration of biomass gasification in which combustion and gasification are carried out efficiently in a separate field.

In such a biomass gasification furnace, biomass (e.g., in the form of plants) is subjected to partial oxygen gasification. Specifically, exothermic reaction (combustion reaction) of biomass represented by the below-described formula (A) and endothermic reaction (thermal decomposition reaction) of biomass represented by the below-described formula (B) are carried out in combination in one chamber, to thereby gasify the biomass. In relation to gas produced through the combination reaction, the proportions of gas components in the synthesis gas; i.e., $CO/H_2/CO_2$ (by mol), are preferably 0.9–1.0/1.8–2.2/about 1.

$$CH_2O+1/2O_2 \rightarrow CO_2+H_2 \quad \text{formula (A)}$$

$$CH_2O \rightarrow CO+H_2 \quad \text{formula (B)}$$

A typical form of biomass ($C_mH_2O_n$) is represented by $CH_2O$.

In the aforementioned biomass gasification furnace, exothermic reaction of biomass and endothermic reaction of biomass, which are counteractive to each other, are carried out in combination in one chamber. Therefore, the following problems arise.

In order to attain the aforementioned combination reaction and to produce a desired gas form, exothermic reaction and endothermic reaction, which are counteractive to each other, must be carried out and controlled promptly. Therefore, from the viewpoints of heat generation (combustion) and heat absorption (thermal decomposition), biomass must be formed into fine particles (particle size: tens of microns). However, when fibrous biomass is formed into fine particles, the type of pulverizing machine is limited, and the pulverization power unit must be large. In accordance with the size of biomass fine particles, the system for powder handling, including storage, discharge, transportation, and supply of the powder of biomass, becomes complicated, and may encounter difficulty.

Since exothermic reaction of biomass and endothermic reaction of biomass, which are counteractive to each other, must be carried out simultaneously and in combination, control of the reactions becomes complex.

When the aforementioned biomass gasification furnace is employed in a methanol production unit, control of the reactions becomes similarly complicated.

An object of the invention is to provide a biomass gasification furnace which is easily controlled and which eliminates the necessity of pulverizing biomass into fine particles.

Another object of the invention is to provide a methanol production unit which is easily controlled, which unit employs the biomass gasification furnace which is easily controlled, and which eliminates the necessity of pulverizing biomass into fine particles.

Figure 34:
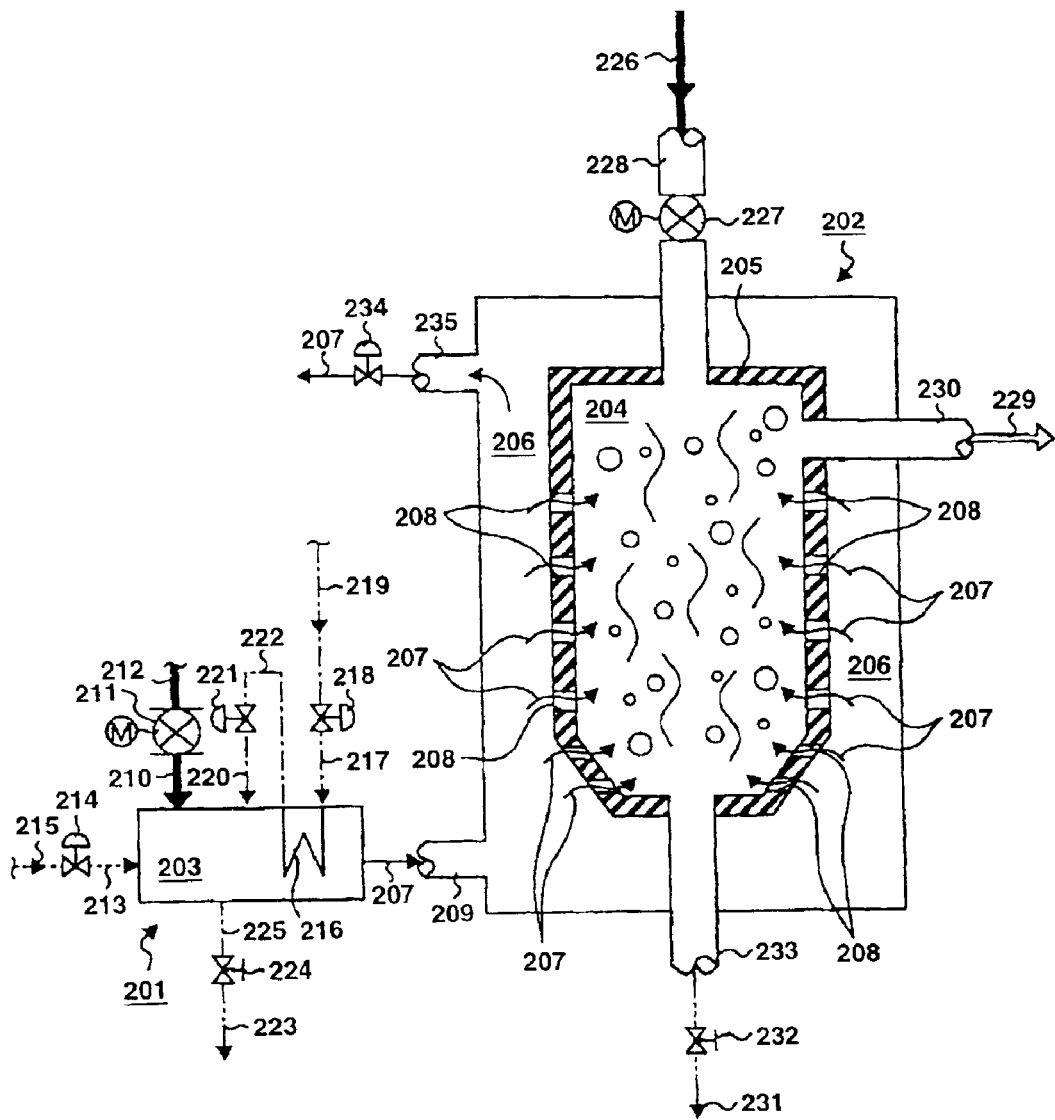
FIG. 34 is a schematic diagram of a biomass gasification furnace according to the twenty-sixth embodiment.

FIG. 34 schematically depicts a twenty-sixth embodiment of the biomass gasification furnace according to the invention. In FIG. 34, reference numerals 201 and 202 represent a combustion chamber and a gasification chamber, respectively, the chambers being provided separately. A combustion space 203 is provided in the combustion chamber 201. A gasification space 204 is provided in the gasification chamber 202.

A reaction tube 205 formed from a heat-resistant material is provided in the gasification chamber 202. The gasification space 204 is provided in the reaction tube 205. A combustion gas feeding passage 206 is provided between the inside wall surface of the gasification chamber 202 and the outside wall surface of the reaction tube 205. The reaction tube 205 includes a large number of perforations 208 for uniformly feeding a combustion gas 207 (represented by a solid arrow in FIG. 34) from the combustion gas feeding passage 206 to the reaction tube 205. The gasification chamber 202 and the reaction tube 205 have a dual-tube structure.

A combustion gas feeding line 209 for feeding the combustion gas 207 from the combustion space 203 to the gasification space 204 is provided between the combustion space 203 in the combustion chamber 201 and a portion of the combustion gas feeding passage 206 located at a lower portion of the gasification chamber 202.

A feeding unit 211 and a feeding line 212 for feeding biomass 210 for combustion (represented by a thick solid arrow in FIG. 34) are connected to the upper portion of the combustion chamber 201. A discharge valve 224 and a discharge line 225 for discharging ash 223 (represented by a two-dot arrow in FIG. 34) are connected to the bottom of the combustion chamber 201. In addition, a feeding control valve 214 and a feeding line 215 for feeding an oxidizing agent 213 (represented by a dashed arrow in FIG. 34) such as oxygen or air are connected to the lower portion of the combustion chamber 201.

In the combustion chamber 201, a heat exchanger 216 serving as heat recovery means is provided on the side close to the combustion gas feeding line 209. The heat exchanger 216 has the ability to absorb heat by use of water and to remove dust. A flow control valve 218 and a feeding line 219 for feeding water 217 (represented by a one-dot arrow in FIG. 34) are connected to the heat exchanger 216. A pressure control valve 221 and a feeding line 222 for feeding steam 220 (represented by a one-dot arrow in FIG. 34) are connected between the heat exchanger 216 and the upper portion of the combustion chamber 201. The steam feeding line 222 is connected to the upper portion of the combustion chamber 201 at a location between the feeding line 212 for feeding biomass for combustion and the heat exchanger 216. The steam feeding line 222 may be branched, and the branched line may be connected to the lower portion of the combustion chamber 201 via a pressure control valve (not illustrated).

A feeding unit 227 and a feeding line 228 for feeding biomass 226 for gasification (represented by a thick solid arrow in FIG. 34) are connected through the gasification chamber 202 to the top of the reaction tube 205. A discharge line 230 for discharging a synthesized gas 229 (represented by an outlined arrow or a double-solid arrow in FIG. 34) is connected to the upper portion of the reaction tube 205. In addition, a discharge valve 232 and a discharge line 233 for discharging ash 231 (represented by a two-dotted arrow in FIG. 34) are connected through the gasification chamber 202 to the bottom of the reaction tube 205. Further, a control valve 234 and a discharge line 235 for discharging the combustion gas 207 are connected to a portion of the combustion gas feeding passage 206 located at the upper portion of the gasification chamber 202.

Heat exchangers (not illustrated), serving as heat recovery means, may be provided on the discharge line 230 for the synthesis gas 229 and on the discharge line 235 for the combustion gas 207, to thereby feed the water 217 to the heat exchanger 216 in the combustion chamber 201 through the heat exchangers on the synthesis gas discharge line 230 and on the combustion gas discharge line 235. Means for recovering the non-reacted biomass 226 for gasification; for example, a cyclone (not illustrated), may be provided between the reaction tube 205 and the discharge line 230 for the synthesis gas 229. An opening (not illustrated) for feeding the biomass 210 for combustion may be provided on the combustion chamber 201, and an opening and closing cap (not illustrated) may be provided on the opening such that the opening can be opened and closed.

Operation of the biomass gasification furnace of the twenty-sixth embodiment having the aforementioned structure will next be described.

The biomass 210 for combustion and the oxidizing agent 213 are fed to the combustion space 203 in the combustion chamber 201. The biomass 210 is combusted in the combustion space 203, in which the ratio, the oxidizing agent 213/the biomass 210, is 0.5–0.7. Combustion of the biomass 210 is carried out through ignition by use of an ignition burner (not illustrated).

Through combustion of the biomass 210, the combustion gas 207 is generated in the combustion space 203. The steam 220 is fed to the combustion chamber 201. Through feeding of the steam 220, generation of carbon or soot, which may be generated through combustion of the biomass 210 in the combustion space 203, can be suppressed. Steam is suitably employed particularly in the gasification furnace according to the twenty-sixth embodiment, in which the combustion gas 207 in the combustion space 203 is fed, as a heat source, to the gasification space 204.

The combustion gas 207 containing the steam 220 has a temperature of 800–1,100° C., which is suitable for gasification (thermal decomposition) of the below-described biomass 226 for gasification, and has a calorific value necessary for the gasification; i.e., a calorific value two to three times the product of the amount of the biomass 226 and the reaction heat absorption value. The temperature and the calorific value of the combustion gas 207 containing the steam 220 are controlled by regulation of (the oxidizing agent 213)/(the biomass 210) ratio, regulation of the amount of water 217 fed to the heat exchanger 216, or regulation of the amount of the steam 220 fed to the combustion chamber 201.

In the combustion space 203, by the dust removal effect of the heat exchanger 216, biomass and ash dispersed in the combustion space 203 are removed, to thereby prevent the flow of such dust into the gasification chamber 202 provided on the downstream side of the combustion chamber. Such a heat exchanger is suitably employed particularly in the gasification furnace according to the twenty-sixth embodiment, in which the combustion gas 207 produced in the combustion space 203 is fed, as a heat source, to the gasification space 204.

The residual ash 223 of the biomass 210 combusted in the combustion space 203 is precipitated and accumulated at the bottom of the combustion chamber 201. The precipitated and accumulated ash 223 is periodically discharged through the discharge valve 224 and the discharge line 225 to the outside of the combustion chamber 201.

The combustion gas 207 containing the steam 220 is fed through the combustion gas feeding line 209 to a portion of the combustion gas feeding passage 206 located at the lower portion of the gasification chamber 202. At the inlet of the gasification chamber 202, preferably, the combustion gas 207 containing the steam 220 has a temperature of 600–1,000° C. and has a gas form containing no non-reacted carbon and a small amount of $H_2O$, in which the mol ratio of $CO_2/H_2$ is 0.9–1.1 (preferably 1). When air is used as the oxidizing agent 213, the combustion gas 207 containing the steam 220 naturally contains inert $N_2$ gas.

In accordance with the form of the below-described biomass 226 for gasification, the amount and the pressure of the combustion gas 207 containing the steam 220 at the inlet of the gasification chamber 202 are regulated by the control valve 234 of the discharge line 235 for the combustion gas 207.

The biomass 226 for gasification is fed to the gasification space 204 in the reaction tube 205 of the gasification chamber 202. In the gasification space 204, gasification (i.e., thermal decomposition, hereinafter referred to as "gasification") of the biomass 226 proceeds while the biomass 226 is caused to flow by the combustion gas 207 containing the steam 220. The pressure of the gasification space 204 in the reaction tube 205 is generally maintained at ambient pressure to 10 ata.

In the reaction tube 205, the flow velocity (superficial velocity) of the biomass 226 for gasification is preferably about 0.1 m/s or less. The flow velocity of the biomass 226 is set at the above value, in order to prevent dispersion of the biomass 226 and the ash remaining after gasification to the outside of the reaction tube 205, and to secure a sufficient reaction time (about 30–60 seconds), over which the biomass 226 stays within the reaction tube 205 for gasification.

The reaction tube 205 includes a large number of perforations 208, so that the combustion gas 207 is uniformly fed to the interior of the reaction tube 205. Owing to this structure of the tube 205, the biomass 226 for gasification is uniformly gasified in the reaction tube 205. Therefore, the efficiency of gasification of the biomass 226 is enhanced.

In the reaction tube 205, the biomass 226 for gasification is gasified, to thereby produce the synthesis gas 229 predominantly containing CO, $H_2$, $CO_2$, and $H_2O$ (and $N_2$ when combustion is effected in the presence of air). In the biomass gasification furnace according to the twenty-sixth embodiment, the combustion gas 207 ($CO_2$, $H_2$) produced in the combustion chamber 201 which is provided separately from the gasification chamber is fed to the reaction tube 205, and the combustion gas is mixed with the gas (CO, $H_2$) produced through gasification of the biomass 226, to thereby obtain the synthesis gas 229 ($CO_2$, CO, $2H_2$). In the biomass gasification furnace according to the twenty-sixth embodiment, the calorific value necessary for gasification of the biomass 226, which is generally an endothermic reaction, is obtained from the combustion gas 207 produced in the combustion chamber 201 which is provided separately from the gasification chamber.

In the synthesis gas 229, the mol proportions of the gas components CO, $H_2$, and $CO_2$ are preferably 0.9–1.0/1.8–2.2/about 1. Particularly, from the viewpoint that methanol is synthesized from the synthesis gas 229, the mol ratio of $CO/H_2$ must be ½. In the biomass gasification furnace according to the twenty-sixth embodiment, the mol proportions of the gas components in the synthesis gas 229 are regulated by control of gasification (basically, control of the form of the biomass 226 serving as a raw material) in the reaction tube 205 of the gasification chamber 202, and by control of combustion in the combustion chamber 201 serving as a heat feeding source.

Combustion in the combustion chamber 201 is controlled by, for example, regulation of the amount of the biomass 210 for combustion, regulation of the ratio of the oxidizing agent 213, regulation of the amount of the steam 220 for temperature control, and regulation of the heat exchanger 216 for calorie control.

H-65)

The synthesis gas 229 produced in the reaction tube 205 is fed through the discharge line 230 to a unit provided downstream; for example, a methanol synthesis unit (not illustrated). Excess gas of the combustion gas 207 serving as a heat source of gasification is discharged through the control valve 234 and the discharge line 235 to the outside of the gasification chamber 202. When heat exchangers serving as heat recovery means are provided on the discharge line 230 and the discharge line 235, discharged heat can be recovered. The excess gas (the combustion gas 207) may be utilized as a heat source for increasing the reaction temperature of a catalyst (i.e. a heat source for heating a catalyst) in a methanol synthesis unit. Alternatively, the excess gas (the combustion gas 207) may be recovered through a recovery line (not illustrated) to the combustion space 203 in the combustion chamber 201.

Reaction residual ash 231 resulting from the reaction of the to-be-gasified biomass 226 in the gasification space 204 of the reaction tube 205 is discharged intermittently, to the outside of the gasification chamber 202, from the lower portion of the reaction tube 205 through the discharge line 233 and the discharge valve 232.

The biomass gasification furnace according to the twenty-sixth embodiment includes the combustion chamber 201 and the gasification chamber 202, which are provided separately, in which the combustion space 203 for combusting the to-be-combusted biomass 210 and the gasification space 204 for gasifying the to-be-gasified biomass 226 are provided, respectively.

As a result, in the biomass gasification furnace according to the twenty-sixth embodiment, exothermic reaction of biomass and endothermic reaction of biomass, which are counteractive to each other, are carried out independently in the combustion space 203 and the gasification space 204, respectively. Thus, biomass is not necessarily pulverized (to some tens of microns) in order to cause the counteractive exothermic and endothermic reactions promptly. Particularly, the particle size of to-be-gasified biomass 226 in the order of a few millimeter is sufficient. Furthermore, the biomass gasification furnace according to the twenty-sixth embodiment is easily controlled, since the counteractive reactions, exothermic and endothermic reactions of biomass, can be controlled independently.

In the biomass gasification furnace according to the twenty-sixth embodiment, the melting point of the ash 231 of the biomass 226 for gasification varies within a range of 750–1,500° C., in accordance with the type of the biomass 226. When the melting point of the ash 231 is sufficiently high (e.g.; 900° C. or higher) with respect to the gasification temperature (700–900° C.), there hardly arises the problem that the ash 231 is melted in the reaction tube 205, and thus flow of the biomass 226 is impeded and discharge of the ash 231 becomes difficult. However, when the melting point of the ash 231 is 900° C. or lower, the aforementioned problems in relation to melting of the ash 231 may arise, because of the relationship between the melting point of the ash and the gasification temperature.

In the biomass gasification furnace according to the twenty-sixth embodiment, such a problem can be prevented by lowering the gasification temperature, while sacrificing the gasification reaction to some extent. In the biomass gasification furnace according to the twenty-sixth embodiment, since exothermic reaction of biomass and endothermic reaction of biomass are controlled individually, such a problem can be solved.

[Twenty-Seventh Embodiment]

Figure 35:
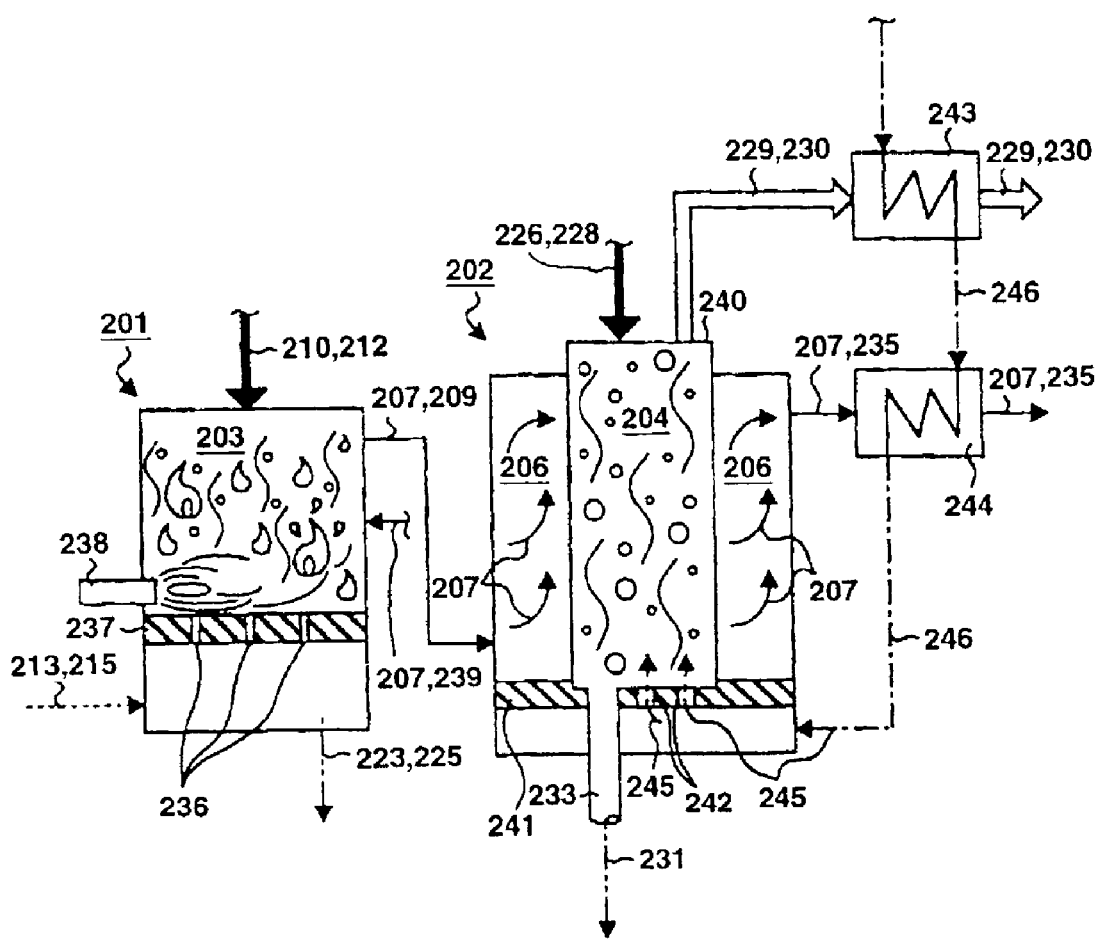
FIG. 35 is a schematic diagram of a biomass gasification furnace according to the twenty-seventh embodiment.

FIG. 35 schematically depicts the biomass gasification furnace according to Embodiment 27 of the present invention. In FIG. 35, reference numerals identical with those in FIG. 34 represent the same components.

A grate 237 having a large number of perforations 236 is provided at the lower portion of a combustion chamber 201. An ignition burner 238 is also provided at the lower portion of the combustion chamber 201. A recovery line 239 for a combustion gas 207 is provided at the upper portion of the combustion chamber 201.

A line (not illustrated) for feeding steam to suppress generation of carbon or soot may be provided in a combustion space 203 of the combustion chamber 201. A heat recovery means (not illustrated) and/or a dust removing means (not illustrated) may be provided in the combustion space 203 of the combustion chamber 201. In addition, an opening (not illustrated) for feeding biomass 210 for combustion may be provided on the combustion chamber 201, and an opening and closing cap (not illustrated) may be provided on the opening such that the opening can be opened or closed.

A reaction tube 240 is provided in a gasification chamber 202. The reaction tube 240 is formed of a metallic tube, for example, a quartz tube or a Pyrex glass tube.

A receiving plate 241 is provided at the lower portion of the gasification chamber 202. The lower portion of the reaction tube 240 is held by the receiving plate 241. A large number of perforations 242 are provided in the receiving plate 241, so as to communicate with the reaction tube 240.

Heat exchangers 243 and 244, serving as heat recovery means, are provided on a discharge line 230 for a synthesis gas 229 and on a discharge line 235 for the combustion gas 207, respectively. A feeding line 246 for feeding steam 245 (represented by a one-dot arrow in FIG. 35) is connected between the heat exchangers 243 and 244 and the lower portion of the gasification chamber 202. The steam 245 is heated steam having a temperature of 400–500° C. Cooling water is heated in the heat exchanger 243, to thereby form steam, and the resultant steam is heated in the heat exchanger 244 to obtain heated steam.

Means for recovering non-reacted biomass 226 for gasification; for example, a cyclone (not illustrated), may be provided between the reaction tube 240 and the discharge line 230 for the synthesis gas 229.

Operation of the biomass gasification furnace according to the twenty-seventh embodiment having the aforementioned structure will next be described.

In the combustion space 203 of the combustion chamber 201, granular or chip-like biomass 210 for combustion is completely combusted through ignition by the ignition burner 238 and by use of an oxidizing agent 213 fed through the perforations 236 in the grate 237 provided at the lower portion of the combustion chamber 201. While maintaining a predetermined temperature (about 800–1,100° C.) and calorific value, the completely combusted clean combustion gas 207 is fed to a gas feeding passage 206 of the gasification chamber 202. The temperature and the calorific value of the combustion gas 207 are controlled by the aforementioned regulation.

The heat of the combustion gas 207 fed to the gas feeding passage 206 is supplied from the outside of the reaction tube 240 to the inside thereof. The biomass 226 for gasification is fed to the reaction tube 240 from the upper portion, and the steam 245 containing no oxygen (the steam 245 is a gasification agent and heated steam having a temperature of 400–500° C.) is fed upward to the reaction tube 240 from the lower portion. As a result, while the biomass 226 is caused to flow by the steam 245, the biomass 226 is gasified by the radiation heat of the reaction tube 240, to thereby produce the synthesis gas 229.

In general, the aforementioned reaction in which biomass ($C_mH_2O_n$) serves as a raw material and steam ($H_2O$) serves as a gasification agent includes elementary reactions represented by the following formulas (C), (D), and (E).

$$CO+H_2O \rightarrow CO_2+H_2 \quad \text{formula (C)}$$

$$C+H_2O \rightarrow CO+H_2 \quad \text{formula (D)}$$

$$C+2H_2O \rightarrow CO_2+2H_2 \quad \text{formula (E)}$$

In order to synthesize methanol from the synthesis gas 229, the mol ratio of $CO/H_2$ is preferably ½. Therefore, in order to smoothly carry out the above-described reactions represented by formulas (C), (D), and (E), some regulation means are necessary. As one such regulation means, the inner temperature of the reaction tube 240 is regulated. The temperature is regulated at 700–1,000° C., preferably 700–900° C., more preferably 700–800° C. The inner temperature of the reaction tube 240 is controlled by regulation of the amount and the temperature of the combustion gas 207 and by regulation of the amount and temperature of the steam 245.

The synthesis gas 229 which is produced in the reaction tube 240 and is accompanied by some dispersion granules is fed through the discharge line 230 and the heat exchanger 243 to a unit provided downstream; for example, a methanol synthesis unit (not illustrated). Excess gas of the combustion gas 207 serving as a heat source of gasification is discharged through the discharge line 235 and the heat exchanger 244 to the outside of the gasification chamber 202. The excess gas (the combustion gas 207) may be utilized as a heat source for increasing the reaction temperature of a catalyst (i.e., a heat source for heating a catalyst) in a methanol synthesis unit. Alternatively, the excess gas (the combustion gas 207) may be recovered through a recovery line (not illustrated) to the combustion space 203 in the combustion chamber 201.

The residual ash 223 of the biomass 210 combusted in the combustion space 203 is precipitated and accumulated at the bottom of the combustion chamber 201. The precipitated and accumulated ash 223 is intermittently discharged through the discharge line 225 to the outside of the combustion chamber 201. The residual ash 231 of the biomass 226 which is subjected to reaction in the gasification space 204 in the reaction tube 240 is intermittently discharged from the lower portion of the reaction tube 240 through the discharge line 233 to the outside of the gasification chamber 202.

As described above, since the gasification furnace according to the present embodiment has the aforementioned structure, the gasification furnace according to the twenty-seventh embodiment provides operation and effects similar to those of the gasification furnace according to the twenty-sixth embodiment.

Particularly, in the gasification furnace according to the twenty-seventh embodiment, only the steam 245 is fed, as a gasification agent, to the reaction tube 240 and an oxidizing agent is not necessary, since the gasification space 204 in the reaction tube 240 is separated from the combustion gas feeding passage 206. Since the steam 245 contains no oxygen, problems caused by generation of $CO_2$ can be prevented. In the gasification furnace according to the twenty-seventh embodiment, the biomass 210 for combustion is completely combusted in the combustion space 203 of the combustion chamber 201, and the clean combustion gas 207 can be fed to the gasification space 204 in the reaction tube 240. In the gasification furnace according to the present embodiment, a great difference in form between the biomass 210 for combustion and the biomass 226 for gasification does not raise any problem. For example, wood chips are employed as the biomass 210 for combustion. In contrast, as the biomass 226 for gasification, biomass powder having a size of 5–10 mm or less, preferably about 1 mm, is employed. Alternatively, slurry in which the powder and water are mixed is employed as the biomass 226.

[Twenty-Eighth Embodiment]

Figure 36:
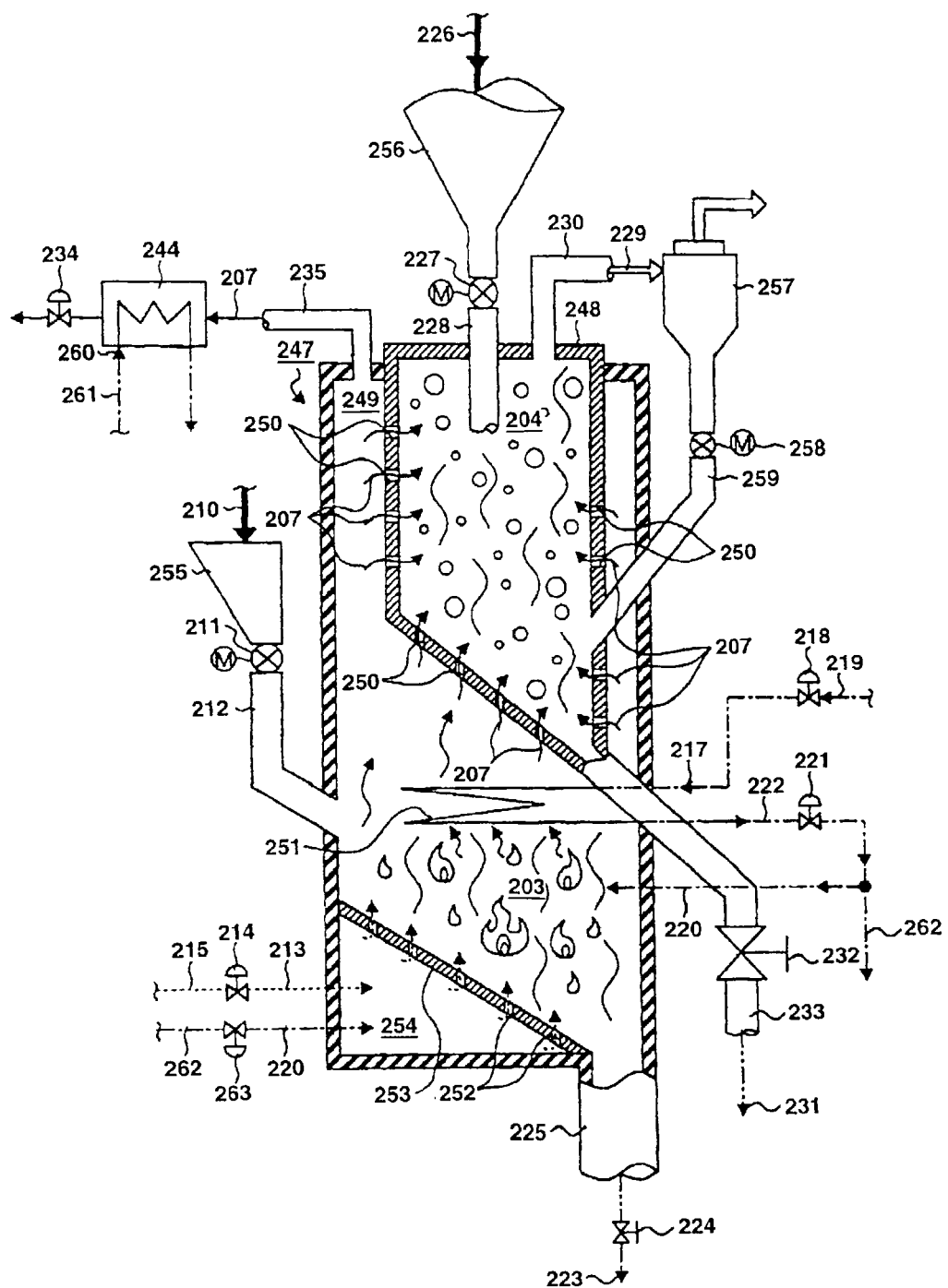
FIG. 36 is a schematic diagram of a biomass gasification furnace according to the twenty-eighth embodiment.

FIG. 36 schematically depicts a biomass gasification furnace according to Embodiment 28 of the present invention. The gasification furnace according to the twenty-eighth embodiment is a modification of the gasification furnace according to the twenty-sixth embodiment. In FIG. 36, reference numerals identical with those in FIG. 34 and FIG. 35 represent the same components.

In the biomass gasification furnace, a combustion space 203 and a gasification space 204 are separated from each other, and these spaces are provided at the lower and upper portions of a chamber 247. A reaction tube 248 is provided in the chamber 247. The gasification space 204 is provided in the reaction tube 248. A combustion gas feeding passage 249 is provided between the inside wall surface of the chamber 247 and the outside wall surface of the reaction tube 248. The reaction tube 248 includes a large number of perforations 250 for uniformly feeding the combustion gas 207 from the combustion gas feeding passage 249 to the interior of the reaction tube 248. A horizontal-type heat exchanger 251 (heat recovery means and dust removing means) is provided above the combustion space 203.

In the chamber 247, the space between the combustion space 203 and the combustion gas feeding passage 249 serves as a combustion gas feeding line.

A grate 253 having a large number of perforations 252 is provided at the lower portion of the chamber 247. A wind box 254 for feeding an oxidizing agent and steam is provided between the grate 253 and the chamber 247. Feeding hoppers 255 and 256 are provided on a feeding line 212 for biomass 210 for combustion and on a feeding line 228 for biomass 226 for gasification, respectively. Means for recovering the non-reacted biomass 226 for gasification is provided between a discharge line 230 for a synthesis gas 229 and the reaction tube 248. The means includes a cyclone 257, a circulation-feeding valve 258, and a circulation-feeding line 259.

A line 261 for feeding cooling water 260 is connected to a heat exchanger 244 provided on a discharge line 235 for the combustion gas 207. A flow control valve 218 and a feeding line 219 for feeding water 217 or steam 220 are provided between the heat exchanger 244 and the heat exchanger 251. A pressure control valve 221 and a feeding line 222 for feeding the steam 220 are provided between the heat exchanger 251 and the combustion space 203. The feeding line 222 is branched. A branch line 262 of the feeding line 222 is connected through a valve 263 to the wind box 254 for feeding an oxidizing agent and steam, to thereby feed the steam 220 to the wind box 254.

Since the biomass gasification furnace according to the twenty-eighth embodiment has the aforementioned structure, the biomass gasification furnace according to the twenty-eighth embodiment provides operation and effects similar to those of the biomass gasification furnace according to the twenty-sixth and the twenty-seventh embodiments.

Particularly, according to the twenty-eighth embodiment, the entire structure of the biomass gasification furnace is simplified, since the combustion space 203 and the gasification space 204 are provided in the chamber 247 while these spaces are separated from each other. The biomass gasification furnace according to the present embodiment includes the means 257, 258, and 259 for recovering non-reacted biomass for gasification. Therefore, adverse effects of non-reacted granular biomass on units provided downstream can be prevented, and fed biomass can be completely gasified.

[Twenty-Ninth Embodiment]

Figure 37:
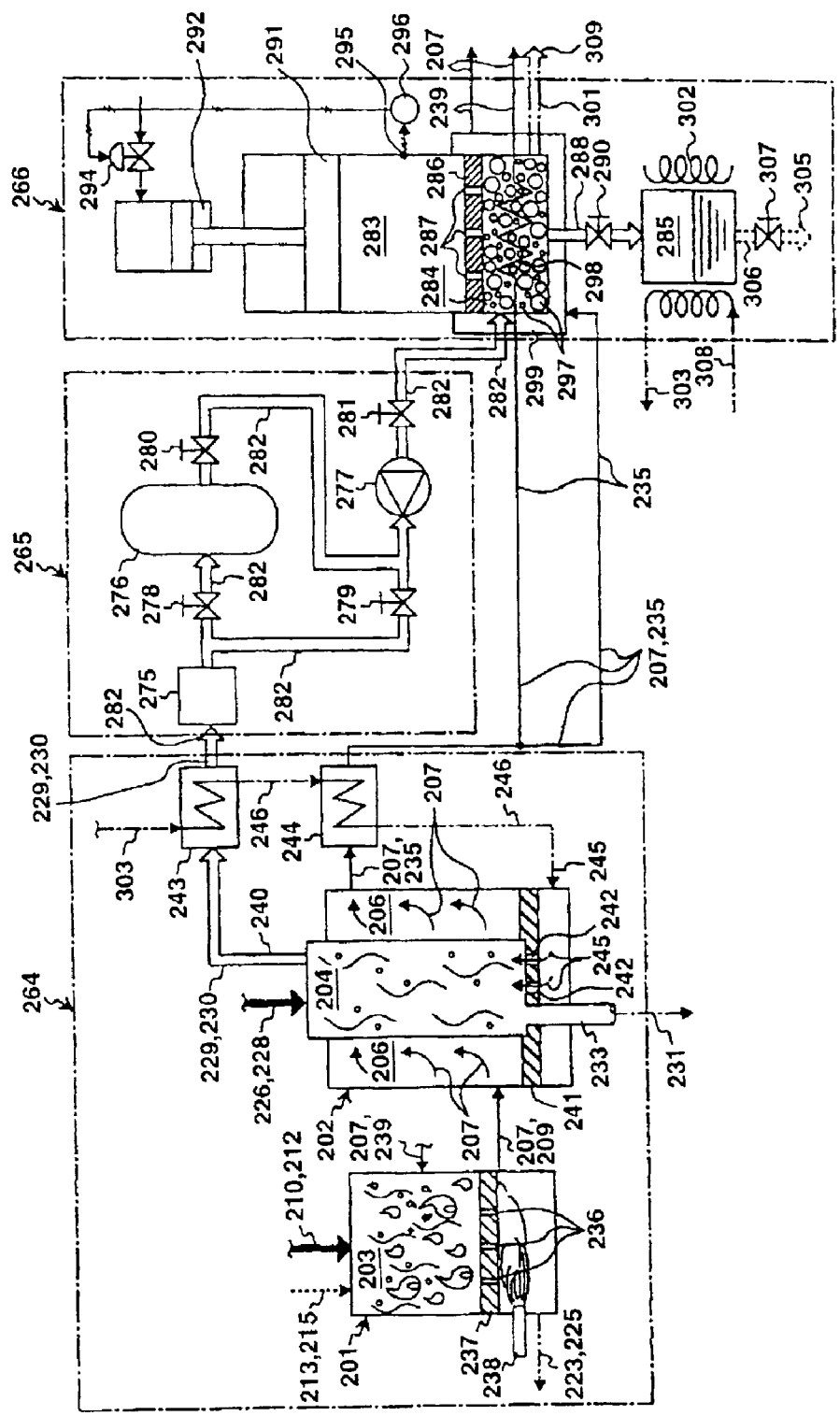
FIG. 37 is a schematic diagram showing a methanol synthesis system equipped with a biomass gasification furnace according to the twenty-ninth embodiment.
Figure 38:
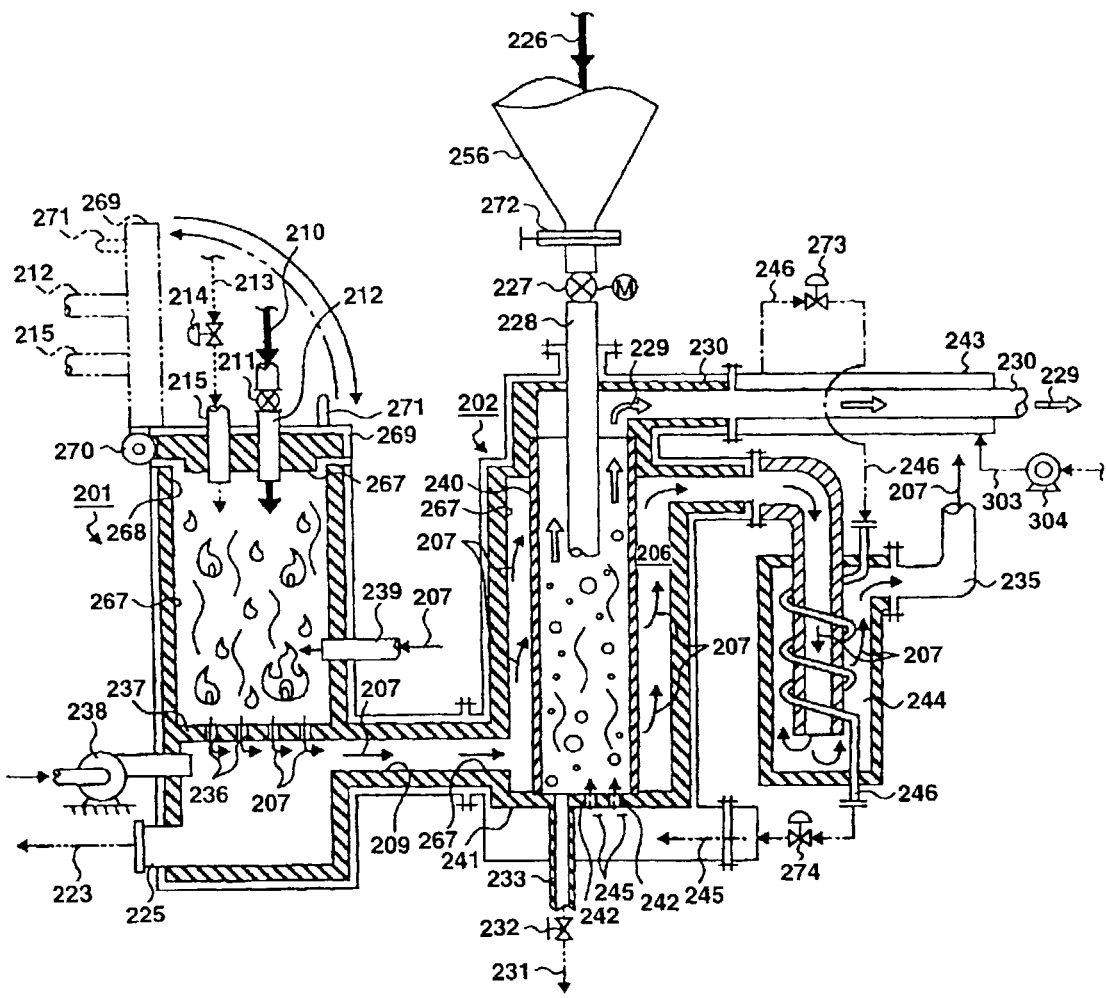
FIG. 38 is a schematic diagram of a biomass gasification furnace according to the twenty-ninth embodiment.
Figure 39:
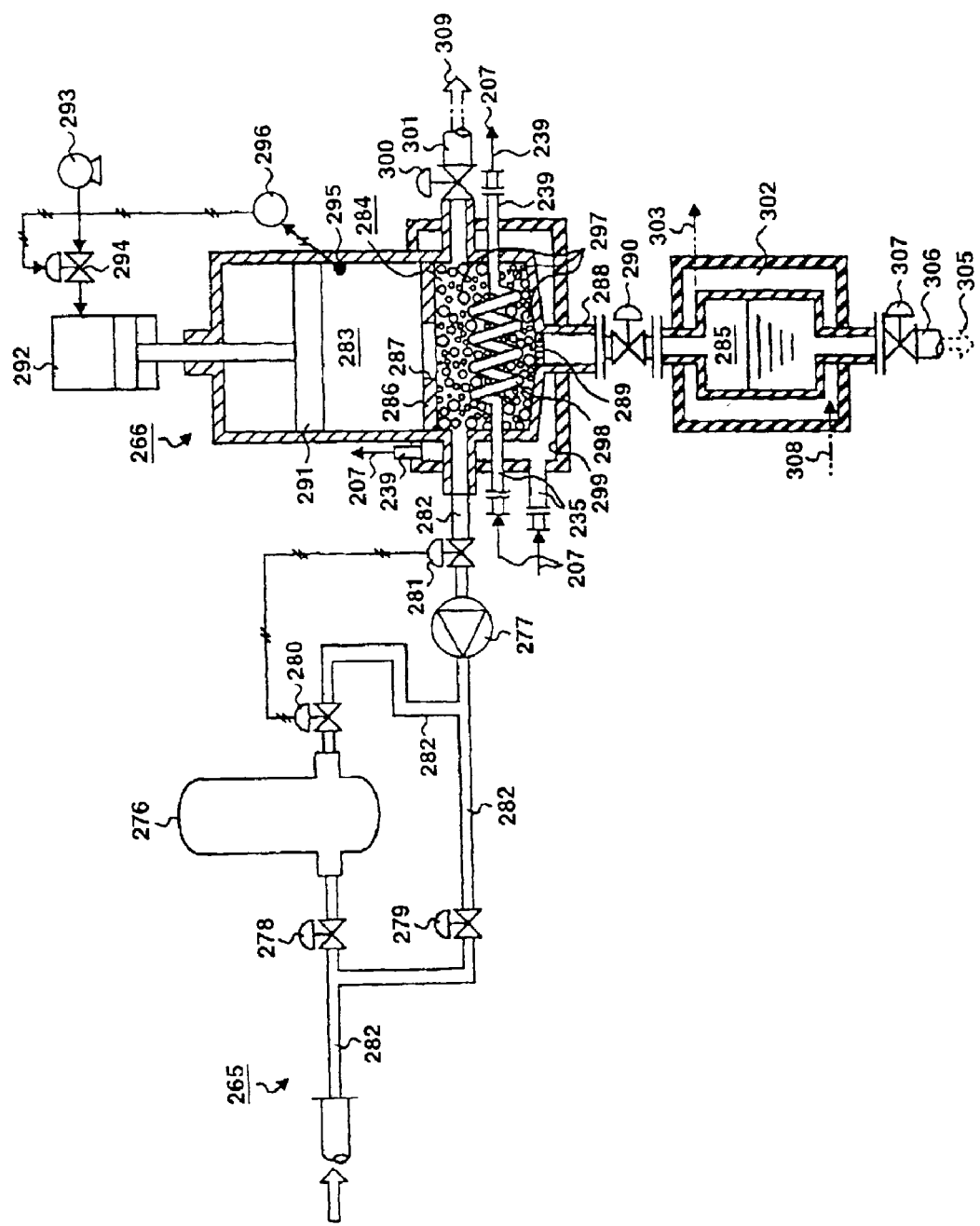
FIG. 39 is a schematic diagram of a methanol synthesis unit according to the twenty-ninth embodiment.

FIGS. 37–39 show the methanol production system according to the twenty-ninth embodiment including the biomass gasification furnace of the present invention. In FIGS. 37–39, components denoted by reference numerals identical with those in FIGS. 34–36 represent the same components.

In FIGS. 37–39, reference numerals 264, 265, and 266 represent a biomass gasification furnace, gas purification/storage equipment, and a methanol synthesis unit, respectively. The biomass gasification furnace 264 is a partially modified version of the biomass gasification furnace according to the twenty-seventh embodiment.

In the biomass gasification furnace 264, the inner walls of a combustion chamber 201 and a gasification chamber 202 are lined with a refractory material 267. A combustion gas feed line 209 which connects a combustion space 203 in the combustion chamber 201 with a combustion gas feeding passage 206 in the gasification chamber 202 is also lined with the refractory material 267, and forms a duct structure.

At the top of the combustion chamber 201 is provided an opening 268 through which biomass 210 for combustion is fed. The opening 268 is provided with an opening and closing cap 269 via a hinge mechanism 270, such that the opening can be opened or closed. The opening and closing cap 269 is provided with a handle 271 for opening and closing the cap 269. The opening and closing cap 269 represented by two-dot lines in FIG. 38 shows an opened position, and the cap 269 represented by solid lines shows a closed position.

As described above, in the biomass gasification furnace 264 of a type in which the combustion chamber 201 and the gasification chamber 202 are provided separately, the opening 268 for feeding and the opening and closing cap 269 are provided in the combustion chamber 201. Thus, substances having a large size rather than being in granular form, such as wood chips, can be used as the biomass 210 for combustion.

The opening and closing cap 269 is connected to a feeding line 212 for feeding the biomass 210 for combustion via a feeding unit 211, and is connected to a feeding line 215 for feeding an oxidizing agent 213 via a feed control valve 214. In the biomass gasification furnace 264, the combustion gas feed line 209 and an ignition burner 238 are provided below a grate 237 of the combustion chamber 201.

In the gasification chamber 202, a feed hopper 256 for feeding biomass 226 for gasification, an opening and closing valve 272, a feeding unit (feeding valve) 227, and a feed line 228 are connected to a reaction tube 240.

In the gasification chamber 202, a heat exchanger 243 is installed along a discharge line 230 for discharging a synthesis gas 229. The heat exchanger 243 includes a water-cooling jacket of dual-tube structure. The outlet end of the heat exchanger 243 for the synthesis gas 229 is connected to the inlet end of a heat exchanger 244 installed along a discharge line 235 for discharging a combustion gas 207 via a feed line 246 and a pressure control valve 273.

In the gasification chamber 202, the outlet end of the heat exchanger 244 for the combustion gas 207 is connected to the gasification chamber 202 (i.e., a lower section of the reaction tube 240) via the feeding line 246 and a flow control valve (or a pressure control valve) 274. The flow control valve 274 also regulates the temperature of heated steam 245 to be fed to the reaction tube 240.

(Description of Gas Purification/Storage Equipment)

The gas purification/storage equipment 265 includes cleanup equipment 275, a storage tank 276, a booster pump 277, a first opening and closing valve 278, a second opening and closing valve 279, a third opening and closing valve 280, and a fourth opening and closing valve 281.

The cleanup equipment 275 includes a dust-removing unit (not illustrated) and a desulfurization unit (not illustrated). A $CO_2$-removing unit (not illustrated) for removing $CO_2$ which is not required for methanol synthesis from the synthesis gas 229 may be installed in the cleanup equipment 275 in accordance with needs.

A discharge line 230 (i.e., a feeding line 282 for feeding the synthesis gas 229) for discharging the synthesis gas 229 obtained from the biomass gasification furnace 264 is connected to the cleanup equipment 275. The storage tank 276 is connected to the cleanup equipment 275 via the first opening and closing valve 278 and the feeding line 282. The booster pump 277 is connected to the cleanup equipment 275 via the second opening and closing valve 279 and the feeding line 282. The booster pump 277 is also connected to the storage tank 276 via the third opening and closing valve 280 and the feeding line 282. The outlet of the booster pump 277 is connected to the methanol synthesis unit 266 via the fourth opening and closing valve 281 and the feeding line 282.

(Description of Methanol Synthesis Unit)

The methanol synthesis unit 266 includes a pressurizing chamber 283, a catalyst chamber 284, and a methanol recovery chamber 285. The pressurizing chamber 283 and the catalyst chamber 284 are formed within a single chamber, and a partition 286 is provided therebetween. The partition 286 is provided with a large number of perforations 287. Therefore, the pressurizing chamber 283 is in communication with the catalyst chamber 284 via the perforations 287 of the partition 286.

The catalyst chamber 284 and the methanol recovery chamber 285 are connected via a connection line 288. A partition plate 289 having a large number of perforations is provided between the bottom of the catalyst chamber 284 and the connection line 288. An opening and closing valve 290 is provided in the way of the connection line 288. Therefore, the catalyst chamber 284 is in communication with the methanol recovery chamber 285 via the partition plate 289 and the opening and closing valve 290.

A pressurizing piston 291 is provided in the pressurizing chamber 283. A hydraulic cylinder 292 is connected to the pressurizing piston 291. A hydraulic pump 293 is connected to the hydraulic cylinder 292 via a control valve 294. A pressure detection means 295 is provided in the pressurizing chamber 283. A controlling means 296 for controlling the driving pressure of the hydraulic cylinder 292 is provided between the pressure detection means 295 and the control valve 294.

The pressurizing piston 291, the hydraulic cylinder 292, the hydraulic pump 293, the control valve 294, the pressure detection means 295, and the controlling means 296 constitute a pressurizing unit. The pressurizing unit controls the pressure in the pressurizing chamber 283 and the catalyst chamber 284 to the optimum pressure for methanol gas synthesis; i.e., 10 to 40 ata.

The catalyst chamber 284 is filled with a catalyst 297 such as a CuO catalyst or ZnO catalyst. A heating coil 298 is provided in the catalyst chamber 284, and a heating jacket 299 is provided outside of the catalyst chamber 284.

The discharge line 235, which discharges the combustion gas 207 which has passed through the heat exchanger 244 of the biomass gasification furnace 264, is branched into two lines. One of the branched lines is connected to the inlet of the heating coil 298, and the other is connected to the inlet of the heating jacket 299. The outlet of the heating coil 298 and the outlet of the heating jacket 299 are connected to the combustion space 203 of the biomass gasification furnace 264 via a recovery line 239. Therefore, the interior temperature of the catalyst chamber 284 is controlled to an optimum temperature for methanol synthesis; i.e., 200–400° C.

The feeding line 282 for feeding the synthesis gas fed from the gas purification/storage equipment 265 is connected to the inlet of the catalyst chamber 284. An opening and closing valve 300 and a discharge line 301 are connected to the outlet of the catalyst chamber 284.

A water-cooling jacket 302 is provided outside of the methanol recovery chamber 285. A feed line for feeding cooling water 308 is connected to the inlet of the water-cooling jacket 302. The outlet of the water-cooling jacket 302 is connected to the inlet of the heat exchanger 243 of the biomass gasification furnace 264 via a pump 304 and a recovery line 303 for returning cooling water. Therefore, the interior temperature of the methanol recovery chamber 285 is controlled and maintained at the boiling point of methanol (64.65° C.) or lower.

An opening and closing valve 307 and a recovery line 306 for recovering liquid methanol 305 (represented by an outlined broken arrow or a double broken arrow in FIG. 39) are connected to the bottom of the methanol recovery chamber 285.

Operation of the methanol production unit including the biomass gasification furnace according to the twenty-ninth embodiment and having the above-described configuration will be described hereinbelow.

As described above, the synthesis gas 229 is generated in the biomass gasification furnace 264. Biomass 210 for combustion is combusted in the combustion chamber 201 which is separately provided. The combustion gas 207 is utilized as a heat source in the reaction tube 240 of the gasification chamber 202, which is installed separate from the combustion chamber 201. In the reaction tube 240, the biomass 226 for gasification is gasified, to thereby yield the synthesis gas 229.

Subsequently, the synthesis gas 229 generated in the biomass gasification furnace 264 is fed to the gas purification/storage equipment 265 via the discharge line 230 and the feeding line 282. The synthesis gas 229 is purified by means of a purification unit, such as a dust-removing unit or a desulfurization unit, in the cleanup equipment 275 of the gas purification/storage equipment 265.

The purified synthesis gas 229 is directly pressurized by the booster pump 277 via the second opening and closing valve 279, and the pressurized gas is fed to the methanol synthesis unit 266 via the fourth opening and closing valve 281. Alternatively, the purified synthesis gas 229 is transferred to the storage tank 276 via the first opening and closing valve 278 for a temporary storage. After the temporary storage, the gas is fed to the booster pump 277 via the third opening and closing valve 280 and is pressurized by the booster pump 277. The pressurized gas is then fed to the methanol synthesis unit 266 via the fourth opening and closing valve 281.

The capacity of the storage tank 276 and the respective opening and closing operations of the first opening and closing valve 278 through the fourth opening and closing valve 281 are determined in accordance with the sizes and the operation conditions of the biomass gasification furnace 264 and the methanol synthesis unit 266.

The synthesis gas 229 pressurized in the gas purification/storage equipment 265 is fed to the methanol synthesis unit 266. The synthesis gas 229 is first introduced into the catalyst chamber 284 in the methanol synthesis unit 266, and then introduced into the pressurizing chamber 283 and into the methanol recovery chamber 285. The synthesis gas 229 is introduced in an amount corresponding to the total internal volume of the catalyst chamber 284, the pressurizing chamber 283, and the methanol recovery chamber 285 of the methanol synthesis unit 266 at a pressure falling within a range of atmospheric pressure to 10 ata.

During introduction of the synthesis gas 229 into the catalyst chamber 284, the pressurizing chamber 283, and the methanol recovery chamber 285, the opening and closing valve 300 is closed, and the pressurizing piston 291 is located at the upper dead point. After completion of the introduction, the fourth opening and closing valve 281 is also closed so as to prevent the catalyst chamber 284, the pressurizing chamber 283, and the methanol recovery chamber 285 from communicating with the outside.

Subsequently, the pressurizing unit is initiated to drive. Then, the catalytic reaction of the synthesis gas 229 proceeds by the action of the catalyst 297 under a predetermined pressure of 10–40 ata and at a predetermined temperature of 200–400° C., to thereby synthesize methanol gas.

As the methanol gas production proceeds, methanol gas diffuses and flows from the catalytic chamber 284 into the methanol recovery chamber 285 via the perforations in the partition plate 289. In the methanol recovery chamber 285, methanol gas is cooled to a temperature equal to or lower than the boiling point of methanol (64.65° C.) so as to be liquefied. The liquid methanol 305 is stored in the methanol recovery chamber 285.

As the above-described reaction process (i.e., production of methanol gas from the synthesis gas 229, and liquefaction of methanol gas to yield the liquid methanol 305) proceeds, partial pressures of $H_2$ and CO gas contained in the synthesis gas 229 is decreased, resulting in pressure drop in the catalyst chamber 284, the pressurizing chamber 283, and the methanol recovery chamber 285. During the reaction process, the above-described reactions proceed simultaneously. Therefore, the ratio $[CH_3OH]/[CO, H_2]$ remains constant, and thus the reaction $[CO]+[2H_2] \rightarrow CH_3OH$ proceeds continuously.

The pressure detection means 295 in the pressurizing chamber 283 detects the pressure drop, and the resultant detection signal is transmitted to the controlling means 296. Subsequently, a control signal is transmitted from the controlling means 296 to the control valve 294. As a result, the amount of pressurized oil supplied through the hydraulic pump 293 to the hydraulic cylinder 292 is regulated. Therefore, the pressure of the catalyst chamber 284, the pressurizing chamber 283, and the methanol recovery chamber 285 is controlled to maintain a predetermined value.

When the above-described reaction process reaches the final stage, $H_2$ and CO gas contained in the synthesis gas 229 are consumed, and the gas becomes a $CO_2$-rich gas. In other words, the partial pressures of $H_2$ and CO gas in the synthesis gas 229 decrease, whereas the partial pressure of $CO_2$ gas relatively increases. In the above-described reaction, in general, the relation [$CH_3OH$]/[$H_2$], [CO]=0.3–0.5 is satisfied.

When the above-described reaction process reaches the final stage, the partial pressure of $CO_2$ gas increases. However, $CO_2$ gas does not participate in methanol synthesis, and thus $CO_2$ gas becomes a residual gas 309. The residual gas 309 contained in the catalyst chamber 284, the pressurizing chamber 283, and the methanol recovery chamber 285 is purged by opening the opening and closing valve 300, and by closing the opening and closing valve 290. The liquid methanol 305 recovered in the methanol recovery chamber 285 is recovered by opening the opening and closing valve 307.

After a single procedure including introduction of the synthesis gas 229, production of methanol gas, liquefaction of methanol gas, purging of the residual gas 309, and recovery of the liquid methanol 305 is completed in the methanol synthesis unit 266, the synthesis gas 229 is introduced into the unit again, and the same procedure is repeated.

As described above, the methanol production unit including the biomass gasification furnace according to the twenty-ninth embodiment employs a batch production method for methanol synthesis in the methanol synthesis unit 266. Thus, a higher ratio of the amount of gas per unit amount of catalyst (i.e., S/V ratio) can be attained. In other words, $H_2$ and CO contained in the synthesis gas can be effectively utilized for methanol ($CH_3OH$) synthesis. In addition, synthesis of methanol (i.e., production of methanol gas) and liquefaction of methanol can be carried out simultaneously in the same unit (methanol synthesis unit 266). Moreover, equipment such as a recirculation line for synthesis gas, which is required for a methanol synthesis unit of continuous production, can be omitted, resulting in a simpler structure and a simpler control mechanism.

The methanol production unit including the biomass gasification furnace according to the present embodiment employs the methanol synthesis unit 266 for batch production, whereas the biomass gasification furnace 264 produces the synthesis gas 229 continuously through continuous operation. However, continuous operation of the methanol production unit as a whole can be attained through temporary storage in the storage tank 276 of the synthesis gas 229 fed from the biomass gasification furnace 264.

In the methanol production unit according to the present embodiment including a biomass gasification furnace, a heating coil 298 and a heating jacket 299 serving as means for heating the catalyst chamber 284 are connected to the discharge line 235 provided for discharging the combustion gas 207 produced in the biomass gasification furnace 264, to thereby recycle the waste heat produced in the biomass gasification furnace 264.

The methanol production unit including the biomass gasification furnace according to the twenty-ninth embodiment can recycle the cooling water 308 which has been used in the methanol synthesis unit 266. Such recycling can be attained by means of connecting the water-cooling jacket 302, which serves as a cooling means for the methanol recovery chamber 285, to the heat exchangers 243 and 244 of the biomass gasification furnace 264 via the cooling water recovery line 303.

The methanol production unit according to the twenty-ninth embodiment employs a modified form of the biomass gasification furnace 264 according to the twenty-seventh embodiment. However, the methanol production unit of the present invention may employ, a modified form of the biomass gasification furnace according to the twenty-sixth or twenty-eighth embodiment.

The methanol production unit of the present invention may employ a conventional biomass gasification furnace instead of the biomass gasification furnace of the present invention. In other words, the methanol production unit of the present invention may be composed of a conventional biomass gasification furnace and a batch-type methanol synthesis unit.

[Thirtieth Embodiment]

A specific structure of a biomass feeding unit for feeding biomass to the above-described biomass gasification furnace will next be described.

Finely pulverized biomass as described above is obtained in the form of aggregated fine particles, each particle having a size of about 0.05–1.0 mm, and the particles are formed of complicatedly and densely entangled fibrous matter. Therefore, when such finely pulverized biomass is fed to a gasification furnace, a particular means is required in a feeding unit for feeding the particles to, for example, a gasification furnace.

As described above, finely pulverized biomass is in the form of aggregated particles in which very fine fibrous particles are densely entangled, and thus such particles are easily compressed, resulting in further complication in the entanglement of particles due to compression. This causes problematic phenomena that the finely pulverized biomass forms a bridge in the hopper to close the outlet of the hopper, and uneven flow of the biomass occurs. In either case, continuous, uniform release of the finely pulverized biomass from the hopper becomes difficult. FIG. 40 depicts examples of such phenomena.

Figure 40A:
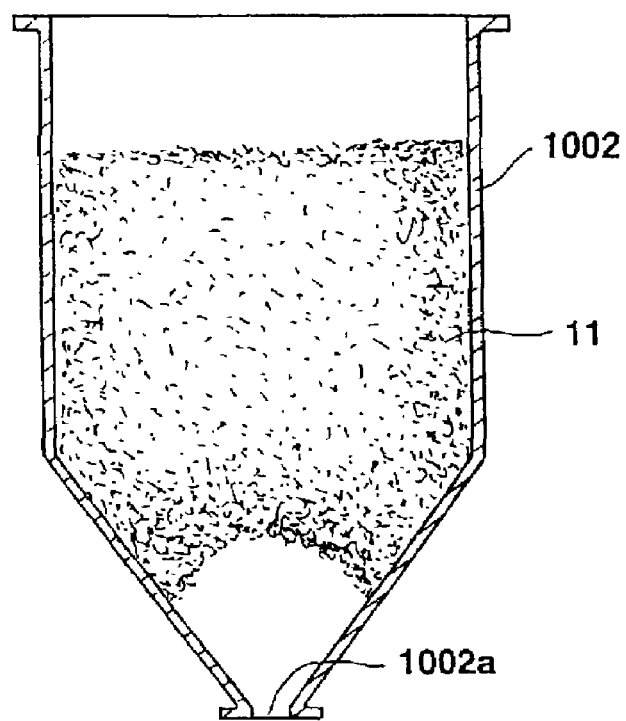
FIG. 40 is a schematic diagram of a feeding hopper for feeding biomass.
Figure 40B:
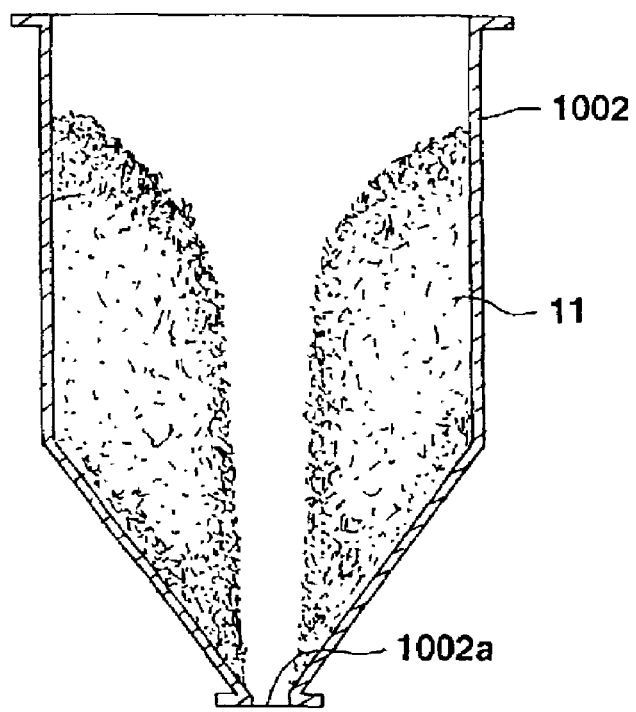

FIG. 40(A) shows a state in which finely pulverized biomass 11 forms a bridge in a hopper 1002 and closes an outlet 1002a of the hopper. FIG. 40(B) shows the case in which the finely pulverized biomass 11 is compressed and entangled in a hopper 1002 to assume a stable form shown in the figure, and thus the flow of the biomass is not uniform or release of the biomass through an outlet 1002a is difficult.

When finely pulverized biomass is discharged by use of a customary screw feeder serving as a quantitative feeding machine of particles, periodic pulsation of the discharge amount occurs. Discharge of the finely pulverized biomass will next be described in more detail with reference to drawings.

FIG. 41 schematically shows a particle quantitative feeding machine employing a screw feeder according to a conventional art. As shown in FIG. 41, a screw feeder 1003 includes a casing 1003a, which is an elongated box disposed horizontally; and a screw 1003b which is supported so as to rotate about the horizontal axis of the casing 1003a. The screw 1003b includes a screw shaft $1003b_1$ and a screw flight $1003b_2$ which is provided spirally along the axial direction of the screw shaft $1003b_1$. In the screw feeder 1003, a substance to be conveyed is constrained between the inner wall surface of the casing 1003a and adjacent walls of the screw flight $1003b_2$, and the substance is conveyed to the end portion of the screw feeder in the axial direction of the feeder while the screw shaft $1003b_1$ is rotated. A circular outlet $1003a_1$ which is opened downward is provided at the lower surface of the end portion of the casing 1003a. Therefore, the substance conveyed to the position of the outlet $1003a_1$ is discharged downward through the outlet $1003a_1$. In other words, when the substance constrained between the inner wall surface of the casing 1003a and adjacent walls of the screw flight $1003b_2$ is conveyed to the outlet $1003a_1$ the substance is released from the constraint, and falls downward due to gravity.

When finely pulverized biomass 11 is fed, as a substance to be conveyed, to the screw feeder 1003, the biomass is conveyed and discharged as shown in FIGS. 42(A) to 42(D). FIGS. 42(A) to 42(D) respectively show the states in which the screw shaft $1003b_1$ has been rotated by a ¼ cycle, a ½ cycle, or a ¾ cycle from the state shown in FIG. 42(A). FIG. 42(A) shows the state in which a portion of the finely pulverized biomass 11a constrained and conveyed between a screw flight $1003b_{21}$ and a screw flight $1003b_{22}$ is present immediately before an outlet $1003a_1$. FIG. 42(B) shows the state in which the endmost of the portion 11a faces the outlet $1003a_1$. When the screw shaft $1003b_1$ is rotated, a portion of the portion 11a of the finely pulverized biomass facing the outlet $1003a_1$ (the portion of the portion 11a facing the outlet $1003a_1$ is represented by light dots in FIG. 42) gradually increases. A large amount of finely pulverized biomass is entangled complicatedly in the portion 11a, since the biomass is compressed and conveyed by the screw feeder 1003. Therefore, the biomass does not fall through the outlet $1003a_1$ at the state shown in FIG. 42(C). In the state shown in FIG. 42(D), the aggregation of the portion 11a breaks by the gravity acting on the portion of the portion 11a facing the outlet $1003a_1$ and falls downward through the outlet $1003a_1$, and the portion is discharged to the outside. However, the time when the aggregation breaks cannot be specified. When the force of gravity acting on the portion of the portion 11a facing the outlet $1003a_1$ exceeds the force to maintain the aggregation by entanglement of the portion 11a, the aggregation breaks. However, the time when the aggregation breaks is not determined unconditionally. When the outlet $1003a_1$ has a circular shape, the aggregation may fail to break until the state shown in FIG. 42(D).

When the frequency at which the aggregation of the finely pulverized biomass breaks and falls is smaller and the amount of the aggregation which breaks and falls at a time is larger, pulsation in the amount of the finely pulverized biomass fed from the screw feeder 1003 becomes naturally larger. When the line forming the upstream-side edge portion of the outlet; i.e., the line crossing with the axis of the screw feeder 1003, is inclined in the inclination direction of the screw flight $1003b_2$ and at the inclination angle of the screw flight, pulsation in the feed amount of the finely pulverized biomass becomes maximum. In this case, the shape of a portion of the finely pulverized biomass which faces the outlet, the biomass being constrained between walls of the screw flight $1003b_2$ adjacent to each other, becomes a parallelogram. When the area of the parallelogram increases in proportion to the distance that the screw flight $1003b_2$ moves in the axial direction in accordance with rotation of the screw shaft $1003b_1$, a large amount of the aggregation of the finely pulverized biomass breaks as soon as the force to maintain the aggregation by entanglement becomes less than the force exerted by gravity. When the inclination angle of the line forming the upstream-side edge portion of the outlet is brought to be nearly perpendicular with respect to the axis of the screw feeder 1003, the probability of the aggregation of the finely pulverized biomass facing the outlet will break gradually increases, and thus the amount of the finely pulverized biomass falling through the outlet may be averaged. However, in consideration that if the finely pulverized biomass is employed as a raw material for gasification the biomass must be continuously fed to a gasification furnace and the feed amount must be uniform, the angle of the line forming the edge portion must be the same as that of a straight line perpendicular to the axis of the screw feeder 1003. As described above, when the line forming the upstream-side edge portion of the outlet is perpendicular to the axis of the screw feeder 1003, the frequency at which the aggregation of the finely pulverized biomass breaks and falls increases, as compared with the conventional case in which the shape of the outlet $1003a_1$ is circular. As a result, the aggregation of the biomass continuously falls through the outlet.

When the angle of the line forming the upstream-side edge portion of the outlet is gradually inclined from the angle of the line perpendicular to the axis of the screw feeder 1003 to the angle opposite the inclination angle of the screw flight $1003b_2$, in accordance with an increase in the angle of the line, the frequency at which the aggregation of the finely pulverized biomass breaks and falls may increase and the amount of the aggregation which breaks and falls at a time may decrease. This is because the finely pulverized biomass between adjacent walls of the screw flight $1003b_2$ can be gradually caused to face the outlet. Therefore, theoretically, when the line forming the upstream-side edge portion of the outlet is inclined to the opposite direction to the inclination direction of the screw flight $1003b_2$ at the inclination angle of the flight with respect to the line perpendicular to the axis of the screw feeder 1003, the amount of the finely pulverized biomass which is fed can be averaged, the biomass being fed through breakage of the aggregation of the biomass.

As described above, in the case of the screw feeder 1003 according to the conventional art, the outlet $1003a_1$ has a circular shape, and thus the frequency at which the portion 11a of the finely pulverized biomass 11 breaks and falls is small and pulsation in the feed amount of the biomass easily occurs. Such pulsation is a fatal defect of apparatus for feeding a raw material to a gasification furnace. This is because a raw material must be continuously fed to a gasification furnace, and the amount of the raw material fed to the furnace must be uniform.

In the case of the aforementioned screw feeder 1003, constraint of the conveyed finely pulverized biomass 11 is released at only one portion; i.e., at the outlet $1003a_1$. Therefore, pulsation in the feed amount of the biomass easily occurs.

In this case, techniques in relation to coal micropowder feeding unit which has been conventionally employed as a feeding unit of a coal gasification furnace cannot be applied to the aforementioned gasification furnace system in which finely pulverized biomass is employed as a raw material. Therefore, there has been demand for developing, on the basis of a completely novel concept, feeding unit for feeding finely pulverized biomass to a gasification furnace uniformly and continuously.

Figure 43A:
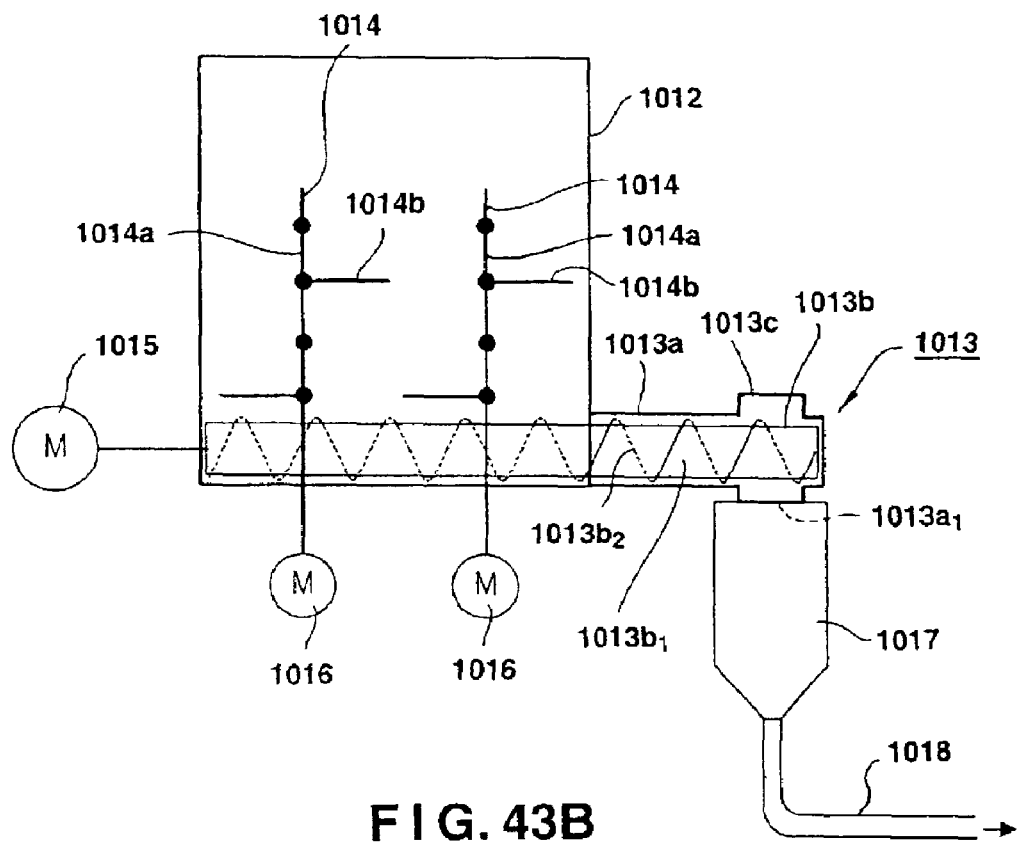
FIG. 43(A) is a side view of the feeding unit.
Figure 43B:
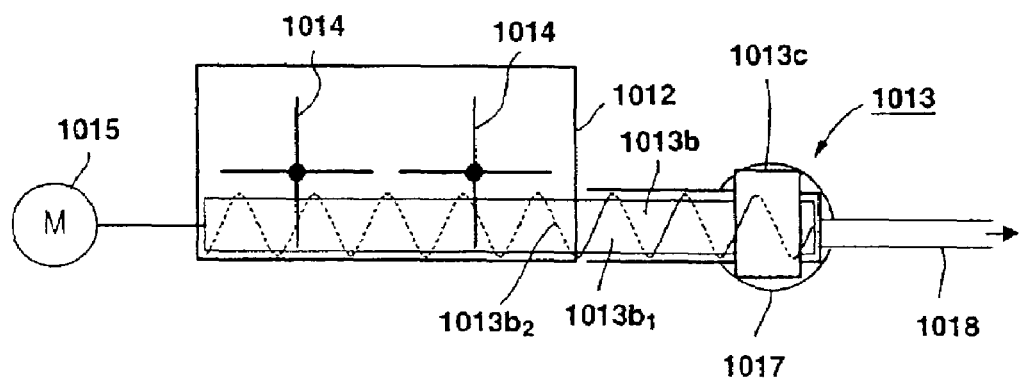
FIG. 43(B) is a plan view of the feeding unit.

FIG. 43 schematically shows a biomass feeding unit according to a thirtieth embodiment of the present invention. FIG. 43(A) is a side view of the feeding unit; and FIG. 43(B) is a plan view of the feeding unit.

As shown in FIGS. 43(A) and 43(B), a hopper 1012 is a cylindrical member for storing finely pulverized biomass which assumes the form of fibrous granules obtained by pulverizing biomass. A stirring apparatus 1014 is provided in the hopper 1012 for stirring the finely pulverized biomass stored in the hopper 1012 to thereby eliminate compression and entanglement of particles of the finely pulverized biomass. The stirring apparatus 1014 includes a perpendicular rod 1014a and a plurality of rods 1014b which are provided horizontally on a plurality of positions of the rod 1014a.

When the rod 1014 is rotated by a motor 1016, the rods 1014b are rotated on a horizontal plane to thereby stir the finely pulverized biomass.

A screw feeder 1013 is provided at the lower portion of the hopper 1012. Finely pulverized biomass is conveyed horizontally through the screw feeder 1013, and the biomass is discharged downward through an outlet $1013a_1$ provided at the distal end of a casing 1013a. When the finely pulverized biomass is stirred with the stirring apparatus 1014 in the hopper 1012, the biomass is continuously fed to the screw feeder 1013, and thus the biomass can be smoothly removed from the hopper 1012.

The screw feeder 1013 includes the casing 1013a, which is an elongated box provided horizontally, a portion of the casing being inserted into the lower portion of the hopper 1012; and a screw 1013b which is supported so as to rotate about the horizontal axis of the casing 1013a. The screw 1013b includes a screw shaft $1013b_1$ and a screw flight $1013b_2$ which is provided spirally along the axial direction of the screw shaft $1013b_1$, and the screw 1013b is rotated by a motor 1051. Therefore, in the screw feeder 1013, the finely pulverized biomass is constrained between the inner wall surface of the casing 1013a and adjacent walls of the screw flight $1013b_2$, and the biomass is conveyed to the distal end of the screw feeder along the axial direction of the feeder while the screw shaft $1013b_1$ is rotated.

A large-diameter portion 1013c having a size larger than that of the remaining portion is provided at the distal end of the casing 1013a along the axial direction of the screw feeder 1013. As a result, the finely pulverized biomass, which is compressed and constrained between adjacent walls of the screw flight $1013b_2$ and conveyed through the screw feeder, is released from the constraint at a stretch when the biomass faces the large-diameter portion 1013c. The biomass is released from the constraint over the entire circumference of the large-diameter portion 1013c. Therefore, in contrast to the case in which fibrous particles are released through one outlet provided at the lower portion of the casing 1003a of the screw feeder 1003 according to the conventional art shown in FIG. 41, the biomass is released from the compressed and entangled state over the entire circumference of the large-diameter portion, and the probability that the aggregation of the biomass breaks and falls by the force of the gravity increases. Briefly, the aggregation of the finely pulverized biomass breaks continuously.

The outlet $1013a_1$ for discharging the conveyed finely pulverized biomass is provided at the lower portion of the large-diameter portion 1013c, and the horizontal cross-section of the outlet $1013a_1$ assumes a quadrangle. On the side where the base portion of the screw feeder 1013 is present (the hopper 1012 side), the outlet $1013a_1$ has a side crossing the axis of the screw feeder 1013. The side is a straight line perpendicularly intersecting the axis direction of the screw feeder 1013. Therefore, the frequency at which the aggregation of the finely pulverized biomass breaks and falls increases, as compared with the case in which the outlet $1003a_1$ is formed into a circular shape as described in the conventional art shown in FIG. 41. Briefly, the aggregation of the biomass breaks continuously.

The aggregation of the finely pulverized biomass which is discharged and falls through the outlet $1013a_1$ is received by a fluidization cone 1017, and a gyratory flow of gas is added to the aggregation, to thereby eliminate entanglement of the fibrous particles. Through use of gas forming the gyratory flow, the fluidization cone supplies a carrier gas for carrying the finely pulverized biomass to a destination apparatus, such as a gasification furnace, through a feeding line 1018.

In the fluidization cone 1017, the falling finely pulverized biomass is disentangled by the gyratory flow, and fibrous particles of the biomass are each individually fed to the feeding line 1018. In general, when a raw material is fed to a gasification furnace, the density of the raw material is increased as much as possible, and the raw material must be fed to the furnace continuously and uniformly. Therefore, the feeding line 1018 is formed of a tube having a diameter reduced to a possible extent, and the density of the raw material is maintained at a high level by a carrier gas stream which flows at a high rate. Since entanglement of the finely pulverized biomass particles immediately causes clogging of the feeding line 1018, the biomass must be fed through the line such that entanglement of the biomass is eliminated.

Figure 44:
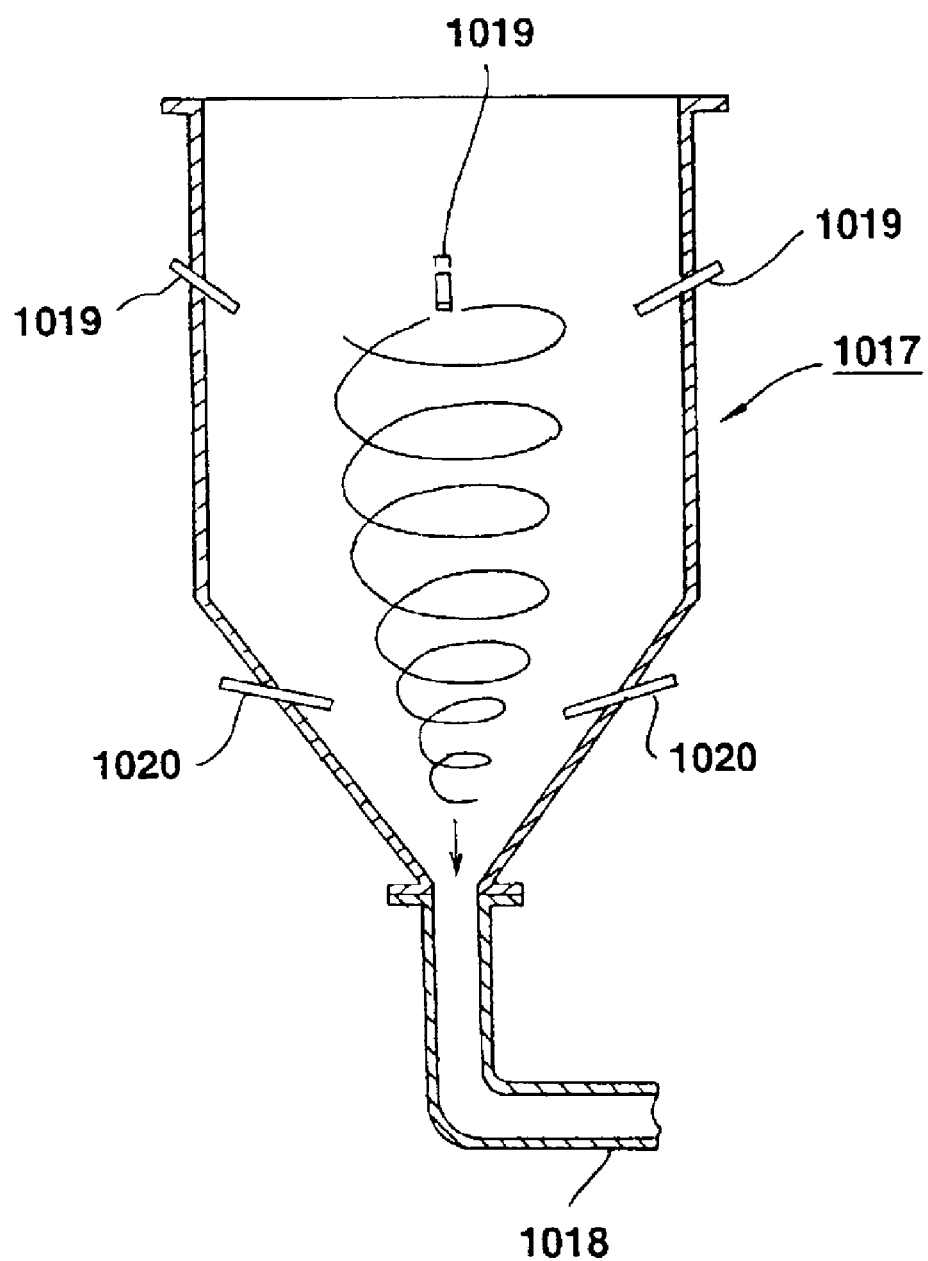
FIG. 44 is a longitudinal cross-sectional view showing an example fluidization cone according to the thirtieth embodiment.

FIG. 44 is a longitudinal cross-sectional view showing a specific example of the fluidization cone 1017 shown in FIG. 43 according to the thirtieth embodiment. As shown in FIG. 44, a plurality of injection nozzles 1019 and 1020 are radially provided on the fluidization cone 1017 at positions of two levels in height. Gas is injected from the injection nozzles 1019 and 1020 toward the mass of aggregated finely pulverized biomass falling through the opening located above. A portion having a downwardly reduced diameter is provided at the lower portion of the fluidization cone 1017, and the cone 1017 is connected, via the end of the portion, to the feeding line 1018 having a small diameter.

Figure 45:
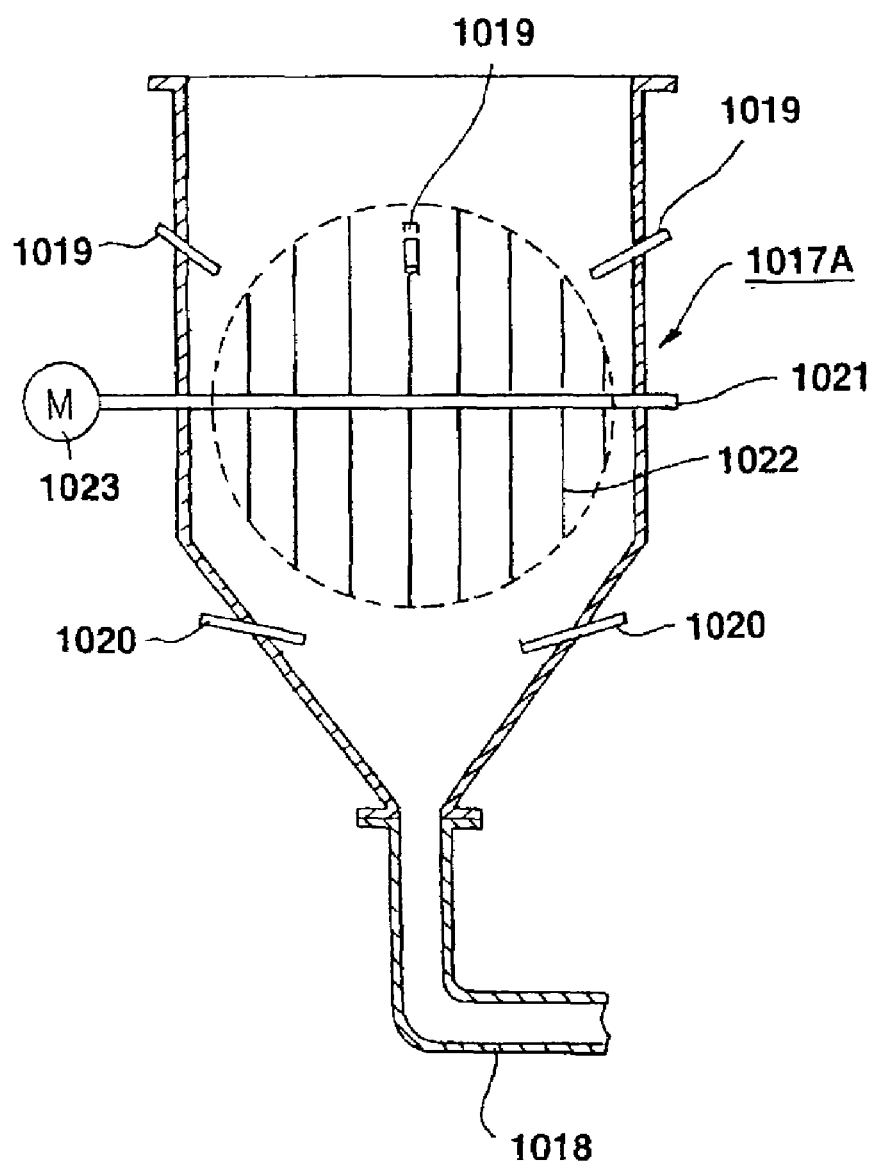
FIG. 45 is a longitudinal cross-sectional view showing another example fluidization cone according to the thirtieth embodiment.

FIG. 45 is a longitudinal cross-sectional view showing another example of the fluidization cone 1017 according to the thirtieth embodiment shown in FIG. 43. As shown in FIG. 45, a fluidization cone 1017A includes a stirring apparatus in addition to the fluidization cone 1017 shown in FIG. 44. A horizontal rod 1021 is provided at the central portion of the fluidization cone 1017A, and a plurality of stirring bars 1022 are provided on the rod 1021 so as to form a comb-like shape. When the rod 1021 is rotated by a motor 1023, the stirring bars 1022 are rotated about the rod 1021, to thereby disentangle the falling aggregation of the finely pulverized biomass.

The aggregation of the finely pulverized biomass can be sufficiently disentangled by the fluidization cone 1017 shown in FIG. 44, but the aggregation is disentangled more reliably by the fluidization cone 1017A according to this example. According to the fluidization cone 1017A, even when the gyratory flow is relatively weak, the aggregation of the finely pulverized biomass can be formed into discrete, fibrous particles.

As described above, according to the feeding unit of the thirtieth embodiment, the frequency at which the aggregation of the finely pulverized biomass facing the outlet $1013a_1$ breaks increases, whereby the biomass can be continuously fed to the fluidization cone. Accordingly, the amount of the finely pulverized biomass falling to the fluidization cone 1017 is averaged, and uniform fibrous particles of the finely pulverized biomass can be fed to a destination apparatus such as a gasification furnace, in a continuous manner and with suppressed pulsation in the feed amount of the biomass.

In the thirtieth embodiment, the outlet $1013a_1$ is formed to have a quadrangular shape having a line perpendicular to the axis of the screw feeder 1013, so as to facilitate production of the large-diameter portion 1013c. When the facilitation of production is disregarded, the shape of the outlet $1013a_1$ may be determined as follows. When the line forming the edge portion of the outlet $1013a_1$ is inclined in a direction opposite the inclination direction of the screw flight $1013b_1$, with respect to the line perpendicular to the axis of the screw feeder 1013, at an angle equal to the angle between the screw flight $1013b_1$ and the line perpendicular to the axis of the screw feeder 1013, the aggregation of the finely pulverized biomass breaks at the highest probability. In this case, the feed amount of the finely pulverized biomass can be averaged to the greatest extent.

[Thirty-First Embodiment]

Figure 46A:
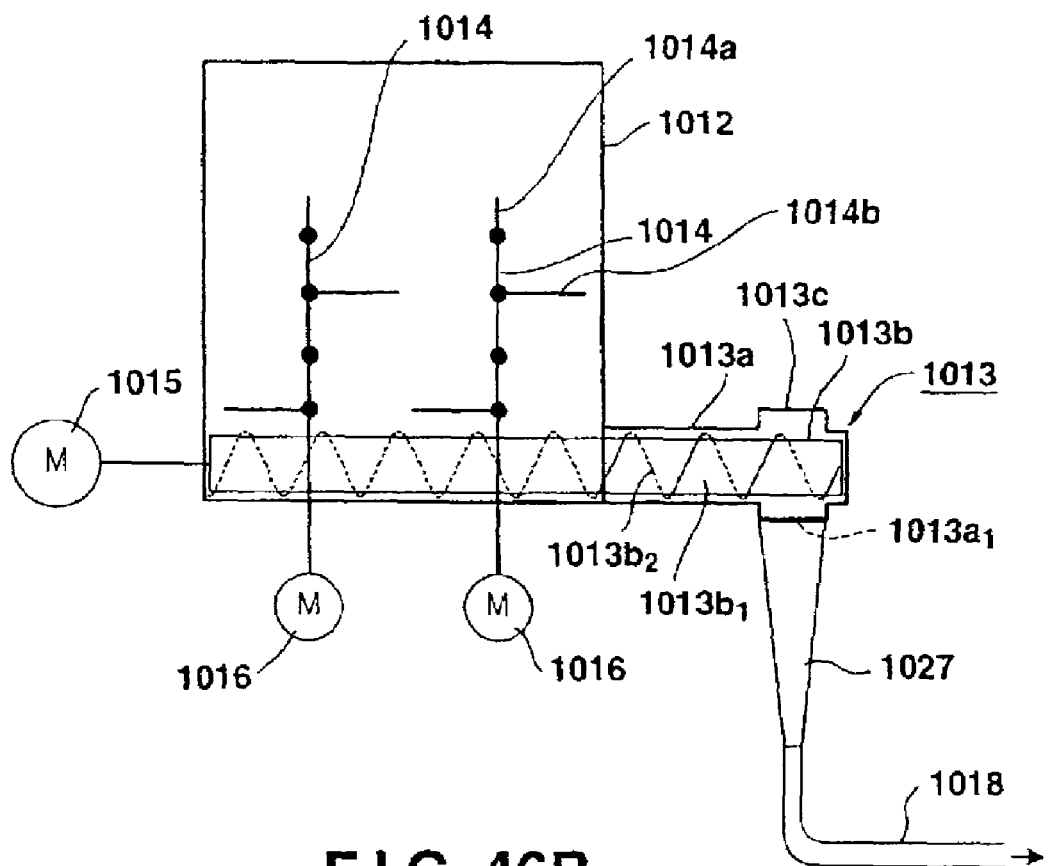
FIG. 46(A) is a side view of the feeding unit.
Figure 46B:
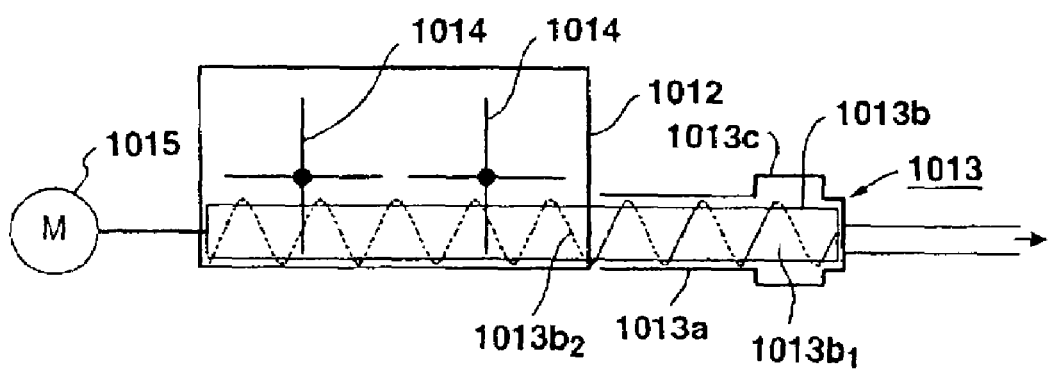
FIG. 46(B) is a plan view thereof.

FIG. 46 schematically depicts a biomass feeding unit according to a thirty-first embodiment of the present invention. FIG. 46(A) is a side view of the unit, and FIG. 46(B) is a plan view of the unit. In FIG. 46, reference numerals identical with those in FIG. 43 represent the same elements, and repeated description of such elements is omitted.

The thirty-first embodiment differs from the thirtieth embodiment in that, when the finely pulverized biomass is discharged from the screw feeder 1013, the compressed and entangled biomass is disentangled, to thereby discharge the resultant fibrous particles of the biomass as discrete, individual particles through the outlet $1013a_1$. Therefore, the screw feeder 1013 includes, at its tip portion, gas injection means for injecting gas to the finely pulverized biomass (not shown in FIG. 46, described below in detail). A funnel-shaped portion 1027 is provided so as to receive the falling finely pulverized biomass discharged from the screw feeder 1013. The funnel-shaped portion 1027 receives the falling finely pulverized biomass discharged through the outlet $1013a_1$. In the funnel-shaped portion 1027, the path of the biomass is gradually narrowed. The biomass is fed through the funnel-shaped portion 1027 to the feeding line 1018 connected to a destination apparatus such as a gasification furnace, and the aforementioned carrier gas for the finely pulverized biomass is fed by the portion 1027. Through use of the funnel-shaped portion 1027, clogging of the feeding line 1018 having a small diameter can be prevented, and the finely pulverized biomass can be smoothly fed to the destination apparatus.

Figure 47A:
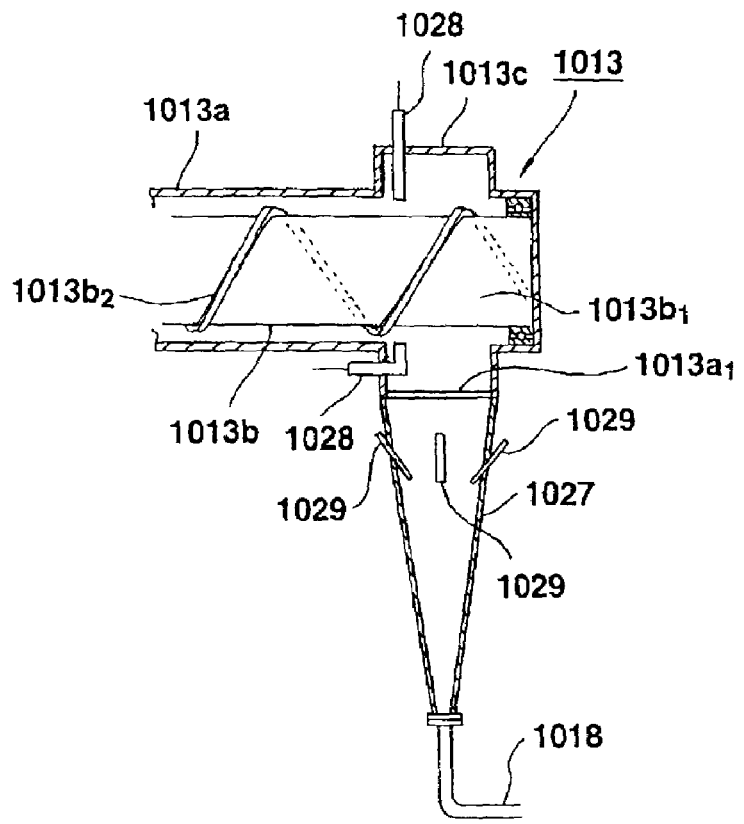
FIG. 47(A) is a longitudinal cross-sectional view of the tip portion.
Figure 47B:
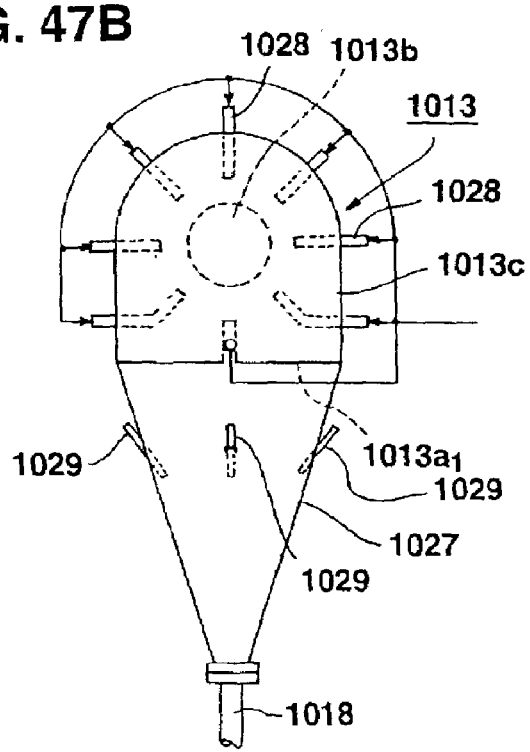
FIG. 47(B) is a right side view thereof.

FIG. 47 shows an example of a tip portion of the screw feeder shown in FIG. 46 according to the thirty-first embodiment. FIG. 47(A) is a longitudinal cross-sectional view of the tip portion, and FIG. 47(B) is a right side view of the tip portion. As shown in FIGS. 47(A) and 47(B), injection nozzles 1028 are dispersedly provided on the periphery of a large-diameter portion 1013c, and gas is injected through each nozzle 1028 to the finely pulverized biomass which is constrained between walls of the screw flight $1013b_2$ and is conveyed through the screw feeder. The flow of the gas is directed along the flow direction of the biomass conveyed through a conveying path formed between adjacent walls of the screw flight $1013b_2$. This is because, when the flow direction of the gas is determined as described above, the injected gas is most efficiently supplied to the biomass, and thus the biomass is effectively disentangled. A plurality of injection nozzles 1029 are provided at the upper portion of the funnel-shaped portion 1027. The injection nozzles 1029 are provided such that gas is injected downward. The flow of a carrier gas for conveying the finely pulverized biomass is formed by the nozzles 1029.

Figure 48:
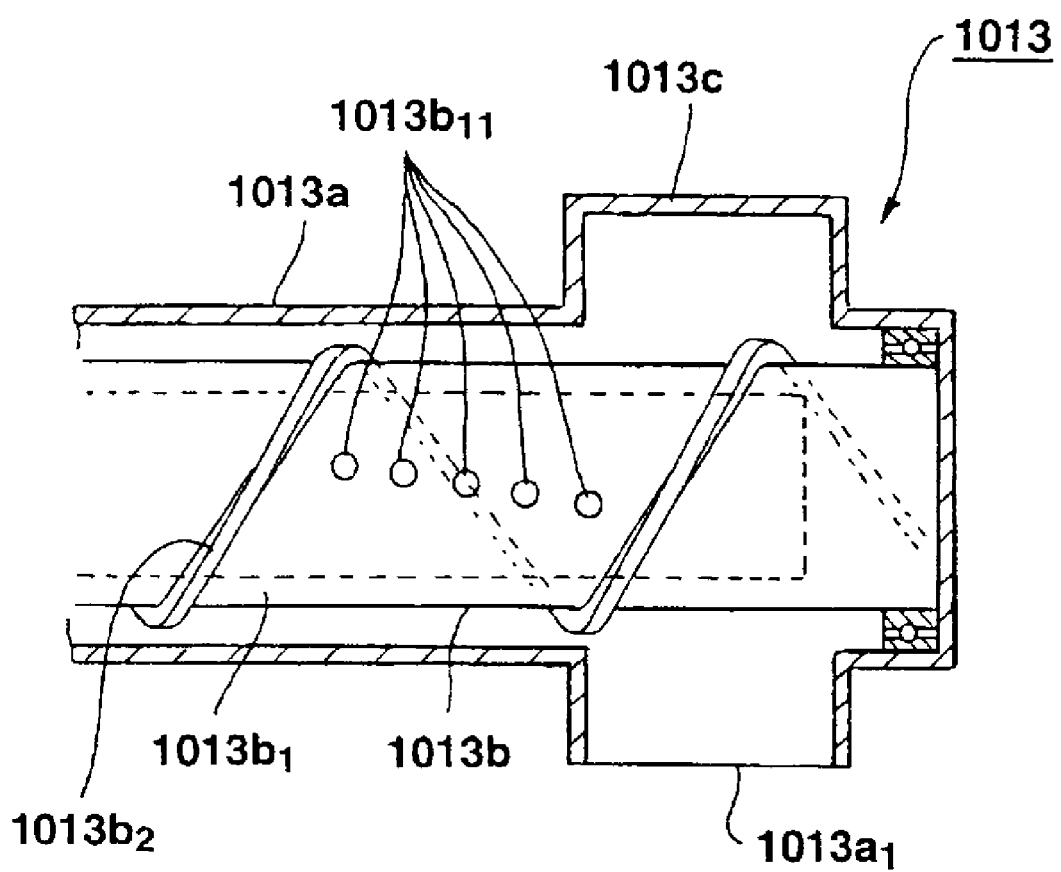
FIG. 48 is a longitudinal cross-sectional view showing another example tip portion of the screw feeder according to the thirty-first embodiment.

FIG. 48 shows a longitudinal cross-sectional view of another example of a tip portion of the screw feeder according to the thirty-first embodiment shown in FIG. 46. As shown in FIG. 48, according to this embodiment, a screw shaft $1013b_1$ is formed of a hollow member, and a plurality of perforations $1013b_{11}$ which penetrate the screw shaft $1013b_1$ from the outer surface to the interior thereof are provided between adjacent walls of the screw flight $1013b_2$ in the vicinity of the endmost portion of the shaft $1013b_1$, to thereby inject gas to the compressed finely pulverized biomass which is constrained between the walls of the screw flight $1013b_2$ and conveyed through the screw feeder. Through use of the screw feeder, compression and entanglement of the biomass is loosened or eliminated, and the resultant fibrous particles of the biomass are discharged as separate, individual particles, through an outlet $1013a_1$ downward.

In this case, the direction of gas flow; i.e., the direction of the perforation $1013b_{11}$, is determined such that the perforation is directed to oppose the direction along which the biomass is conveyed through a conveying path formed between adjacent walls of the screw flight $1013b_2$. This is because, when the direction of the gas flow is determined as described above, the gas is most efficiently applied to the biomass, and thus the biomass is effectively disentangled and disintegrated. Through the perforations $1013b_{11}$, gas is injected obliquely and upward, to thereby eliminate entanglement of the finely pulverized biomass. The perforations $1013b_{11}$ are preferably provided at a position one or two pitches distant from the endmost portion of the screw shaft $1013b_1$. This is because compression and entanglement of the finely pulverized biomass must be eliminated before the finely pulverized biomass reaches the endmost portion of the screw shaft $1013b_1$.

The above-described function is also realized by providing injection nozzles in the perforation $1013b_{11}$ and by controlling the direction of gas jetted from the nozzles.

As described above, according to the thirty-first embodiment, when the finely pulverized biomass is discharged from the screw feeder 1013, the biomass is formed into separate, independent particles. Therefore, the resultant biomass particles can be smoothly fed through the feeding line to a destination apparatus such as gasification furnace by only narrowing the path of the particles in the funnel-shaped portion 1027.

In the first and the thirty-first embodiments, the pitch between the walls of the screw flight $1013b_2$ is not described. The pitches between the walls of the screw flight $1013b_2$ are not necessarily equal to one another. The screw flight $1013b_2$ must have a sealing function, in order to prevent reverse flow of a carrier gas. In consideration of prevention of the reverse flow of the gas, the pitch between walls of the screw flight $1013b_2$ is preferably small. In contrast, in order to efficiently discharge the finely pulverized biomass from the end of the screw feeder, the pitch between the walls of the screw flight $1013b_2$ is preferably large. Therefore, in order to prevent the reverse flow of a carrier gas and to discharge the biomass efficiently from the screw feeder, relatively large pitches are provided between adjacent walls of the screw flight $1013b_2$ at the distal end portion of the screw shaft $1013b_1$, and relatively small pitches are provided between adjacent walls of the screw flight $1013b_2$ at the central portion of the screw shaft $1013b_1$, the central portion being adjacent to the distal end portion. In this case, the conveyed finely pulverized biomass is released effectively at the distal end portion of the screw shaft $1013b_1$ at which the pitch is large, and gas is effectively sealed at the central portion at which the pitch is small.

The above-described function can also be realized by gradually reducing the pitches between adjacent walls of the screw flight $1013b_2$ from the base end portion located on the hopper 1012 side to the central portion at which the pitches are minimum, and by gradually increasing the pitches from the central portion to the distal end portion of the screw feeder.

In the above-described embodiments, the case in which the finely pulverized biomass is employed as granular material is described. However, the present invention is not limited to the above embodiments. When granular material exhibiting characteristics similar to those of the biomass is employed, similar effects are obtained. The destination apparatus of such material is not particularly limited to a gasification furnace. For example, the granular material may be fed to a combustion unit.

[Thirty-Second Embodiment]

Figure 49A:
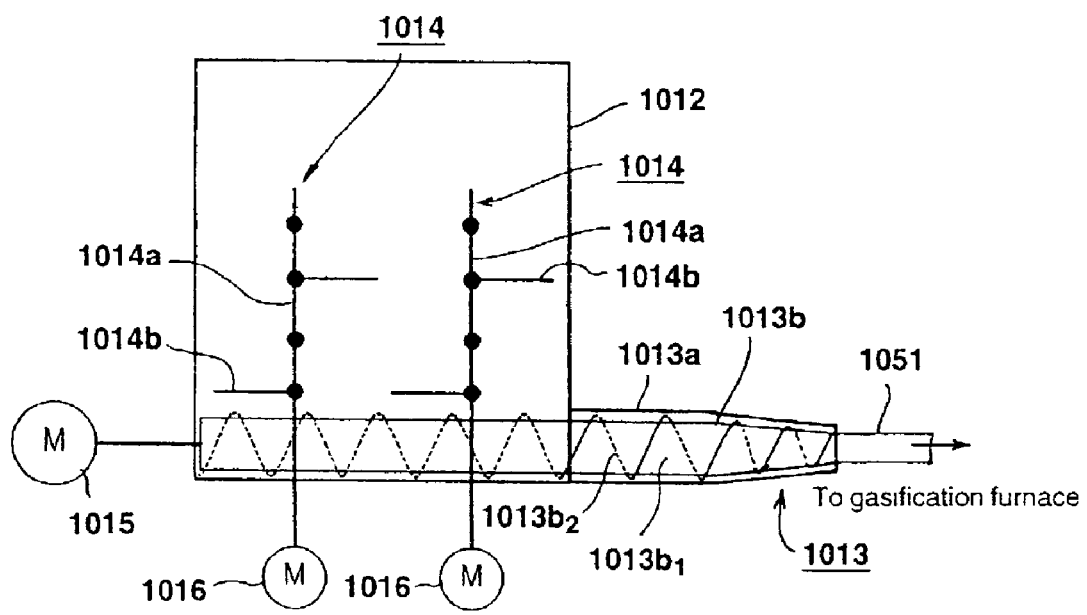
FIG. 49 depicts a biomass feeding unit according to the thirty-second embodiment, wherein FIG. 49(*a*) is a side view of the feeding unit and FIG. 49(*b*) is a plan view thereof.
Figure 49B:
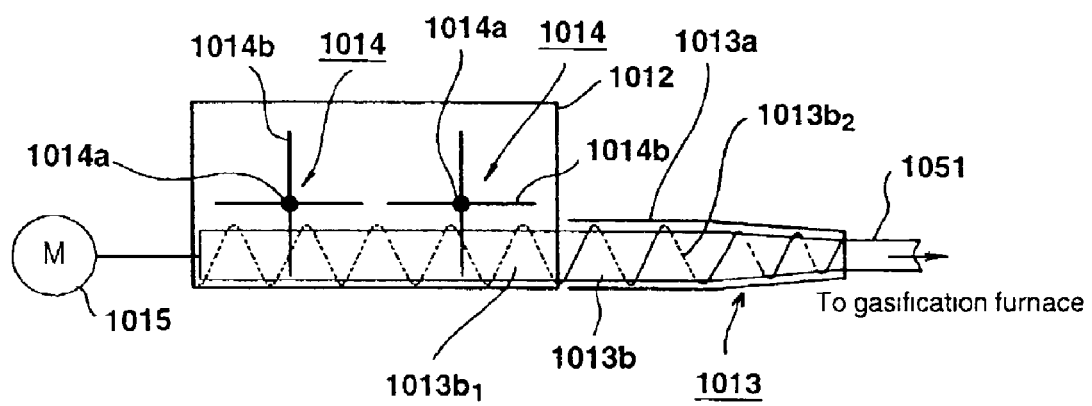

FIG. 49 schematically depicts a biomass feeding unit according to the thirty-second embodiment of the present invention. FIG. 49(A) is a side view of the feeding unit, and FIG. 49(B) is a plan view of the feeding unit. As shown in FIGS. 49(A) and 49(B), a hopper 1012 is a cylindrical member for storing finely pulverized biomass which is in the form of fibrous granular material obtained by finely pulverizing biomass. A stirring apparatus 1014 is provided in the hopper 1012 for stirring the finely pulverized biomass stored in the hopper 1012 to thereby loosen compression and eliminate entanglement of particles of the biomass. The stirring apparatus 1014 includes a vertical rod 1014a having a plurality of horizontal rods 1014b provided at a plurality of positions of the rod. When the rod 1014 is rotated by a motor 1016, the rods 1014b are rotated in a horizontal plane, to thereby stir the finely pulverized biomass.

A screw feeder 1013 is provided at the lower portion of the hopper 1012. The finely pulverized biomass is conveyed horizontally through the screw feeder 1013. The diameter of the tip portion of the screw feeder is gradually decreased, and the end of the screw feeder is connected to a feeding line 1051 having a small diameter. More specifically, the screw feeder 1013 includes a casing 1013a which is a lateral box provided horizontally, a portion of the casing being inserted into the lower portion of the hopper 1012; and a screw 1013b which is supported so as to rotate about the horizontal axis of the casing 1013a. The screw 1013b includes a screw shaft $1013b_1$ and walls of the screw flight $1013b_2$ which are provided spirally along the axis direction of the screw shaft $1013b_1$, and the screw 1013b is rotated by a motor 1016. In the screw feeder 1013, the finely pulverized biomass is constrained between the inner wall surface of the casing 1013a and adjacent walls of the screw flight $1013b_2$, and the biomass is conveyed to the end of the screw feeder along the axial direction of the feeder while the screw shaft $1013b_1$ is rotated.

At the tip portion of the screw feeder 1013, gas is injected to the finely pulverized biomass which is compressed and conveyed through the screw feeder 1013, to thereby loosen compression and eliminate entanglement of the biomass to form independent, discrete fibrous particles (the structure in relation to the above is not illustrated, and will be described in detail with reference to FIG. 50). Through use of a carrier gas stream of the above gas, the resultant fibrous particles are conveyed through the feeding line 1051 and fed to a destination apparatus such as a gasification furnace.

Figure 50A:
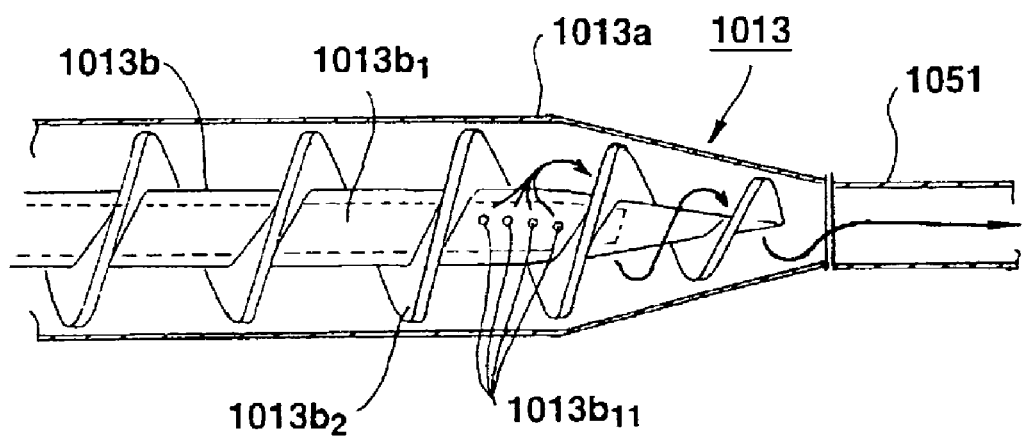
FIG. 50 is an enlarged cross-sectional view showing structures of a tip portion of the screw feeder of Example 1(A) and Example 2(B) according to the thirty-second embodiment.

FIG. 50(A) is a longitudinal cross-sectional view showing a first example of the structure of a tip potion of the screw feeder shown in FIG. 49 according to the present embodiment. As shown in FIG. 50(A), according to the first example of this embodiment, a screw shaft $1013b_1$ whose distal end portion has a spire shape is formed of a hollow member, and a plurality of perforations $1013b_{11}$ which penetrate through the shaft $1013b_1$ are provided between adjacent walls of the screw flight $1013b_2$ in the vicinity of the frontmost end portion of the shaft $1013b_1$, to thereby inject gas through the perforations $1013b_{11}$ to the compressed finely pulverized biomass which is constrained between adjacent walls of the screw flight $1013b_2$ and conveyed through the screw feeder. Through use of the screw feeder, the finely pulverized biomass is blown to the tip portion of feeder, and the biomass is released from constraint between the walls of the screw flight $1013b_2$, compression and entanglement of the biomass is loosened and eliminated, and the resultant fibrous particles of the biomass are fed, as independent, discrete particles, to the feeding line 1051. The gas applied to the biomass is employed as a carrier gas, and the biomass fibrous particles are accompanied by the carrier gas and fed to a destination apparatus. The direction of gas flow; i.e., the direction of the perforation $1013b_{11}$, is determined such that the perforation is directed to the direction that the biomass is conveyed through a conveying path formed between adjacent walls of the screw flight $1013b_2$. This is because, when the direction of the gas flow is determined as described above, the gas is most efficiently applied to the biomass, and thus compression and entanglement of the biomass is effectively eliminated. Through the perforations $1013b_{11}$, gas is injected obliquely and upward, to thereby loosen compression and eliminate entanglement of the finely pulverized biomass. The perforations $1013b_{11}$ are preferably provided at a position one or two pitches distant from the frontmost end portion of the screw shaft $1013b_1$. This is because compression and entanglement of the finely pulverized biomass must be eliminated before the frontmost end portion of the screw shaft.

The above-described function is also realized by providing injection nozzles in the perforations $1013b_{11}$ and by controlling the direction of gas injected via the nozzles.

As described above, according to the thirty-second embodiment, when the finely pulverized biomass is discharged from the screw feeder 1013, the biomass is formed into discrete, independent particles, and thus the resultant biomass particles can be smoothly fed, by a carrier gas stream, through the feeding line 1051 to a destination apparatus such as a gasification furnace.

In the thirty-second embodiment, since the area of the cross section of the path of injection gas is defined by adjacent walls of the screw flight $1013b_2$ and the inner wall surface of the casing 1013a, it is possible to reduce the area of the cross section. When the area of the cross section is smaller, the higher flow rate of the injection gas is attained easily. Therefore, the amount of the gas serving as a carrier gas can be reduced to the greatest possible extent. When the amount of the carrier gas is smaller, the content of the raw material (i.e., the finely pulverized biomass) can be increased. As a result, the screw feeder has a considerable advantage as a raw material feeding unit for a gasification furnace.

Figure 50B:
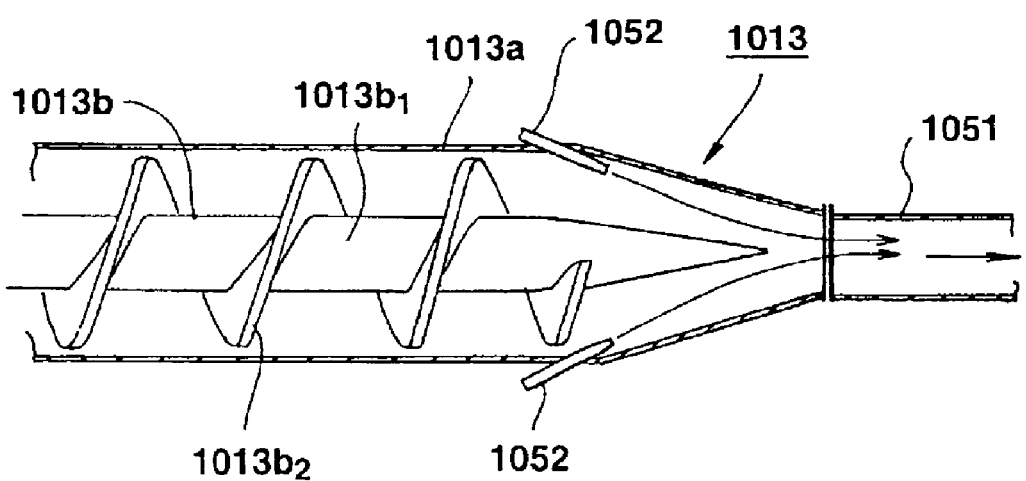

FIG. 50(B) is a longitudinal cross-sectional view showing a second example of the structure of a tip portion of the screw feeder shown in FIG. 49 according to the present embodiment. As shown in FIG. 50(B), provision of walls of the screw flight $1013b_2$ is ended in the vicinity of the base of the spire-shaped distal end portion of a screw shaft $1013b_1$, and the finely pulverized biomass conveyed to the distal end portion of the screw shaft is released from constraint by the walls of the screw flight $1013b_2$ at the base of the distal end portion. A plurality of injection nozzles 1052 are dispersedly provided on the periphery of the distal end portion of a casing 1013a, and gas is injected via each injection nozzle 1052 to the finely pulverized biomass immediately after the biomass is released from constraint by the walls of the screw flight $1013b_2$. The direction of the gas flow is determined to the axial direction of the screw shaft $1013b_1$ and a feeding line 1051. This is because, when the direction of the gas flow is determined as described above, the gas is most efficiently applied to the biomass, and thus compression and entanglement of the biomass is effectively eliminated, and the resultant biomass particles can be carried by a carrier gas most effectively.

As described above, according to the second example, when the finely pulverized biomass is discharged from the screw feeder 1013, the biomass is formed into independent, discrete particles, and thus the resultant biomass particles can be smoothly fed, on a carrier gas stream, through the feeding line 1051 to a destination apparatus such as a gasification furnace.

In this example, the area of the cross section of the path of injection gas is the area of a circular portion formed between the cross-sectional inner circle of the casing 1013a and the cross-sectional outer circle of the distal end portion of the screw shaft $1013b_1$. Since the area of the cross section is larger than that of the cross section in the case shown in FIG. 50(A), the amount of gas to be supplied increases. However, since the injection nozzles 1052 can be merely provided from the outside of the casing 1013a, the structure of the screw feeder can be simplified.

The pitches between the walls of the screw flight $1013b_2$ are not necessarily equal to one another. The screw flight $1013b_2$ must have a sealing function, in order to prevent reverse flow of a carrier gas. In consideration of prevention of reverse flow of the gas, the pitch between the walls of the screw flight $1013b_2$ is preferably small. In contrast, in order to efficiently carry out release of the finely pulverized biomass at the tip portion of the screw feeder, the pitch between the walls of the screw flight $1013b_2$ is preferably large. Therefore, in order to prevent reverse flow of a carrier gas and to carry out release of the biomass at the tip portion of the screw feeder, relatively large pitches are provided between adjacent walls of the screw flight $1013b_2$ at the distal end portion of the screw shaft $1013b_1$, and relatively small pitches are provided between adjacent walls of the screw flight $1013b_2$ at the central portion of the screw shaft $1013b_1$, the central portion being adjacent to the distal end portion. In this case, the conveyed finely pulverized biomass can be released effectively at the distal end portion of the screw shaft $1013b_1$ at which the pitch is large, and gas sealing can be effectively carried out at the central portion at which the pitch is small.

The above-described function can also be realized by gradually reducing the pitches between adjacent walls of the screw flight $1013b_2$ from the side of the hopper 1012 to the central portion at which the pitches are minimum, and by gradually increasing the pitches from the central portion to the tip portion of the screw feeder.

In the above-described embodiment, the case in which the finely pulverized biomass is employed as granular material is described. However, the present invention is not limited to the above embodiment. When granular material exhibiting characteristics similar to those of the biomass is employed, similar effects are obtained. The destination apparatus of such material is not particularly limited to a gasification furnace. For example, the granular material may be fed to a combustion treatment unit.

Industrial Applicability

As described hereinabove, a suitable application of the present invention includes a biomass gasification furnace exhibiting clean and highly efficient gasification, attaining complete gasification of biomass, and producing a gas for a highly efficient methanol synthesis; and a methanol synthesis system making use of the produced gas.

What is claimed is:

1. A methanol synthesis system making use of biomass, characterized by comprising:
   a biomass gasification furnace for gasifying biomass;
   a gas purification unit for purifying gas generated through gasification performed in the biomass gasification furnace; and
   a methanol synthesis unit for synthesizing methanol from $H_2$ and CO contained in the resultant purified gas; wherein
   the biomass gasification furnace comprises means for feeding pulverized biomass having an average particle size (D) falling within a range of $0.05 \leq D \leq 5$ mm and combustion-oxidizing-agent-feeding means for feeding oxygen or a mixture of oxygen and steam serving as a combustion-oxidizing agent, whereby gasification of the biomass is performed under gasification conditions that the mol ratio of oxygen $[O_2]$/carbon [C] in the biomass gasification furnace falls within a range of $0.1 \leq O_2/C < 1.0$, the mol ratio of steam $[H_2O]$/carbon [C] falls within a range of $1 \leq H_2O/C$; and the temperature of the interior of the furnace is 700–1,200° C.

2. A methanol synthesis system making use of biomass according to claim 1, further comprising, on the upstream side of the methanol synthesis unit, a CO shift reaction unit for adjusting the compositional ratio of $H_2$ to CO gas contained in a gas.

3. A methanol synthesis system making use of biomass according to claim 1, further comprising a carbon dioxide removal unit provided on the upstream side of the methanol synthesis unit.

4. A methanol synthesis system making use of biomass according to claim 1, wherein the internal pressure of the biomass gasification furnace is 1–30 atm, and gasification conditions include a superficial velocity of 0.1–5 m/s.

5. A methanol synthesis system making use of biomass according to claim 1, wherein the combustion-oxidizing agent is fed to a plurality of stages in the biomass gasification furnace.

6. A methanol synthesis system making use of biomass according to claim 1, wherein fossil fuel is fed into the biomass gasification furnace.

7. A methanol synthesis system making use of biomass according to claim 1, wherein biomass and a combustion-oxidizing agent are fed into the biomass gasification furnace such that the compositional ratio $H_2$/CO of the generated gas approaches 2.

8. A methanol synthesis system making use of biomass according to claim 1, wherein steam serving as the combustion-oxidizing agent is high-temperature steam of at least 300° C.

9. A methanol synthesis system making use of biomass according to claim 1, further comprising steam reforming means provided in the vicinity of an upper outlet of the biomass gasification furnace or on the downstream side of the gasification furnace.

10. A methanol synthesis system making use of biomass according to claim 1, further comprising feeding means for feeding biomass provided at a top section of a gasification furnace main body, and an ash receiving section provided in a bottom section of the gasification furnace main body.

11. A methanol synthesis system making use of biomass according to claim 10, further comprising a gas discharge tube provided at a lower portion of a side wall of the gasification furnace main body so as to discharge gas produced through gasification.

12. A methanol synthesis system making use of biomass according to claim 10, further comprising hollow cylindrical gas-ash introducing means having a downwardly reduced diameter and provided on an inner wall surface of the gasification furnace in the vicinity of the upper section of the gas discharge tube of the gasification furnace.

13. A methanol synthesis system making use of biomass according to claim 10, further comprising a gas discharge tube for discharging produced gas provided at the center of a top section of the biomass gasification furnace, the gas discharge tube extending vertically such that a lower end portion of a predetermined length of the gas discharge tube is inserted into the interior of the gasification furnace with the lower-end opening of the gas discharge tube facing the interior of the furnace.

14. A methanol synthesis system making use of biomass according to claim 10, wherein the diameter of a lower half portion of the gasification furnace main body is slightly reduced as compared with the diameter of an upper half portion of the main body; a partition is provided vertically in the interior of the diameter-reduced portion of the gasification furnace main body, thereby forming a path for introducing produced gas and ash; the produced gas and ash are caused to pass through the path; and the produced gas is forced to turn at a frontal edge of the partition, thereby removing the ash and discharging the produced gas from the gas discharge tube.

15. A methanol synthesis system making use of biomass according to claim 7, further comprising:
heat exchanging means for removing steam contained in purified gas; and
a CO shift reaction unit for adjusting the compositional ratio of $H_2$ to CO gas contained in the purified gas.

16. A methanol synthesis system making use of biomass according to claim 15, further comprising, on an upstream side of the methanol synthesis unit, a carbon dioxide removal unit for removing $CO_2$ in produced gas.

17. A methanol synthesis system making use of biomass according to claim 1, wherein the biomass gasification furnace and the methanol synthesis unit are mounted on a base or a traveling carriage so as to enable conveyance or transportation.

18. A methanol synthesis system making use of biomass according to claim 15, wherein water discharged from the heat exchanging means is converted to heated steam, by recovering heat generated during the course of methanol synthesis by the employment of the methanol synthesis unit and heat from a gas produced in the biomass gasification furnace; and said heated steam is supplied to the biomass gasification furnace.

19. A methanol synthesis system making use of biomass according to claim 18, further comprising an adsorption column or a guard column inserted between a booster unit and a regenerator and/or between the regenerator and the methanol synthesis unit.

20. A methanol synthesis system making use of biomass according to claim 18, wherein the methanol synthesis unit is a synthesis column comprising a plurality of stages of catalyst layers, and at least two series of the synthesis columns are provided.

21. A methanol synthesis system making use of biomass according to claim 20, wherein the catalyst layer placed on an inlet side of the synthesis column serves as a guard column, and, during synthesis of methanol, a first synthesis column and a second synthesis column are used alternately, and when one synthesis column is in use, among a plurality of stages of catalyst layers in the other synthesis column, the first-stage catalyst layer on a gas inlet side is removed, the second- and subsequent-stage catalyst layers are sequentially moved to serve as the first- and subsequent-stage catalyst layers, and a new additional catalyst layer is inserted so as to be placed at the position of the final stage.

22. A methanol synthesis system making use of biomass according to claim 18, wherein the recovered heat generated during the course of production of methanol is utilized for drying biomass.

23. A methanol synthesis system making use of biomass according to claim 1, wherein
the biomass gasification furnace comprises a combustion space for combusting the biomass and a gasification space for gasifying the biomass, the spaces being provided separately, and a combustion gas feeding line for feeding the combustion gas from the combustion space to the gasification space is provided between the combustion space and the gasification space; and
the methanol synthesis unit comprises a pressurizing chamber, a catalyst chamber, and a methanol recovery chamber, and operates such that the synthesis gas introduced from the biomass gasification furnace into the pressurizing chamber, the catalyst chamber, and the methanol recovery chamber is pressurized at a predetermined pressure, to thereby transform the synthesis gas into methanol through catalytic reaction in the catalyst chamber, the methanol is liquefied in the methanol recovery chamber, and the liquefied methanol is recovered and the residual gas is purged.

24. A methanol synthesis system making use of biomass according to claim 23, wherein the combustion space and the gasification space are provided in separately disposed combustion and gasification chambers, respectively; a reaction tube is provided in the gasification chamber; the gasification space is provided in the reaction tube; a combustion gas feeding passage connected to the combustion gas feeding line is provided between the inside wall surface of the gasification chamber and the outside wall surface of the reaction tube; and perforations for uniformly feeding the combustion gas from the combustion gas feeding passage to the reaction tube are provided in the reaction tube.

25. A methanol synthesis system making use of biomass according to claim 23, wherein the combustion space and the gasification space are provided in separately disposed combustion and gasification chambers, respectively; a reaction tube is provided in the gasification chamber; the gasification space is provided in the reaction tube; and a combustion gas feeding passage connected to the combustion gas feeding line is provided between the inside wall surface of the gasification chamber and the outside wall surface of the reaction tube.

26. A methanol synthesis system making use of biomass according to claim 23, wherein the combustion space and the gasification space are provided in a single chamber in such a manner that the combustion space and the gasification space are separated from each other; a reaction tube is provided in the single chamber; the gasification space is provided in the reaction tube; a combustion gas feeding passage connected to the combustion gas feeding line is provided between the inside wall surface of the chamber and the outside wall surface of the reaction tube; and perforations for uniformly feeding the combustion gas from the combustion gas feeding passage into the reaction tube are provided in the reaction tube.

27. A methanol synthesis system according to claim 1 making use of biomass and equipped with a biomass gasification furnace, wherein the methanol synthesis unit comprises a pressurizing chamber, a catalyst chamber, and a methanol recovery chamber, and operates such that the synthesis gas introduced from the biomass gasification furnace into the pressurizing chamber, the catalyst chamber, and the methanol recovery chamber is pressurized at a predetermined pressure, the synthesis gas is transformed into methanol through catalytic reaction in the catalyst chamber, the methanol is liquefied in the methanol recovery chamber, and the liquefied methanol is recovered and the residual gas is purged.

28. A methanol synthesis system making use of biomass according to claim 1, wherein
the gasification furnace for gasifying biomass comprises a combustor and a reductor; and
coal micropowder is fed to the combustor and the reductor, and biomass is fed to a reductor of the gasification furnace or to a site on the downstream side of the reductor, to thereby effect gasification of the coal and gasification of the biomass simultaneously.

29. A methanol synthesis system making use of biomass according to claim 28, further comprising a steam reforming means for reforming hydrocarbons contained in the produced gas into CO and $H_2$, the reforming means being provided within a gasification furnace or at an outlet of the gasification furnace.

30. A methanol synthesis system making use of biomass according to claim 28, further comprising a CO shift reaction unit for regulating the compositional ratio of $H_2$ to CO gas contained in the purified gas.

31. A methanol synthesis system making use of biomass according to claim 28, further comprising, on the upstream side of the methanol synthesis unit, a carbon dioxide removing unit for removing $CO_2$ in the produced gas.

32. A methanol synthesis system making use of biomass, characterized in that the feeding means for feeding biomass into the biomass gasification furnace as described in claim 1 comprises:
a hollow cylindrical hopper for storing granular material, such as fibrous granular biomass obtained by finely pulverizing biomass,
a screw feeder disposed at a lower portion of the hopper and adapted to convey the granular material in a horizontal direction and to discharge the granular material to the outside through an outlet which is provided at a distal end portion of a casing of the screw feeder such that the outlet is opened downward, and
stirring means for stirring the granular material contained in the hopper such that the granular material stored in the hopper is fed to the screw feeder.

33. A methanol synthesis system making use of biomass according to claim 32, wherein a large-diameter portion having a size larger than that of the remaining portion is provided at a distal end portion of the casing along the axial direction of the screw feeder, and the outlet is provided on a lower surface of the large-diameter portion.

34. A methanol synthesis system making use of biomass according to claim 32, wherein a plurality of injection nozzles are radially provided at a distal end portion of the casing, and gas is injected through the nozzles to the granular material which has arrived as conveyed while being compressed and constrained between adjacent walls of the screw flight of the screw feeder, to thereby eliminate compression and entanglement of the granular material and discharge the granular material downward through the outlet.

35. A methanol synthesis system making use of biomass according to claim 32, wherein a screw shaft of the screw feeder is formed of a hollow member, and a perforation penetrating the screw shaft from the outer circumferential surface to the interior thereof, or an injection nozzle utilizing the perforation, is provided between adjacent walls of the screw flight in the vicinity of a distal end portion of the screw feeder, and gas is injected through the perforation or injection nozzle to the granular material which has arrived as conveyed while being compressed and constrained between adjacent walls of the screw flight, to thereby eliminate compression and entanglement of the granular material and discharge the granular material downward through the outlet.

36. A methanol synthesis system making use of biomass according to claim 32, wherein relatively large pitches are provided between adjacent walls of the screw flight at a distal end portion of the screw shaft of the screw feeder, and relatively small pitches are provided between adjacent walls of the screw flight at a central portion of the screw shaft, the central portion being adjacent to the distal end portion.

37. A methanol synthesis system making use of biomass according to claim 32, wherein pitches between adjacent walls of the screw flight of the screw shaft of the screw feeder are gradually reduced from the base portion on the hopper side to an intermediate portion at which the pitches are minimum, and the pitches are gradually increased from the intermediate portion to the distal end portion.

* * * * *